(12) United States Patent
Bose et al.

(10) Patent No.: US 9,795,716 B2
(45) Date of Patent: *Oct. 24, 2017

(54) RESORBABLE CERAMICS WITH CONTROLLED STRENGTH LOSS RATES

(71) Applicant: WASHINGTON STATE UNIVERSITY, Pullman, WA (US)

(72) Inventors: Susmita Bose, Pullman, WA (US); Amit Bandyopadhyay, Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/682,343

(22) Filed: Apr. 9, 2015

(65) Prior Publication Data
US 2015/0352248 A1 Dec. 10, 2015

Related U.S. Application Data

(62) Division of application No. 12/298,012, filed as application No. PCT/US2007/067444 on Apr. 25, 2007, now Pat. No. 9,028,871.

(60) Provisional application No. 60/794,698, filed on Apr. 25, 2006.

(51) Int. Cl.
| | | |
|---|---|---|
| A61L 27/10 | (2006.01) | |
| A61L 27/56 | (2006.01) | |
| A61L 27/58 | (2006.01) | |
| A61L 27/54 | (2006.01) | |
| A61L 27/30 | (2006.01) | |
| A61L 27/12 | (2006.01) | |
| A61L 27/32 | (2006.01) | |
| A61L 27/42 | (2006.01) | |
| C04B 35/447 | (2006.01) | |
| C04B 35/626 | (2006.01) | |

(52) U.S. Cl.
CPC .............. *A61L 27/58* (2013.01); *A61L 27/10* (2013.01); *A61L 27/12* (2013.01); *A61L 27/306* (2013.01); *A61L 27/32* (2013.01); *A61L 27/425* (2013.01); *A61L 27/54* (2013.01); *A61L 27/56* (2013.01); *C04B 35/447* (2013.01); *C04B 35/6261* (2013.01); *A61L 2400/12* (2013.01); *A61L 2420/06* (2013.01); *A61L 2430/02* (2013.01); *A61L 2430/12* (2013.01); *C04B 2235/3201* (2013.01); *C04B 2235/3206* (2013.01); *C04B 2235/3208* (2013.01); *C04B 2235/3212* (2013.01); *C04B 2235/3213* (2013.01); *C04B 2235/3232* (2013.01); *C04B 2235/3272* (2013.01); *C04B 2235/3281* (2013.01); *C04B 2235/3284* (2013.01); *C04B 2235/3291* (2013.01); *C04B 2235/34* (2013.01); *C04B 2235/3418* (2013.01); *C04B 2235/442* (2013.01); *C04B 2235/445* (2013.01); *C04B 2235/5445* (2013.01); *C04B 2235/608* (2013.01); *C04B 2235/77* (2013.01); *C04B 2235/786* (2013.01); *C04B 2235/80* (2013.01); *C04B 2235/96* (2013.01)

(58) Field of Classification Search
CPC ....... A61L 2430/02; A61L 27/56; A61L 27/10
See application file for complete search history.

(56) References Cited

U.S. PATENT DOCUMENTS

| | | | |
|---|---|---|---|
| 4,718,914 A | 1/1988 | Frey | |
| 5,026,591 A * | 6/1991 | Henn | B01D 69/10 428/198 |
| 5,032,552 A * | 7/1991 | Nonami | A61C 8/0012 106/35 |
| 5,246,530 A | 9/1993 | Bugle et al. | |
| 5,338,772 A * | 8/1994 | Bauer | A61L 27/46 428/304.4 |
| 5,484,286 A | 1/1996 | Hansson | |
| 5,843,172 A | 12/1998 | Yan | |
| 6,013,591 A | 1/2000 | Ying | |
| 6,471,993 B1 * | 10/2002 | Shastri | A61K 9/1647 424/422 |
| 6,689,170 B1 | 2/2004 | Larsson et al. | |

(Continued)

FOREIGN PATENT DOCUMENTS

| | | |
|---|---|---|
| EP | 1440669 | 2/2003 |
| EP | 1449544 | 8/2004 |

(Continued)

OTHER PUBLICATIONS

Yoshihara et al. Effects of glass composition on compressive stength of bioactive cement based on CaO—SiO2—P2O5 glass powders. (1994). Journal of Materials Science: Materials in Medicine. vol. 5. pp. 123-129.*
Zawahreh et al. Effects of TiO2, ZrO2 and Al2O3 dopants on the compressive strength of tricalcium phosphate. (2005). Journal of Materials Science: Materials in Medicine. vol. 16. pp. 1179-1184.*
Camire et al. Material characterization and in vivo behavior of silicon substituted alpha-tricalcium phosphate cement. Sep. 23, 2005. J Biomed Mater Res B Appl Biomater. <htto://dx.doi.org/10.1002/jbm.b.30385>.*
Yin, et al., "Density Functional Study of Structural, Electronic and Vibrational properties of Mg-and Zn-doped Tricalcium Phosphate Biomaterials", Biomaterials 23 f201 4155-4163 (2002).

(Continued)

*Primary Examiner* — Tracy Liu
(74) *Attorney, Agent, or Firm* — Liang IP, PLLC

(57) ABSTRACT

Particular aspects of the present disclosure provide bioresorbable and biocompatible compositions for bioengineering, restoring, or regenerating tissue or bone. In one embodiment, a biocompatible composition includes a three-dimensional porous or non-porous scaffold material comprising a calcium phosphate-based ceramic having at least one dopant therein selected from metal ion dopants or metal oxide dopants. The composition is sufficiently biocompatible to provide for a cell or tissue scaffold, and resorbable at a controlled resorption rate for controlled strength loss under body, body fluid or simulated body fluid conditions.

23 Claims, 32 Drawing Sheets

(56) References Cited

U.S. PATENT DOCUMENTS

| | | | |
|---|---|---|---|
| 6,790,233 | B2 | 9/2004 | Brodke et al. |
| 7,048,541 | B2 | 5/2006 | Hall et al. |
| 2002/0062154 | A1 | 5/2002 | Ayers |
| 2002/0173850 | A1 | 11/2002 | Brodke et al. |
| 2003/0193106 | A1* | 10/2003 | Yu ............................ A61L 27/56 264/109 |
| 2004/0019385 | A1 | 1/2004 | Ayers et al. |
| 2004/0023784 | A1 | 2/2004 | Yu et al. |
| 2004/0082999 | A1 | 4/2004 | Mathys, Jr. et al. |
| 2004/0101822 | A1 | 5/2004 | Wiesner et al. |
| 2004/0142013 | A1 | 7/2004 | Rubsamen |
| 2004/0243237 | A1 | 12/2004 | Unwin et al. |
| 2004/0254668 | A1 | 12/2004 | Jang et al. |
| 2005/0221072 | A1 | 10/2005 | Dubrow et al. |
| 2006/0078590 | A1 | 4/2006 | Hermansson et al. |
| 2006/0188542 | A1 | 8/2006 | Bobyn et al. |
| 2006/0229715 | A1 | 10/2006 | Istephanous et al. |
| 2007/0098811 | A1 | 5/2007 | Lu et al. |
| 2007/0203584 | A1 | 8/2007 | Bandyopadhyay et al. |
| 2009/0276056 | A1 | 11/2009 | Bose |

FOREIGN PATENT DOCUMENTS

| | | |
|---|---|---|
| WO | WO9511639 | 5/1995 |
| WO | WO9966966 | 12/1999 |
| WO | WO0072777 | 12/2000 |
| WO | WO2004008984 | 1/2004 |
| WO | WO2005000159 | 1/2005 |
| WO | WO2006116752 | 11/2006 |
| WO | WO2007124511 | 11/2007 |

OTHER PUBLICATIONS

Zamir, et al., "Molecular complexity and dynamics of cell-matrix adhesions", J. Cell Sci. 114 [20] 3583-90 (2001).

Zerbo, et al., "Histomorphometry of human sinus floor augmentation using a porous 13-tricalcium phosphate: a prospective study," Clinical ora/Implant Research (2004) 15.

Zerbo, et al., Histology of human alveolar bone regeneration with a porous tricalcium phosphate. A report of two cases. Clin Ora/Implants Res. 12:379-384 (2001).

Zhang, et al., "Crystallization and microstructure analysis of calcium phosphate-based glass ceramics for biomedical applications," J. of Non-Crystalline Solids, 272 (2000) 14-21.

Bhadang, et al., "Influence of fluorapatite on the properties of thermally sprayed hydroxyapatite coatings," Biomaterials 25 (2004) 4935-4945.

Gibson, et al., "Phase Transformation of Tricalcium Phosphates Using High Temperature X-Ray Diffraction," Bioceramics vol. 9, 173-176 (1996).

Heughebaert, et al., "Physicochemical Characterization of Deposits Associated with HA Ceramics Implanted in Nonosseous Sites," J. Biomed. Mater. Res.: Applied Biomaterials (1988) 22:A3, pp. 257-268.

Kawamura, et al., "Stimulatory effect of zinc-releasing calcium phosphate implant on bone formation in rabbit femora", J. Biomed. Mater. Res., 50 f21184-190 (2000).

Legeros, et al., "In Vivo Transformation of Biphasic Calcium Phosphate Ceramics: Ultrastructural and Physicochemical Characterizations," In: CRC Handbook of Bioactive Ceramics vol. II Calcium Phosphate and Hydroxylapatite Ceramics, Yamanuro T, Hench L, Wilson J, editors. Boca Raton: CRC Press, 1990, vol. 2, pp. 17-28.

Legeros, et al., "The effect of magnesium on the formation of apatites and whitlockites," In: Magnesium in Health and Disease, Y. Itokawa & J. Durlach, eds., London: John Libbey & Co Ltd.; 11 (1989), pp. 11-19.

Moreira-Gonzalez, et al., "Evaluation of 45S5 Bioactive Glass Combined as a Bone Substitute in the Reconstruction of Critical Size Calvarial Defects in Rabbits," The J. Craniofac. Surg., Jan. 2005, vol. 16, No. 1, pp. 63-70.

Mow, et al., Basic Orthopaedic Biomechanics and Mechano-Biology, Third Edition, pp. 123-519, Lippencott Williams & Wilkins, Philadelphia, 2005.

Oki, et al., "Preparation and in vitro bioactivity of zinc containing sol-gel-derived bioglass materials," J. Biomed. Mater. Res. 69A:216-221 (2004).

Shi, Biomaterials and Tissue Engineerinq, pp. 1-215, Spriner Berlin Heidelber, New York, 2004.

Vandenburgh, et al., "Mechanically induced alterations in cultured skeletal muscle growth," J. Biomech. (1991)24: Suppl. 1, pp. 91-99.

Yin, et al., "Density Functional Study of Structural, Electronic and Vibrational properties of Mg- and Zn-doped Tricalcium Phosphate Biomaterials", Biomaterials, 23 [20] 4155-4163 (2002).

Zhang, et al., "A Comparative Study of Electrochemical Deposition and Biomimetic Deposition of Calcium Phosphate on porous Titanium", Biomaterials; 26 f16]2857-2865 (2005).

Borden et al. The sintered microsphere matrix for bone tissue engineering: In vitro osteoconductivity studies. 2002. Wiley Periodicals, Inc. pp. 421-429.

Gomes et al. Biodegradable polymers and composites in biomedical applications: from catgut to tissue engineering. 2004. Maney for the Institute and ASM International. vol. 49. No. 5. pp. 261-273.

Notice of Allowance in U.S. Appl. No. 12/211,005 issued Aug. 12, 2014, 25 pages.

Notice of Allowance in U.S. Appl. No. 11/675,006 issued Jan. 14, 2016, 9 pages.

Notice of Allowance in U.S. Appl. No. 14/538,418 issued Apr. 4, 2016, 10 pages.

Office Action in U.S. Appl. No. 11/675,006 issued May 15, 2013, 9 pages.

Office Action in U.S. Appl. No. 11/675,006 issued Feb. 12, 2014, 8 pages.

Bandyopadhyay, et al., "Calcium Phosphate-Based Resorbable Ceramics: Influence of MgO, ZnO, and Si02 Dopants," J. Am. Ceram. Soc., 89 [9], pp. 2675-2688 (2006).

Bandyopadhyay, et al., "Influence of ZnO doping in calcium phosphate ceramics", in press, Materials Science and Engineering C, Nov. 2005.

Bertoni, et al., "Nanocrystals of Magnesium and fluoride substituted hydroxyapatite". J. Inorg. Biochem., 72, 29-35 (1998).

Bose, et al., "Synthesis and characterization of hydroxyapatite nanopowders by emulsion technique," Chern Mater., 15 (23), 4464-4469 (2003).

Bose, et al., "Synthesis of hydroxyapatite nanopowders via sucrose-templated sol-gel method," Journal of the American Ceramic Society, 86 [6], pp. 1055-1057 (2003).

Bose, et al., "Pore Size and Pore Volume Effects on Alumina and TCP Ceramic Scaffolds," Materials Science and Engineerinq C, 23, pp. 479-486 (2003).

Burg, et al., "Biomaterial developments for bone tissue engineering". Biomaterials, 21 [23]2347-59 (2000).

Buser, et al., "Localized ridge augmentation using guided bone regeneration"; pp. 189-233 in Guided bone regeneration in implant dentistry, Edited by D. Buser, C. Dahlin and R. K. Schenk, Quintessenz, Chicaqo, 1994.

De Groot, "Effect of porosity and physicochemical properties on the stability, resorption, and strength of calcium phosphate ceramics". In Bioceramics: Material characteristics versus in-vivo behavior, Ann. N.Y. Acad. Sci., 523,227 (1998).

Doi, et al., "Development of a new calcium phosphate cement that contains sodium calcium phosphate," Biomaterials 22 (2001) 847-845.

Ducheyne, et al., "Bioactive ceramics: the effect of surface reactivity on bone formation and bone cell function," Biomaterials (1999) 20:23-24, pp. 2287-2303.

Fujimura, et al., "A bioactive bone cement containing Bis-GMA resin and A-W glass-ceramic as an augmentation graft material on mandibular bone," Clin Ora/Implants Res (2003) 14, pp. 659-667.

Hashizume, et al., "Stimulatory effect of 133-alanyl-1-histidinato zinc on cell proliferation is dependent on protein synthesis in osteoblastic MC3T3-E1 cells", Mol. Cell Biochem., 122, 59-64 (1993).

(56) References Cited

OTHER PUBLICATIONS

Hattiangadi, et al., "Strength Degradation of Nonrandom Porous Ceramics Under Uniaxial Compressive Loading," Journal of the American Ceramic Society, 83 [11], pp. 2730-2736 (2000).

Hayakawa, et al., "Mechanism of apatite formation on a sodium glass in a simulated body fluid", J. Am. Ceram. Soc., 82 f812155-60 (1999).

Hulbert, et al. Potential of ceramic materials as permanently implantable skeletal prosthesis. J Biomed Mater Res 1970; 4:443.

Inoue, et al., "In vivo effect of fluoride-substituted apatite on rat bone," Dent Mater J. Sep. 2005; 24 (3); 398.

Ito, et al., "Preparation, solubility, and cytocompatibility of zinc-releasing calcium phosphate ceramics", J. Biomed. Mater. Res., 50 [2]178-183 (2000).

Josch E K, et al., Chemical and physicochemical characterization of porous hydroxyapatite ceramics made of natural bone. Biomaterals. 21:1645-1658 (2000).

Kalita, et al., "Development of controlled porosity polymer-ceramic composite scaffolds via fused deposition modelinq," Materials Science and Engineerinq C 23:611-620 (2003).

Kalita, et al., "Effects of MgO—CaO—P20 5-Na20 based additives on mechanical and biological properties of hydroxyapatite," in press, Journal of Biomedical Materials Research, Jun. 2004.

Kalita, et al., "CaO—P20s—Na20 based sintering additives for hydroxyapatite (HAp) ceramics," Biomaterials, 25:12, pp. 2331-2339 (2004).

Kamakura, et al., Implanted octacalcium phosphate is more resorbable than 13-tricalcium phosphate and hydroxyapatite. J Biomed Mater Res. 59:29-34 (2002).

Kim, et al., "Synthesis of Si, Mg substituted hydroxyapatites and their sintering behaviors", Biomaterials. 24 f81 1389-98 (2003).

Kishi, et al., "Inhibitory effect of zinc compounds on osteoclast-like cell formation in mouse marrow culture", Biochem. Pharmacal., 48, 1225-1230 (1994).

Knabe, et al., Effect of rapidly resorbable calcium phosphates and a calcium phosphate bone cement on the expression of bone-related genes and proteins in vitro, J Biomed Mater Res. 69A: 145-154 15 (2004).

Knabe, et al., "The functional expression of human bone-derived cells grown on rapidly resorbable calcium phosphate ceramics", Biomaterials. 25 [2] 335-44 (2004).

Knowles, et al., "Sintering effects in a glass reinforced hydroxyapatite", Biomaterials, 17 [14] 1437 (1996).

Kokubo, et al., "Solutions able to reproduce in vivo surface-structure changes in bioactive glassceramicA-W3", J. Biomed. Mater. Res., 24,721-34 (1990).

Lansdown, Silver 2: toxicity in mammals and how its products aid wound repair 11, 173 (2002).

Larrabee, et al., A ferric calcium phosphorous oxide (FE CAP) ceramic for rebuilding bone. Biomed Sci Instrum. 29:59-64 (1993).

Leng, et al., "Identifying Calcium Phosphates Formed in Simulated Body Fluid by Electron Diffraction", Hey. Eng. Mater., 254 [25]339-42 (2004).

Manjubala, et al., Effect of Ti02Ag20 additives on the formation of calcium phosphate based functionally qraded bioceramics. Biomaterials. 21:1995-2002 (2000).

Marcacci, et al., "Reconstruction of extensive long-bone defects in sheep using porous hydroxyapatite sponges," Calcif Tissue Int (1999) 64, pp. 83-90.

Moonga, et al., "Zinc is a potent inhibitor of osteoclastic bone resorption in vitro", J. Bone Miner. Res., 10 [3]453-457 (1995).

Moritz, et al., "Local induction of calcium phosphate formation on Ti02 coatings on titanium via surface treatment with a C02 laser," J of biomed mater res A, 65 (2003) 9-16.

Otsuka, et al., Effect of controlled zinc release on bone mineral density from injectable Zncontaining 13-tricalcium phosphate suspension in zinc-deficient diseased rats. J Biomed Mater Res. 69A:552-560 (2004).

Percival, "Bone health & Osteoporosis", Appl. Nutr. Sci. Rep., 5 [4]1 (1999).

Qiu, et al., "Effect of strontium ions on the growth of ROS17 /2.8 cells on porous calcium polyphosphate scaffolds", Biomaterials; 27 f811277-86 (2006).

Ramires, et al., "The influence of titania/hydroxyapatite composite coatings on in vitro osteoblasts behaviour," Biomaterials, 22(12)1467-74 (2001).

Rodriguez-Lorenzo, et al., "Influence of fluorine in the synthesis of apatites, synthesis of solid solutions of hydroxyl-fluorapatite," Biomaterials 24 (2003) 3777-3785.

Rokusek, et al., "Interaction of human osteoblasts with bioinert and bioactive ceramic substrates", J. Biomed. Mater. Res., 75A f31588-94 (2005).

Seeley, et al., "Tricalcium phosphate based resorbable ceramics: Influence of NaF and GaO addition," Mater Sci. Enq. C, vol. 28, Issue 1, pp. 11-17 (2008).

Seeley, et al., "Influence of Ti02 and Ag 20 Addition on Tricalcium Phosphate Ceramics", J. Biomed. Mater. Res., vol. 82A, Issue 1, pp. 113-121, Jul. 2007.

Suchanek, et al., "Processing and Properties of Hydroxyapatite-Based Biomaterials for Use as Hard Tissue Replacement Implants", J. Mater. Res., 13 [1]94-109 (1998).

Tadjoedin, et al., "High concentrations of bioactive glass material (BioGran®) vs. autogenous bone for sinus floor elevation," Clinical Ora/Implants Research (2002) 13:4, pp. 428-436.

Wang, "Ca/P ratio effects on the degradation of hydroxyapatite in vitro," J. of Biomedical Materials Research part A, 67A:2, pp. 599-608.

Yaszemski, et al., "Evolution of bone transplantation: molecular, cellular and tissue strategies to engineer human bone," Biomaterials (1996) 17:2, pp. 175-185.

Anderson, J.M. et al. "Biodegradation and biocompatibility of PLA and PLGA microspheres," Advanced Drug Delivery Reviews 28 (1997) 5-24.

Andreadis, S.T. et al. ""Biomimetric approaches to protein and gene delivery for tissue regeneration,"" Trends in Biotechnology 24 (2006) 331-337.

Angeli, F. et al. "Influence of glass composition and alteration solution on leached silicate glass structure: A solid-state NMR investigation," Geochimica et Cosmochimica Acta 70 (2006) 2577-2590.

Balas, F. et al., "L-Trp adsorption into silica mesoporous materials to promote bone formation," Acta Biomaterialia 4 (2008) 514-522.

Baldwin, S.P. et al. "Materials for protein delivery in tissue engineering," Advanced Drug Delivery Reviews 33 (1998) 71-86.

Barbe, C. et al. "Silica Particles: A Novel Drug-Delivery System," Adv. Mater. 16 (2004) 1959-1966.

Blom, E.J. et al. "Transforming growth factor-131 incorporation in an a-tricalcium phosphate/dicalcium phosphate dihydrate/ tetracalcium phosphate monoxide cement: release characteristics and physiochemical properties," Biomaterials 23 (2002) 1261-1268.

Casey, W.H. et al. "Leaching and reconstruction at the surfaces of dissolving chainsilicate minerals," Nature 366 (1993) 253-256.

Chen, J.J. et al. "Solubility and structure of calcium silicate hydrate," Cement and Concrete Research 34 (2004) 1499-1519.

De Aza, P.N. et al. "Bioactivity of Wollastonite Ceramics: In Vitro Evaluation," Scripta Metallurgica et Materialia 31 (1994) 1001-1005.

De Aza, R.N. et al. "Morphological and structural study of pseudowallastonite implants in bone," Journal of Microscopy 197 (2000) 60-67.

Ginebra, M.-P. et al. "Calcium phosphate cements: Competitive drug carriers for the musculoskeletal system?," Biomaterials 27 (2006) 2171-2177.

Haesslein, A. et al. "Effect of macromer molecular weight on in vitro ophthalmic drug release from photo-crosslinked matrices," Acta Biomaterialia 4 (2008) 1-10.

Hartmann, M. "Ordered Mesoporous Materials for Bioadsorption and Biocatalysis," Chem. Mater. 17 (2005) 4577-4593.

Hartmann, M. et al. "Adsorption of Vitamin E on Mesoporous Carbon Molecular Sieves," Chem. Mater. 17 (2005) 829-833.

Hench, L.L. "Bioceramics: From Concept to Clinic," J. Am. Ceram. Sci. 74 (1991) 1487-1510.

(56) References Cited

OTHER PUBLICATIONS

Holland, T.A. et al. "Advances in drug delivery for articular cartilage," Journal of Controlled Release 86 (2003) 1-14.
Horcajada, P. et al. "Bioactivity in ordered mesoporous materials," Solid State Sciences 6 (2004) 1295-1300.
Kokubo, T. "Novel bioactive materials with different mechanical properties," Biomaterials 24 (2003) 2161-2175.
Kumta, P.N. et al. "Nanostructured calcium phosphates for biomedical applications: novel synthesis and characterization," Acta Biomaterialia 1 (2005) 65-83.
Lee, J.Y. et al. "Transforming Growth Factor (TGF)-131 Releasing Tricalcium Phosphate/Chitosan Microgranules as Bone Substitutes," Pharmaceutical Research 21 (2004) 1790-1796.
Li, P. et al. "The Electrochemistry of a Glass Surface and its Application to Bioactive Glass in Solution," Journal of Non-Crystalline Solids 119 (1990) 112-118.
Lin, K. et al. "Study of the mechanical property and in vitro biocompatibility of CaSi03 ceramics," Ceramics International 31 (2005) 323-326.
Liang, M. et al. "Multifunctional Inorganic Nanoparticles for Imaging, Targeting, and Drug Delivery," ACS Nano 2 (2008) 889-896.
Liu, X. et al. "Apatite formed on the surface of plasma-sprayed wollastonite coating immersed in simulated body fluid," Biomaterials 22 (2001) 2007-2012.
Luginbuehl, V. et al. "Localized delivery of growth factors for bone repair," European Journal of Pharmaceutics and Biopharmaceutics 58 (2004) 197-208.
Melillo, M. et al. "Structural Characteristics of Activated Carbons and Ibuprofen Adsorption Affected by Bovine Serum Albumin," Langmuir 20 (2004) 2837-2851.
Olton, D. et al. "Nanostructured calcium phosphates (NanoCaPs) for non-viral gene delivery: Influence of the synthesis parameters on transfection efficiency," Biomaterials 28 (2007) 1267-1279.
Panyam, J. et al. "Biodegradable nanoparticles for drug and gene delivery to cells and tissue," Advanced Drug Delivery Reviews 55 (2003) 329-347.
Parida, S.K. et al. "Adsorption of organic molecules on silica surface," Advances in Colloid and Interface Science 121 (2006) 77-110.
Rai, B. et al. "Novel PCL-based honeycomb scaffolds as drug delivery systems for rhBMP-2," Biomaterials 26 (2005) 3739-3748.
Sahai, N. et al. "Molecular Orbital Study of Apatite (Ca5(P04)pH) Nucleation at Silica Bioceramic Surfaces," J. Phys. Chem. B 104 (2000) 4322-4341.
Schmidt, H.T. et al. "Assembly of Aqueous-Cored Calcium Phosphate Nanoparticles for Drug Delivery," Chem. Mater. 2004, 16, 4942-4947.
Schmidt, S.M. et al. "Surfactant based assembly of mesoporous patterned calcium phosphate micron-sized rods," Microporous and Mesoporous Materials 94 (2006) 330-338.
Seeherman, H. et al. "Delivery of bone morphogenetic proteins for orthopedic tissue regeneration," Cytokine & Growth Factor Reviews 16 (2005) 329-345.
Slowing, 1.1. et al. "Mesoporous Silica Nanoparticles for Drug Delivery and Biosensing Applications," Adv. Funct. Mater. 17 (2007) 1225-1236.
Vallet-Regi, M. et al. "A New Property of MCM-41: Drug Delivery System," Chem. Mater. 13 (2001) 308-311.
Wan, X. et al. "Preparation and in vitro bioactivities of calcium silicate nanophase materials," Materials Science and Engineering C 25 (2005) 455-461.
Weissbart, E.J. et al. "Wallastonite: Incongruent dissolution and leached layer formation," Geochimica et Cosmochimica Acta 64 (2000) 4007-4016.
Xia, W. et al. "Well-ordered mesoporous bioactive glasses (MBG): A promising bioactive drug delivery system," Journal of Controlled Release 110 (2006) 522-530.
Xu, Z.P. et al. "Inorganic nanoparticles as carriers for efficient cellular delivery," Chemical Engineering Science 61 (2006) 1027-1040.
Xue, W. et al. "In vivo evaluation of plasma-sprayed wollastonite coating," Biomaterials 26 (2005) 3455-3460.
Saravanapavan, Journal of Non-Crystalline Solids, 318, pp. 1-13, 2003.
Saravanapavan, Journal of Non-Crystalline Solids, 318, pp. 14-26, 2003.
Saravanapavan, Bio-Medical Materials and Engineering, 14, 2004.
Office Action in U.S. Appl. No. 12/211,005 issued Jul. 9, 2010, 11 pages.
Office Action in U.S. Appl. No. 12/211,005 issued Mar. 23, 2011, 14 pages.
Office Action in U.S. Appl. No. 12/211,005 issued Apr. 10, 2014, 9 pages.
Office Action in U.S. Appl. No. 11/675,006 issued Jul. 28, 2009, 6 pages.
Office Action in U.S. Appl. No. 11/675,006 issued May 10, 2010, 8 pages.

* cited by examiner (a)  (b)  (c)

(d)  (e)

(a) (b) (c)

(d) (e)

Figure 6: Porous TCP structures with 300 micron porosity, but different volume fraction porosity.

(a): Zn  (b):

RESORBABLE CERAMICS WITH CONTROLLED STRENGTH LOSS RATES

CROSS-REFERENCE TO RELATED APPLICATIONS

This application is a divisional application of U.S. patent application Ser. No. 12/298,012, filed 21 Oct. 2008, which is the United States Nationalization, under 35 U.S.C. 371, of International Application No. PCT/US2007/067444, filed 25 Apr. 2007, and claims the benefit of priority to U.S. Provisional Patent Application Ser. No. 60/794,698, filed 25 Apr. 2006 and entitled "RESORBABLE CERAMICS WITH CONTROLLED STRENGTH LOSS RATES," which is incorporated herein by reference in its entirety.

STATEMENT REGARDING FEDERALLY-SPONSORED RESEARCH

This invention was made with government support under CTS-0134476 awarded by the National Science Foundation, under N00014-04-1-0644 and N00014-05-1-0583 awarded by the Office of Naval Research, and under R01 EB007351 awarded by National Institute of Biomedical Imaging and Bioengineering of the National Institutes of Health. The government has certain rights in this invention.

FIELD OF THE INVENTION

Aspects of the invention described herein relate generally to bone grafting materials, and more particularly to novel compositions and methods comprising the use of resorbable ceramics based on calcium phosphates (CaP) with different dopants to facilitate controlled strength loss rates within a select period of time.

BACKGROUND

Musculoskeletal Disorders and Bone Defects.

Musculoskeletal disorders and bone deficiencies have been established as among the most important human health concerns, costing society an estimated $254 billion annually, and afflicting, for example, 1 out of 7 Americans. Such conditions are prevalent in the aged population, and the number of individuals presenting with a bone deficiency is anticipated to increase as the population ages (the number of people over age 50 will double between 1990 and 2020). Bone defects are frequently caused by trauma, disease, developmental deformity, and tumor removal.

Need for Improved Treatment Methodology.

There is a critical need for improved treatment methodology for bone disorders (Ducheyne, 1999). Currently, repairing such bone sites involves various medical surgical techniques, including the use of autogenous grafts, allogenous grafts, internal and external fixation devices, electrical stimulation, and replacement implants. Although effective in many cases, such existing technologies have numerous difficulties and disadvantages. Moreover, current cell culture methods for tissue-engineered bone grafting materials produce weakly organized sheets of cells, and these constructs cannot withstand the mechanical forces present in vivo (Vandenburgh, 1991).

Need for Improved Bone Grafting Material.

Currently the gold standard for the bone reconstruction and guided bone regeneration (GBR) applications is the autogeneous bone graft (e.g., Yaszemski, 1996; Buser, 1994), and the use of biodegradable bone substitute would be desirable in such applications to avoid the second site surgery for autograft harvesting. There is therefore a pronounced need for a material that can be implanted into individuals to restore their lost structure and function, and particularly a need for a bone grafting material that will permit rapid cell growth and maturation within, while providing the initial biomechanical support required for ambulatory function. This material must accomplish this objective while slowly transferring this function to the developing tissue (Burg, 2000). Lack of such a material prevents clinical applications to provide immediate restoration of functional load bearing (Lanza, 1997).

Bioresorption and Tissue Restoration; Use of Calcium Phosphate Bioresorbable Ceramics.

Although fabrication of high-strength materials which can replace lost tissue function temporarily is known in the art, the ideal material for permanent implant application must be capable of not merely replacing tissue function, but of restoring lost tissues. Therefore, such an ideal material be bioresorbable to allow the native tissues to gradually replace the implanted material with host bone. Although calcium phosphate bioresorbable ceramics are known in the art, little work has been reported on improving mechanical properties of these materials for hard tissue engineering applications. Three factors that cause in vivo resorption of calcium phosphate bioceramics are: (i) physiologic dissolution, which depends on pH and composition of calcium phosphate; (ii) physical disintegration, which may be due to biochemical attack at the grain boundaries or due to high porosity; and (iii) biological factors such as phagocytosis.

Individualized Applications and the Lack of Adequate Resorbable Materials.

As shown in TABLE 1 below, the mechanical properties of bone depend substantially upon their physiologic function, and the desired rate of biodegradation of synthetic materials will ideally depend on the application site and the particular patients needs. For example, in craniomaxillofacial applications such as localized ridge augmentation, a relatively rapid biodegradation is desirable, particularly prior to dental implant placement because new bone should ideally form while leaving no residual particles to interfere with preparation of the implant bed at the time of surgery (Yaszemski, 1996). By contrast, for spinal grafting, a slow biodegradation and strength loss is desirable until new bone grows. Bioactive calcium phosphate ceramics and bioactive glasses have recently been considered as candidate biomaterials for craniomaxillofacial applications. However, for $\beta$-tri calcium phosphate ($\beta$-TCP), the biodegradation has been reported to be incomplete even after 9.5 months after grafting in the human mandible, and histological examination of these biopsies revealed that 34% of the biopsy consisted of mineralized bone tissue and 29% of remaining $\beta$-TCP (Zerbo 2001). Likewise, in the case of bioglass 45S5, the particles have been reported to resorb over 1-2 years, by dissolution rather than osteoclastic activities (Tadjoedin 2002). Moreover, currently, there is no ideal synthetic material for spinal grafting applications. Such examples illustrate the need for development of biodegradable ceramic materials that will act as a scaffold and support bone remodeling in an time frame appropriate to the particular application. Ideally, such desired materials should degrade in a controlled fashion into non-toxic products that the body can metabolize or excrete via normal physiological mechanisms (Yaszemski 1996).

TABLE 1

Properties of Human Bone (Yamada, 1970).

| Tissue | Direction | Modulus of elasticity (GPa) | Tensile Strength (MPa) | Compressive Strength (MPa) |
|---|---|---|---|---|
| Femur | Longitudinal | 17.2 | 121 | 167 |
| Tibia | Longitudinal | 18.1 | 140 | 159 |
| Fibula | Longitudinal | 18.6 | 146 | 123 |
| Humerus | Longitudinal | 17.2 | 130 | 132 |
| Radius | Longitudinal | 18.6 | 149 | 114 |
| Ulna | Longitudinal | 18.0 | 148 | 117 |
| Cervical Vertebrae | Longitudinal | 0.23 | 3.1 | 10 |
| Lumbar Vertebrae | Longitudinal | 0.16 | 3.7 | 5 |
| Spongy Bone | | 0.09 | 1.2 | 1.9 |
| Skull | Tangential | — | 25 | — |
| Skull | Radial | — | — | 97 |

Extracellular Matrix Composition of Bone; Presence of Trace Elements.

The composition of the extracellular matrix of human bone is well known, comprising: approximately 69 wt % substituted carbonate-hydroxylapatite mineral; 22 wt % organic substances; and 9 wt % water (e.g., LeGeros, 1990; Suchanek, 1998; Park, 1984). Apart from Ca and P ions, the extracellular matrix also comprises $Na^+$, $Mg^{2+}$, $K^+$, $CO_3^{2-}$, $F^-$, $Cl^-$, and trace amounts of $Zn^{2+}$, $Fe^{3+}$, $Cu^{2+}$, $Pb^{2+}$ and $Sr^{2+}$. Typical crystallite sizes are in the range of 25 nm thick (40-120 nm wide and 0.16 to 1 micron long), and the 'ignition' product results in hydroxyapatite (HAp), CaO and β-TCP phases (LeGeros, 1991). The Ca to P ratio varies in hone, enamel and dentine, where hone has the highest Ca (1.71:1 of Ca:P), and dentine has the lowest (1.61:1 of Ca:P) (Suchanek, 1998). A small change in chemical composition in CaP based ceramics has been shown to significantly alter sintering characteristics and related properties. Adding small amounts of metal ions to these materials can also alter their mechanical and biological properties. Such trace elements effect overall performance of human bone, and it is thus important to incorporate these them in to implants because the biocompatibility of 'apatites' is closely dependent on their composition (Knowles, 1996).

Sodium (Na) and fluorine (F) ions are both found to occur naturally in human bone tissue. The extent to which Na and F are substituted in an apatite-based dental restoration will likely affect apatite solubility and the ability of the restoration to resist further acidic challenges. The addition of sodium to calcium phosphate ceramics has been reported to induce the formation of other phases such as β—$Na_2CaP_2O_7$ and $Na_3Ca_6(PO_4)_5$. These phases are known to have high bioresorbability and degradation rates in physiological media. Fluorine is also a common ion in human bone tissue, but is found in particularly higher concentrations in tooth enamel. The presence of fluorine in calcium phosphates can result in formation of fluorapatite (FAP) $Ca_{10}(PO_4)_6F_2$. Studies have indicated that fluorine can promote bone regeneration and also lead to lower solubility/degradation of calcium phosphate ceramics due to its acid resistivity.

Calcium oxide (CaO) is a naturally existing phase in bone tissue. The addition of CaO will increase the calcium to phosphorous ratio in the TCP ($Ca_3(PO_4)_2$), which plays a significant role in the degradation rate of particular calcium phosphate ceramics. Moreover, Kalita et al. found the compression strength of HAP to increase when CaO was supplemented as a sintering additive.

Resorption of Bone Materials and Calcium Phosphate Bioceramics.

Calcium phosphate (CaP) ceramics are considered among the most promising materials for bone tissue engineering because of their bone-like composition and mechanical properties. Hydroxyapatite and tricalcium phosphate are used in orthopedic, maxillofacial, and dental implant surgery either as a temporary support scaffold or in a particulate paste to fill bone defects. Biodegradation properties of these materials allows for bone tissue engineering applications, because they can promote apatite formation and simultaneously deliver growth factors for osteoinduction. Significantly, however, the process of resorption of calcium phosphate bioceramics is quite different from that for bone, essentially because of different textures. Bone mineral crystals possess a very large surface area because they have grown in an organic matrix and have very loose crystal-to-crystal bonds, resulting in a relatively homogeneous resorption by osteoclasts. By contrast, calcium phosphate bioceramics present a low surface area and have strong crystal-to-crystal bonds. Resorption takes place in two steps: the disintegration of the particles into crystals, and the dissolution of the crystals (Heughebaert, 1988).

Use of Tricalcium Phosphate (TCP; $Ca_3(PO_4)_2$).

Tricalcium phosphate (TCP; $Ca_3(PO_4)_2$) is a CaP based synthetic material that forms a bioactive bond with natural bone. Compared with hydroxyapatite, TCP has a lower calcium-to-phosphorous ratio, which increases the degradation rate when the ceramic is placed in a biological environment. TCP degrades in the body and the products are resorbed by the surrounding tissue. Therefore, such matrix absorption may be used to expose surfaces to tissue or to release admixed materials such as antibiotics or growth factors in controlled drug release. Among several clinical applications of TCP, two that are currently being researched are posterior spinal fusion and dental augmentation. Improving mechanical properties, bioactivity, and osteoconduction might also trigger faster bone in-growth in dental applications.

In summary, therefore, mechanical properties of particular hones depend substantially upon their respective physiologic functions, and optimally the rate of biodegradation of synthetic materials used in particular hone replacement applications should reflect the respective application site and patients needs. For particular applications (e.g., craniomaxillofacial), a relatively rapid biodegradation is desirable, whereas a slow biodegradation and strength loss is desirable for other applications (e.g., spinal grafting).

There is, therefore, a pronounced need in the art for further improved CaP based ceramics. There is a pronounced need for individualized applications of bone replacement/restoration materials. There is a pronounced need for bone replacement/restoration materials that can provide for time-varying mechanical properties while allowing for complete dissolution over an appropriate time frame. There is a pronounced need for bone replacement/restoration materials that reduce or eliminate long-term biocompatibility concerns.

SUMMARY OF EXEMPLARY ASPECTS OF THE INVENTION

Particular aspects of the present invention provide novel compositions and methods involving calcium phosphate (CaP) ceramics, and ternary and quaternary compositions with $Ag_2O$ and $TiO_2$ in Tricalcium phosphate (TCP; $Ca_3(PO_4)_2$) doped with NaF and CaO. The influence and inventive use of these dopants on mechanical properties of TCP, and on degradation kinetics is herein disclosed.

Particular aspects provide calcium phosphate compositions ($Ca_x(PO_4)_y$, where x=1 or more, and y=1 or more) and hydroxylated variants thereof, and novel uses for these compositions.

According to certain aspects, the resorption characteristics of these materials provides for their use as grafts for repair or reconstruction of tissue defects by providing for a controllable space for tissue growth during healing.

Additional aspects, therefore, provide a three-dimensional, interconnected tissue scaffold upon which tissue cells may grow and proliferate. The inventive scaffold material composition provides a controlled degradation rate such that the developing tissues may be exposed to the normal range of mechanical forces present in the body, while slowly being degraded, thus allowing for full restoration of the native tissue. The design of optimal scaffold compositions therefore allows for routine, predictable use of tissue engineered replacements, to provide for rapid patient healing and lower health care cost.

Particular embodiments provide bone scaffold structures comprising CaP ceramics containing dopant elements, wherein the degradation rate of the scaffold material is tailored, through the specific combinations and/or concentration of Ca:P ratio and/or dopant(s), to match the growth rate of the tissues being supported by the scaffold.

In certain aspects, the scaffold material degradation rate closely matches the growth rate of new tissue, and such materials can be used in inventive methods to avoid the production of a gap at the tissue-scaffold interface.

In additional aspects, the inventive material compositions provide for a gradual offloading of biomechanical forces onto the developing tissues, and such materials can be used in inventive methods to promote maturation of mechanically viable tissues.

In further aspects, advantages of controlled strength loss CaPs provide novel methods for: compositional matching/similarity with a particular tissue, (e.g., bone, or a particular bone); exceptional biocompatibility; high initial strength (not achieved with prior art polymer-based resorbable materials); and provision of mechanical strength and stiffness properties comparable to that of natural bone.

Additional embodiments provide a method for tailoring of the mechanical properties of the scaffold material through alteration of the dopant element(s) and their respective concentrations within the CaP scaffold.

Additional embodiments compositions and methods for altering properties of the scaffold material to facilitate controlled delivery and/or release of drugs or growth factors that may be incorporated into the surface and/or matrix of the scaffold material.

Particular aspects provide bioresorbable and biocompatible composition for bioengineering, restoring or regenerating tissue or musculoskeletal tissue, comprising: a three-dimensional porous or non-porous scaffold material comprising a calcium phosphate-based ceramic, the ceramic having at least one dopant included therein selected from the group consisting of metal salts with metal ions and metal oxide dopants, wherein the composition is sufficiently biocompatible to provide for a cell or tissue scaffold, and resorbable at a controlled resorption rate, to control mechanical strength and strength degradation, dependent upon the dopant composition, under body, body fluid or simulated body fluid conditions. In certain embodiments, the at least one dopant is selected from the group consisting of $Zn^{2+}$, $Mg^{2+}$, $Si^{2+}$, $Na^+$, $K^+$, $Sr^{2+}$, $Cu^{2+}$, $Fe^{3+}/Fe^{2+}$, $Ag^+$, $Ti^{4+}$, $CO_3^{2-}$, $F^-$, MgO, ZnO, NaF, KF, $FeO/Fe_2O_3$, SrO, CuO, $SiO_2$, $TiO_2$, $Ag_2O$ and $CaCO_3$, present in a single-element or multi-element amount between 0 and about 10 wt %, from about 0.5 to about 5 wt %, from about1 to about 3 wt %, from about 2 to about 7 wt %, from about 3 to about 7 wt %, from about 4 to about 7 wt %. In particular aspects, the at least one dopant is present in an amount sufficient to maintain the compressive strength of the material at about 30% of original or higher, 40% of original or higher, 50% of original or higher, 60% of original or higher, 70% of original or higher, 80% of original or higher, 90% of original or higher, in each case, for a period of at least 6, at least 7, least 8, at least 9, at least 10, at least 11 or at least 12 months under body, body fluid or simulated body fluid conditions, to provide for a slow-degrading composition. In certain embodiments, the at least one dopant is present in an amount sufficient to reduce the compressive strength of the material to about 90%, or less than 90%, 80%, or less than 80%, 70%, or less than 70%, 60%, or less than 60% or 50%, or less than 50% of original, in each case, within a period of about 3 months, about 4 months, about 5 months or about 6 months under body, body fluid or simulated body fluid conditions, to provide for a fast-degrading composition. In particular aspects, the at least one dopant is selected from the group consisting of SrO, ZnO, $TiO_2$, MgO and $SiO_2$ dopants, present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %. In certain implementations, the ceramic comprises a multi-element dopant comprising at least two dopants selected from the group consisting of $Zn^{2+}$, $Mg^{2+}$, $Si^{2+}$, $Na^+$, $K^+$, $Sr^{2+}$, $Cu^{2+}$, $Fe^{3+}/Fe^{2+}$, $Ag^+$, $Ti^{4+}$, $CO_3^{2-}$, $F^-$, MgO, ZnO, NaF, KF, $FeO/Fe_2O_3$, SrO, CuO, $SiO_2$, $TiO_2$, $Ag_2O$ and $CaCO_3$, present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %. In particular embodiments, the ceramic comprises at least one dopant ions and/or oxides present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %.

In particular embodiments of the compositions, the calcium phosphate comprises at least one single or mixed phase calcium phosphate material having the formula ($Ca_x(PO_4)_y$, where x=1 or more, and y=1 or more), or hydroxylated variants thereof. the calcium phosphate comprises at least one single or mixed phase calcium phosphate material having calcium to phosphate ratio (Ca/P) in a range from about 1.4:1 to about 1.7:1, or from about 1.0:1 to about 2.0:1. In particular embodiments, the calcium to phosphate ratio is about 1.5:1, or about 1.67:1. In particular implementations, the calcium phosphate-based ceramic comprises at least one of tricalcium phosphate (TCP; $Ca_3(PO_4)_2$) and Hydroxyapitite (HAp; $Ca_{10}(PO_4)_6(OH)_2$).

In particular embodiments of the compositions, the scaffold material comprises a plurality of ceramic particles, and further comprises an open and interconnected porous network. In certain aspects, the open and interconnected porous network is between and among said ceramic particles, and the pore size of the open and interconnected porous network is within a restricted or controlled range established during formation of the scaffold material. In certain embodiments, the restricted or controlled range of pore size comprises a microporous or macroporous pattern having pore sizes in the range of about 10 μm to about 5 mm, or comprises nanoscale or microscale pores ranging from about 10 nm to about 500 µm in diameter, or from about 1 nm to about 1 µm.

The composition of claim 1, wherein the scaffold material comprises dense to solid structures, or porous structures having internal cavities with sizes varying from nano-scale to larger sizes, or micro porous structures, wherein the core of the bulk scaffold material is comprised of a geometric pattern of material with voided areas or low density structures with a quasi-solid exterior.

In particular embodiments of the compositions, the exterior walls of the scaffold material comprises meso-scale pores, wherein the pores open to voided areas within the core of the material.

Particular embodiments of the compositions further comprise at least one chemical, drug, growth factor or biological agent deposited, incorporated into, or stored within and/or on a surface of the scaffold material or within one or more pores thereof to operatively provide for release or controlled release of the agent to facilitate bioengineering, restoring or regenerating bone or other tissue. In certain aspects, the at least one agent comprises at least one selected from the group consisting of antibiotics, antimicrobial agents, growth factors, osteoinductive growth factors, drugs, polypeptides and proteins. In particular embodiments, the at least one agent is selectively activatable and/or releasable at set times by the application of at least one, electrical, magnetic, chemical or photochemical triggering event. In certain aspects, the at least one chemical, electrical, magnetic or photochemical triggering event is at least one selected from the group consisting of chemical ingestion or infusions, exposure to UV light, ultrasound, magnetic fields, and electric current.

In certain embodiments, the composition is a coating material.

Preferably, the biocompatibility is sufficient to provide for bioengineering, restoring or regenerating bone or other tissue in the body of a human or other vertebrate or animal. In certain implementations, the compositions are useful for at least one of dental and orthopedic implants, craniomaxillofacial applications, and spinal grafting, and said composition is suitable to promote bone in-growth and repair.

Particular aspects of the compositions provide disks, solids or pourous scaffolds.

Additional aspects provide a method for making a bioresorbable and biocompatible composition for bioengineering, restoring or regenerating bone or other tissue according to any one of claims 1-22, comprising at least one of sintering of the calcium phosphate-based ceramic, and the use of synthesized nanopowders of the calcium phosphate-based ceramic. In particular aspects of the method, the material properties of the composition are selectively modulated by using at least one of sintering processes to reduce grain sizes, and synthesized nanopowders to further reduce grain size for increased strength and hardness and/or improved cell materials interactions. Certain embodiments of the method further comprise depositing, incorporating into, or storing a chemical, drug, growth factor or biological agent within and/or on a surface of the scaffold material or within one or more pores thereof to operatively provide for release or controlled release of the agent to facilitate bioengineering, restoring or regenerating bone or other tissue. In certain aspects, the at least one agent comprises at least one selected from the group consisting of antibiotics, antimicrobial agents, growth factors, osteoinductive growth factors, drugs, polypeptides and proteins. In particular embodiments, the at least one agent is selectively activatable and/or releasable at set times by the application of at least one chemical, electrical, magnetic or photochemical triggering event. In certain implementations, the at least one chemical, electrical, magnetic or photochemical triggering event is at least one selected from the group consisting of chemical ingestion or infusions, exposure to UV light, ultrasound, magnetic fields and electric current.

Further aspects provide a method for tissue or musculoskeletal tissue engineering, comprising placement, under body fluid or simulated body fluid conditions, a bioresorbable and biocompatible composition as described herein for bioengineering, restoring or regenerating bone and/or other tissue, wherein the bone and/or other tissue is, at least in part, bioengineered, restored or regenerated. In particular aspects of the method, bioengineering, restoring or regenerating bone or another tissue is in vitro or ex vivo, comprising placement under simulated body fluid conditions or body fluid conditions. In certain embodiments of the method, bioengineering, restoring or regenerating bone and/or other tissue is in vivo, comprising placement under body fluid conditions or body conditions. In particular aspects, the three-dimensional tissue scaffold comprises an open interconnected porous network to facilitate at least one of cell adhesion, growth, spreading, metabolism, proliferation and differentiation, with temporally controlled strength loss of the scaffold material such that the tissue being bioengineered, restored or regenerated is subjected to a range of mechanical forces normally associated with such tissues. In particular embodiments of the method, the compositions are used for dental and orthopedic implants, craniomaxillofacial applications and spinal grafting, and said composition is suitable to promote bone in-growth and repair.

Yet further aspects provide a method for providing a coated material for use in bioengineering, restoring or regenerating tissue or musculoskeletal tissue, comprising: obtaining a substrate material and coating the material with a composition according to any one of claims 1-22, to provide at material suitable for use in bioengineering, restoring or regenerating tissue or musculoskeletal tissue.

Yet additional embodiments provide a method for tissue or musculoskeletal tissue engineering, comprising placement, under body fluid or simulated body fluid conditions, a coated material as describe herein, wherein the bone and/or other tissue is, at least in part, bioengineered, restored or regenerated.

DETAILED DESCRIPTION OF THE INVENTION

Figure 1:
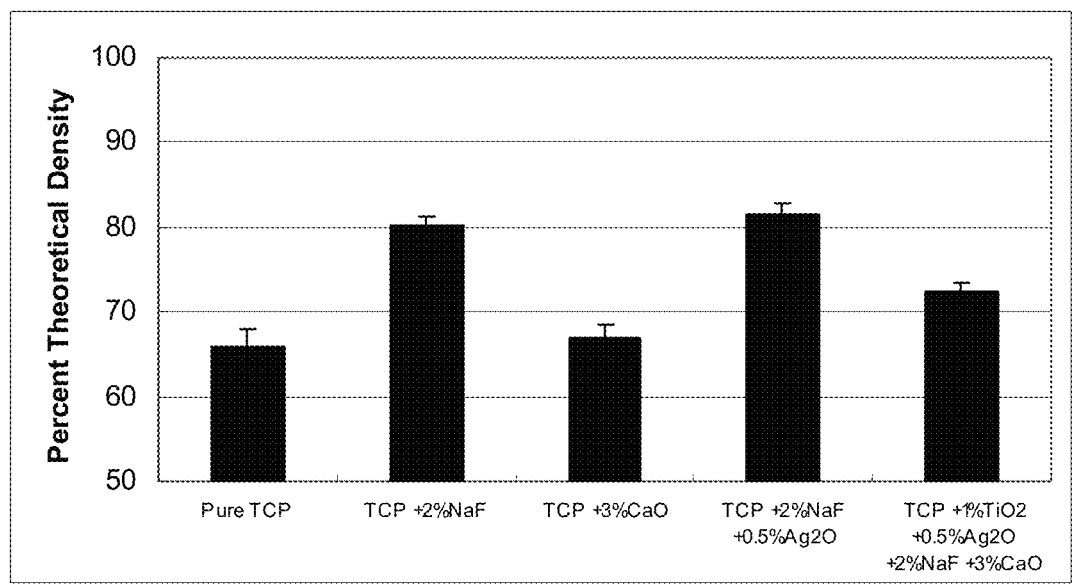
FIG. 1 shows, according to particular exemplary aspects of the present invention, normalized bulk densities of sintered compression samples.

Particular aspects of the present invention provide bone replacement materials (e.g., three-dimensional tissue scaffolds), comprising CaP-based ceramics with inclusion of multi-element dopants, to provide for biocompatible scaffolds having controlled degradation rates. These inventive porous, interconnected scaffolds allow for and facilitate tissue (e.g., bone) cells to grow and proliferate, with temporally controlled strength loss of the scaffold material, such that the developing tissues may undergo (e.g., be exposed to) a range (e.g., the normal range) of mechanical forces associated, or normally associated with such tissues.

Particular inventive compositions include, but are not limited to those comprising: calcium phosphates (compositions may be varied from Ca:P of 1:1 to 2:1), and dopants of ions including, (e.g., $Zn^{2+}$, $Mg^{2+}$, $Si^{2+}$, $Na^+$, $K^+$, $Sr^{2+}$, $Cu^{2+}$, $Fe^{3+}/Fe^{2+}$, $Ag^+$, $Ti^{4+}$, $CO_3^{2-}$, $F^-$), and/or dopant metal oxides (e.g., MgO, ZnO, NaF, KF, $FeO/Fe_2O_3$, SrO, CuO, $SiO_2$, $TiO_2$, $Ag_2O$, $CaCO_3$ etc.), and/or various combinations thereof. In particular aspects, the CaP material comprises one or more dopant ions and/or oxides present in the concentration ranging from 0 to 10% by weight percentage (wt %). In particular embodiments, the CaP compositions comprise at least one dopant selected from the group consisting of SrO, ZnO, $TiO_2$, MgO and $SiO_2$ dopants, to provide materials for modulating cell-materials interactions and for use in modifying strength degradation behavior of the materials.

Various art-recognized methods for the synthesis of these materials are available, and include, but are not limited to, sintering processes and the use of synthesized nanopowders. Particular methods may be selected to selectively modulate material properties; for example, sintering processes may be utilized to reduce grain sizes, and synthesized nanopowders may be used to further reduce grain size for increased strength and hardness.

In particular aspects, implementation of these materials takes the form of dense to solid structures, or porous structures having internal cavities of varying sizes from nano-scale and larger.

Additional embodiments comprise micro porous structures, wherein the core of the bulk material is comprised of a geometric pattern of material with voided areas to provide for low density structures comprising a quasi-solid exterior.

Yet additional embodiments comprise the incorporation of meso-scale pores in the exterior walls of the bone replacement materials, wherein the pores open to voided areas within the core of the material.

Further embodiments comprise the incorporation or storage of agents (e.g., chemical and/or biological agents) within the micro (within the bulk material) and/or meso (on the surface of the material) porous structures surfaces, wherein the agents produce effects beneficial for biological applications (e.g. antibiotics, growth factors, drugs, amino acid sequences).

Further embodiments include storage of such chemical agents within the structure of the scaffold material wherein the agents can be selectively activated and/or released at set times (e.g., via the application of specific chemical or photochemical triggering).

Preferred Exemplary Embodiments

Particular aspects provide bioresorbable and biocompatible composition for bioengineering, restoring or regenerating tissue or musculoskeletal tissue, comprising: a three-dimensional porous or non-porous scaffold material comprising a calcium phosphate-based ceramic, the ceramic having at least one dopant included therein selected from the group consisting of metal salts with metal ions and metal oxide dopants, wherein the composition is sufficiently biocompatible to provide for a cell or tissue scaffold, and resorbable at a controlled resorption rate, to control mechanical strength and strength degradation, dependent upon the dopant composition, under body, body fluid or simulated body fluid conditions. In certain embodiments, the at least one dopant is selected from the group consisting of $Zn^{2+}$, $Mg^{2+}$, $Si^{2+}$, $Na^+$, $K^+$, $Sr^{2+}$, $Cu^{2+}$, $Fe^{3+}/Fe^{2+}$, $Ag^+$, $Ti^{4+}$, $CO_3^{2-}$, $F^-$, MgO, ZnO, NaF, KF, $FeO/Fe_2O_3$, SrO, CuO, $SiO_2$, $TiO_2$, $Ag_2O$ and $CaCO_3$, present in a single-element or multi-element amount between 0 and about 10 wt %, from about 0.5 to about 5 wt %, from about1 to about 3 wt %, from about 2 to about 7 wt %, from about 3 to about 7 wt %, from about 4 to about 7 wt %. In particular aspects, the at least one dopant is present in an amount sufficient to maintain the compressive strength of the material at about 30% of original or higher, 40% of original or higher, 50% of original or higher, 60% of original or higher, 70% of original or higher, 80% of original or higher, 90% of original or higher, in each case, for a period of at least 6, at least 7, least 8, at least 9, at least 10, at least 11 or at least 12 months under body, body fluid or simulated body fluid conditions, to provide for a slow-degrading composition. In certain embodiments, the at least one dopant is present in an amount sufficient to reduce the compressive strength of the material to about 90%, or less than 90%, 80%, or less than 80%, 70%, or less than 70%, 60%, or less than 60% or 50%, or less than 50% of original, in each case, within a period of about 3 months, about 4 months, about 5 months or about 6 months under body, body fluid or simulated body fluid conditions, to provide for a fast-degrading composition. In particular aspects, the at least one dopant is selected from the group consisting of SrO, ZnO, TiO$_2$, MgO and SiO$_2$ dopants, present in a single-element or multi-element amount between 0 and about 10 wt %, from about 0.5 to about 5 wt %, from about1 to about 3 wt %, from about 2 to about 7 wt %, from about 3 to about 7 wt %, from about 4 to about 7 wt %. In certain implementations, the ceramic comprises a multi-element dopant comprising at least two dopants selected from the group consisting of Zn$^{2+}$, Mg$^{2+}$, Si$^{2+}$, Na$^+$, K$^+$, Sr$^{2+}$, Cu$^{2+}$, Fe$^{3+}$/Fe$^{2+}$, Ag$^+$, Ti$^{4+}$, CO$_3^{2-}$, F$^-$, MgO, ZnO, NaF, KF, FeO/Fe$_2$O$_3$, SrO, CuO, SiO$_2$, TiO$_2$, Ag$_2$O and CaCO$_3$, present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %. In particular embodiments, the ceramic comprises at least one dopant ions and/or oxides present in a single-element or multi-element amount between 0 and about 10 wt %, from about 0.5 to about 5 wt %, from about1 to about 3 wt %, from about 2 to about 7 wt %, from about 3 to about 7 wt %, from about 4 to about 7 wt %.

In particular embodiments of the compositions, the calcium phosphate comprises at least one single or mixed phase calcium phosphate material having the formula (Ca$_x$(PO$_4$)$_y$, where x=1 or more, and y=1 or more), or hydroxylated variants thereof. the calcium phosphate comprises at least one single or mixed phase calcium phosphate material having calcium to phosphate ratio (Ca/P) in a range from about 1.4:1 to about 1.7:1, or from about 1.0:1 to about 2.0:1. In particular embodiments, the calcium to phosphate ratio is about 1.5:1, or about 1.67:1. In particular implementations, the calcium phosphate-based ceramic comprises at least one of tricalcium phosphate (TCP; Ca$_3$(PO$_4$)$_2$) and Hydroxyapitite (HAp; Ca$_{10}$(PO$_4$)$_6$(OH)$_2$).

In particular embodiments of the compositions, the scaffold material comprises a plurality of ceramic particles, and further comprises an open and interconnected porous network. In certain aspects, the open and interconnected porous network is between and among said ceramic particles, and the pore size of the open and interconnected porous network is within a restricted or controlled range established during formation of the scaffold material. In certain embodiments, the restricted or controlled range of pore size comprises a microporous or macroporous pattern having pore sizes in the range of about 10 μm to about 5 mm, or comprises nanoscale or microscale pores ranging from about 10 nm to about 500 in diameter, or from about 1 nm to about 1 μm.

The composition of claim 1, wherein the scaffold material comprises dense to solid structures, or porous structures having internal cavities with sizes varying from nano-scale to larger sizes, or micro porous structures, wherein the core of the bulk scaffold material is comprised of a geometric pattern of material with voided areas or low density structures with a quasi-solid exterior.

In particular embodiments of the compositions, the exterior walls of the scaffold material comprises meso-scale pores, wherein the pores open to voided areas within the core of the material.

Particular embodiments of the compositions further comprise at least one chemical, drug, growth factor or biological agent deposited, incorporated into, or stored within and/or on a surface of the scaffold material or within one or more pores thereof to operatively provide for release or controlled release of the agent to facilitate bioengineering, restoring or regenerating bone or other tissue. In certain aspects, the at least one agent comprises at least one selected from the group consisting of antibiotics, antimicrobial agents, growth factors, osteoinductive growth factors, drugs, polypeptides and proteins. In particular embodiments, the at least one agent is selectively activatable and/or releasable at set times by the application of at least one, electrical, magnetic, chemical or photochemical triggering event. In certain aspects, the at least one chemical, electrical, magnetic or photochemical triggering event is at least one selected from the group consisting of chemical ingestion or infusions, exposure to UV light, ultrasound, magnetic fields, and electric current.

In certain embodiments, the composition is a coating material.

Preferably, the biocompatibility is sufficient to provide for bioengineering, restoring or regenerating bone or other tissue in the body of a human or other vertebrate or animal. In certain implementations, the compositions are useful for at least one of dental and orthopedic implants, craniomaxillofacial applications, and spinal grafting, and said composition is suitable to promote bone in-growth and repair.

Particular aspects of the compositions provide disks, solids or pourous scaffolds.

Additional aspects provide a method for making a bioresorbable and biocompatible composition for bioengineering, restoring or regenerating bone or other tissue according to any one of claims 1-22, comprising at least one of sintering of the calcium phosphate-based ceramic, and the use of synthesized nanopowders of the calcium phosphate-based ceramic. In particular aspects of the method, the material properties of the composition are selectively modulated by using at least one of sintering processes to reduce grain sizes, and synthesized nanopowders to further reduce grain size for increased strength and hardness and/or improved cell materials interactions. Certain embodiments of the method further comprise depositing, incorporating into, or storing a chemical, drug, growth factor or biological agent within and/or on a surface of the scaffold material or within one or more pores thereof to operatively provide for release or controlled release of the agent to facilitate bioengineering, restoring or regenerating bone or other tissue. In certain aspects, the at least one agent comprises at least one selected from the group consisting of antibiotics, antimicrobial agents, growth factors, osteoinductive growth factors, drugs, polypeptides and proteins. In particular embodiments, the at least one agent is selectively activatable and/or releasable at set times by the application of at least one chemical, electrical, magnetic or photochemical triggering event. In certain implementations, the at least one chemical, electrical, magnetic or photochemical triggering event is at least one selected from the group consisting of chemical ingestion or infusions, exposure to UV light, ultrasound, magnetic fields and electric current.

Further aspects provide a method for tissue or musculoskeletal tissue engineering, comprising placement, under body fluid or simulated body fluid conditions, a bioresorbable and biocompatible composition as described herein for bioengineering, restoring or regenerating hone and/or other tissue, wherein the bone and/or other tissue is, at least in part, bioengineered, restored or regenerated. In particular aspects of the method, bioengineering, restoring or regenerating bone or another tissue is in vitro or ex vivo, comprising placement under simulated body fluid conditions or body fluid conditions. In certain embodiments of the method, bioengineering, restoring or regenerating bone and/ or other tissue is in vivo, comprising placement under body fluid conditions or body conditions. In particular aspects, the three-dimensional tissue scaffold comprises an open interconnected porous network to facilitate at least one of cell adhesion, growth, spreading, metabolism, proliferation and differentiation, with temporally controlled strength loss of the scaffold material such that the tissue being bioengineered, restored or regenerated is subjected to a range of mechanical forces normally associated with such tissues. In particular embodiments of the method, the compositions are used for dental and orthopedic implants, craniomaxillofacial applications and spinal grafting, and said composition is suitable to promote bone in-growth and repair.

Yet further aspects provide a method for providing a coated material for use in bioengineering, restoring or regenerating tissue or musculoskeletal tissue, comprising: obtaining a substrate material and coating the material with a composition according to any one of claims 1-22, to provide at material suitable for use in bioengineering, restoring or regenerating tissue or musculoskeletal tissue.

Yet additional embodiments provide a method for tissue or musculoskeletal tissue engineering, comprising placement, under body fluid or simulated body fluid conditions, a coated material as describe herein, wherein the bone and/or other tissue is, at least in part, bioengineered, restored or regenerated.

Specific exemplary manifestations of this invention are provided herein as illustrations and are not intended to limit the scope of the claimed invention, and various modifications will be apparent to one skilled in the art, based on the written description and enablement herein provided in view of the skill in the relevant art.

Example 1

Resorbable Ceramics in Tissue Engineering:
Influence of NaF and CaO Addition in TCP Example Overview and Summary.

Applicants have studied ternary and quaternary compositions with $Ag_2O$ and $TiO_2$ in TCP doped with NaF and CaO, with the aim of understanding the influence of these dopants on mechanical properties of TCP, as well as to study their degradation kinetics.

Tricalcium phosphate discs and cylinders were processed with compositions (i) pure TCP, (ii) 2.0 wt. % NaF, (iii) 3.0 wt. % CaO, (iv) binary of 2.0 wt. % NaF and 0.5 wt. % $Ag_2O$, and (v) quaternary 1.0 wt. % $TiO_2$, 0.5 wt. % $Ag_2O$, 2.0 wt. % NaF, and 3.0 wt. % CaO. Influences of these dopants on physical, mechanical, and biological properties were studied in comparison to pure TCP. Results showed that there is potential for improving these properties with the addition of metal ions without hindering the excellent biocompatibility of TCP. Ultimate compression strength increased from 70 to 130 MPa with the addition of NaF in pure TCP. Compression strength displayed a direct relationship to density. In-vitro cell culture tests showed that all compositions were non-toxic, and OPC1 cells attached and proliferated well on these TCP ceramics. Strength degradation in pure TCP began after 32 days in SBF, but for the doped compositions, strength loss was continuous up to 96 days. These results suggested that metal ion doped TCP can be tailored for different tissue engineering applications such as spinal fusion and dental augmentation to make TCP a more versatile biomaterial.

The presence of NaF in TCP improved densification and increased compression strength from 70 (±25) to 130 (±40) MPa. Addition of CaO had no influence on density or strength Human osteoblast cell growth behavior was studied using an osteoprecursor cell line (OPC 1) to assure that the biocompatibility of these ceramics was not altered due to the dopants.

For long-term biodegradation studies, density, weight change, surface microstructure, and uniaxial compression strength were measured as a function of time in a simulated body fluid (SBF). Weight gain in SBF correlated strongly with precipitation viewed in the inter-connected pores of the samples. After 3 months in SBF, all samples displayed a reduction in strength. NaF, CaO and the quaternary compositions maintained the most steady strength loss under SBF.

Materials and Processing Methods:

Compositions.

TCP ceramics reinforced with compositions of NaF, CaO, and $Ag_2O$ were processed into two different sample shapes via uniaxial powder compression: discs and cylinders. The compositions were prepared using high purity starting reagent grade materials which included synthetic β-tricalcium phosphate (TCP) nanocrystals (Berkely Advanced Biomaterials®, Inc., CA), sodium fluoride (NaF) 99+% and silver (1) oxide ($Ag_2O$) 99% (Sigma-Aldrich®, St. Louis, Mo.), titanium dioxide ($TiO_2$) (Dupont, Wilmington, Del.), and calcium oxide (CaO) (J. T. Baker, Phillipsburg, N.J.). Five different compositions were created from these dopants: (i) pure TCP, (ii) TCP with 2 wt. % NaF, (iii) TCP with 3 wt. % CaO, (iv) TCP with 2 wt. % NaF and 0.5 wt. % $Ag_2O$, and (v) TCP with a quaternary composition of 2 wt. % NaF, 3 wt. % CaO, 0.5 wt. % $Ag_2O$, and 1 wt. % $TiO_2$. Powders were mixed in 30 g batches in 125 mL polypropylene bottles, and the mixture was ball-milled at 120 rpm for 6 hours using YSZ grinding media.

Green discs and cylinders were fabricated from the processed powder. The discs were used for cell culture studies, and the cylinders were used for density, SBF, and compression studies. For discs, 500 mg of powder was uniaxially compressed at 200 MPa for 30 seconds in a cylindrical steel die with a diameter of 1.28 cm. These conditions led to a green disc thickness of 0.26 cm and a green density of 1.5 g/cm³. This is approximately 50% of the theoretical density of TCP, which is 3.07 g/cm³. For the cylinders, 1 g of powder was uniaxially compressed at a lower pressure of 100 MPa for 30 seconds, which led to green dimensions with a diameter of 0.625 cm and a height of 3 cm and a green density of 40% theoretical. This lower pressure was used in order to achieve proper sample removal from the die. Samples were sintered at 1250° C. for 4 hours in a Thermolyne high temperature muffle furnace in air.

Characterization Methods.

X-ray diffraction for phase analysis was carried out in a Philips Xpert® fully automated diffractometer (Eindhoven, The Netherlands) with Co K-α radiation. A setting of 35 kV and 35 mA was used with a step size of 0.02° (2θ). The peak positions, intensities, and d-spacing for samples with dopants were compared to those of pure TCP. For microstructural observation, sintered disc compacts of all five compositions were sputter-coated (Technics Hummer V, CA) with gold and observed under a scanning electron microscope (SEM) (Hitachi S570). The discs had distinct grain boundaries, and average grain size was calculated.

Cytotoxicity.

In vitro cytotoxicity test on dense TCP compacts was carried out using a modified human osteoblast (HOB) with an osteoprecursor cell line (OPC 1) (23). OPC1 cells were cultured in a standard medium made of McCoy's 5A (with 1-glutamine, without phenol red and sodium bicarbonate) from Sigma Chemical Co® supplemented with 5% fetal bovine serum, 5% bovine calf serum, 2.2 gram/liter sodium bicarbonate, 0.1 gram/liter penicillin, and 0.1 gram/liter streptomycin. Duplicate ceramic disc compacts were sterilized via autoclaving, and then seeded at a density of $2\times10^4$ with OPC-1 cells and cultured under standard aseptic conditions. Medium was changed every other day. Two discs of each composition were cultured for each of two durations: 5 and 11 days. At the end of the culture, samples were fixed, dehydrated, and stained to see morphology and attachment of the cells under SEM.

In order to characterize change in properties over time in a biological environment, sintered samples were soaked in a simulated body fluid (SBF) for 0, 32, 64, and 96 days. SBF is a saline solution which has a nearly identical salt composition to that of human blood plasma without the proteins. Five discs and five cylindrical samples of each composition were soaked in 10 ml SBF each at 37° C. for each duration period. Every four days, the used SBF was disposed of and replaced with freshly prepared SBF. Samples were taken out of SBF, gently rinsed twice in 100 ml distilled water, placed on a porous alumina plate, and dried in a muffle furnace at 200° C. for 7 days. The change in weight was calculated over the course of SBF treatment.

The ultimate compressive strength of as processed and SBF treated TCP was measured using a screw driven Instron with a constant crosshead speed of 0.33 mm/min. Compression samples had a diameter of 6 mm and a height between 14 and 18 mm. Ultimate compressive strength was calculated as maximum stress immediately prior failure. Fracture surfaces were collected and saved for fractography under SEM.

Results:

Densification:

Bulk densities of doped compacts were measured and compared to the compacts made with pure TCP. Density averages for each composition were calculated for both discs and cylinders, and then normalized to the theoretical density of TCP i.e., 3.07 g/cm$^3$.

FIG. 1 shows the normalized sintered bulk densities of the compression samples for each composition. TCP with NaF and TCP with NaF and Ag$_2$O had densities of 81% and 82%, respectively, which was an increase of 15% from that of pure TCP compacts. Addition of CaO to TCP had very little effect on density, while the quaternary composition showed a moderate increase.

Figure 2:
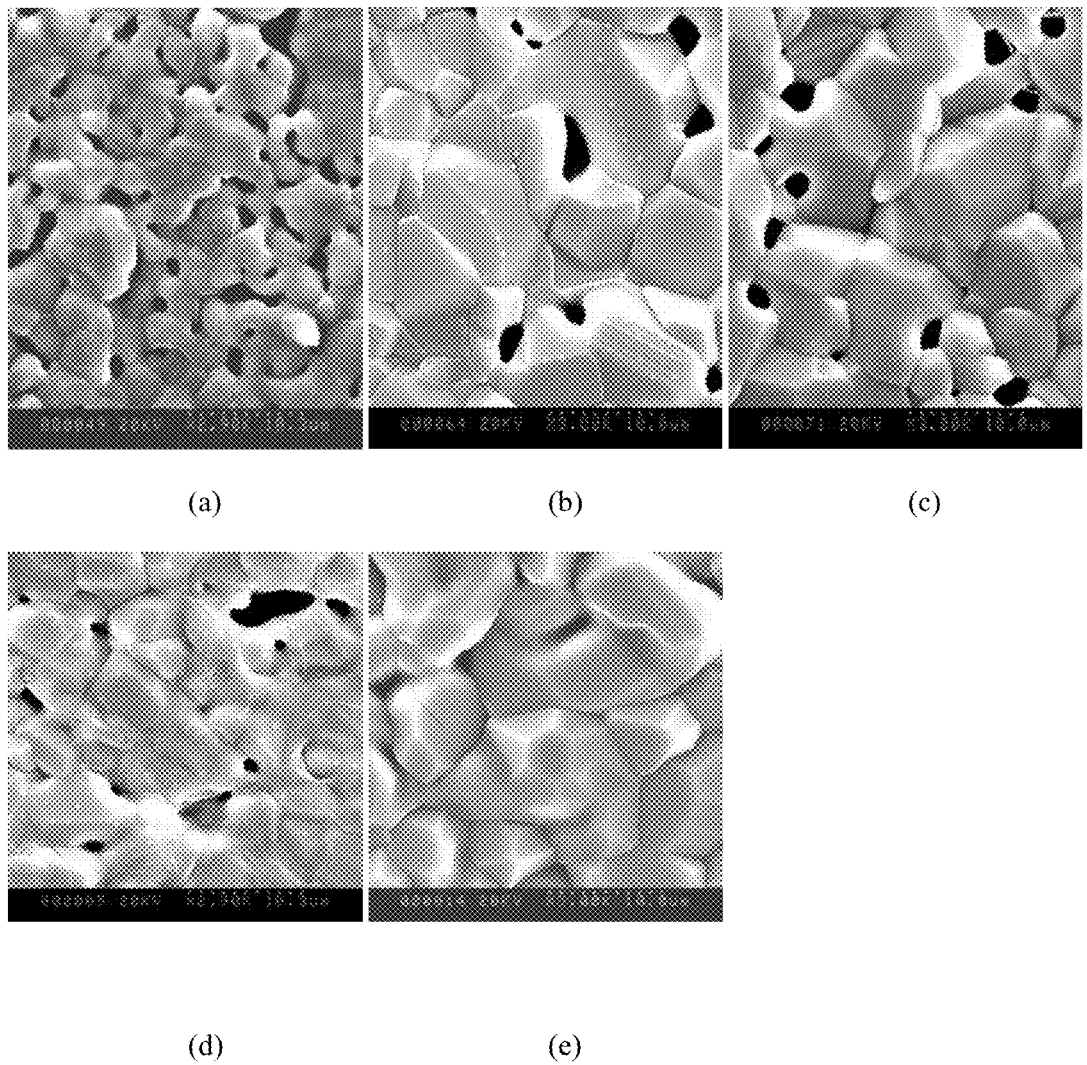
FIG. 2 shows, according to particular exemplary aspects of the present invention, SEM micrographs of disc sample surfaces. (a) pure TCP, (b) NaF doped, (c) CaO doped, (d) NaF—$Ag_2O$ doped, (e) quaternary.

FIG. 2 shows SEM micrographs for the top surfaces of the sintered samples. Both pure TCP and CaO doped samples show a relatively high amount of porosity, which explains the lower bulk densities for those compositions. Average grain size for pure TCP (3.01 μm) increased with the addition of both NaF (7.17 μm) and CaO (6.63 μm). This result suggest that during the sintering process, presence of these dopants caused significant grain growth in TCP compacts. Substitutional ions may cause extrinsic vacancies leading to a higher equilibrium concentration of vacancies in the bulk. This effect may alter the kinetics of grain boundary migration and increase grain growth during sintering (24).

Phase Analysis.

Figure 3:
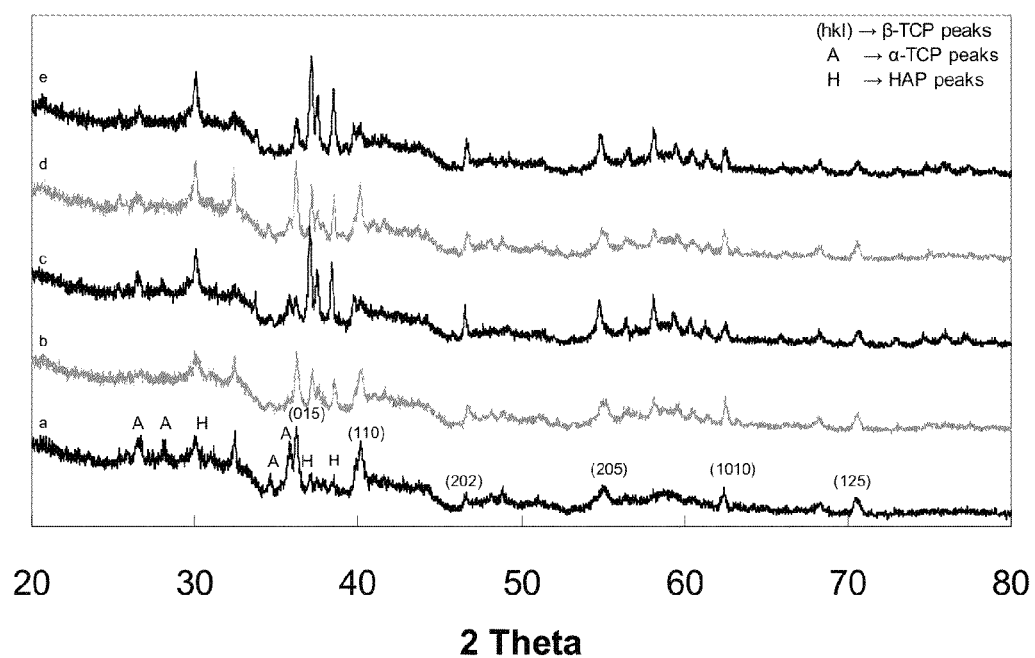
FIG. 3 shows, according to particular exemplary aspects of the present invention, XRD patterns for crushed sintered discs of (a) pure TCP, (b) TCP+NaF, (c) TCP+CaO, (d) TCP+NaF+$Ag_2O$, and (d) TCP+NaF+CaO+$Ag_2O$+$TiO_2$. (hkl) values for β-TCP peaks, (A) for α-TCP peaks, and (H) for HAP peaks.

FIG. 3 shows the XRD patterns of pure TCP, TCP with NaF, TCP with CaO, TCP with NaF and Ag$_2$O, and TCP with the quaternary composition. (hkl) values are labeled for the peaks that correspond with β-TCP (JCPDS file 00-032-0176). α-TCP (00-003-0348), and HAP (01-074-0566) peaks are also labeled. β-TCP peaks did not vary significantly from one composition to another, suggesting that the major phase of these ceramics was not altered significantly due to the addition of dopants. However, some α-TCP and HAP peaks are present even in pure TCP powder. Compositions containing NaF and CaO showed an increase in HAP phase. Both these dopant powders are hydroscopic and thus the presence of absorbed water may facilitate the phase transition from TCP to HAP. Also the addition of CaO increases the Ca to P ratio closer to the stoichiometry of HAP. Samples containing NaF showed significant reduction in α-TCP phase formation. This could be due to the fact that the cubic crystal structure of NaF is closer to the rhombohedral structure of β-TCP than of orthorhombic α-TCP (25), which helps stabilize the β-TCP phase.

In Vitro Cell-Materials Interaction.

Figure 4:
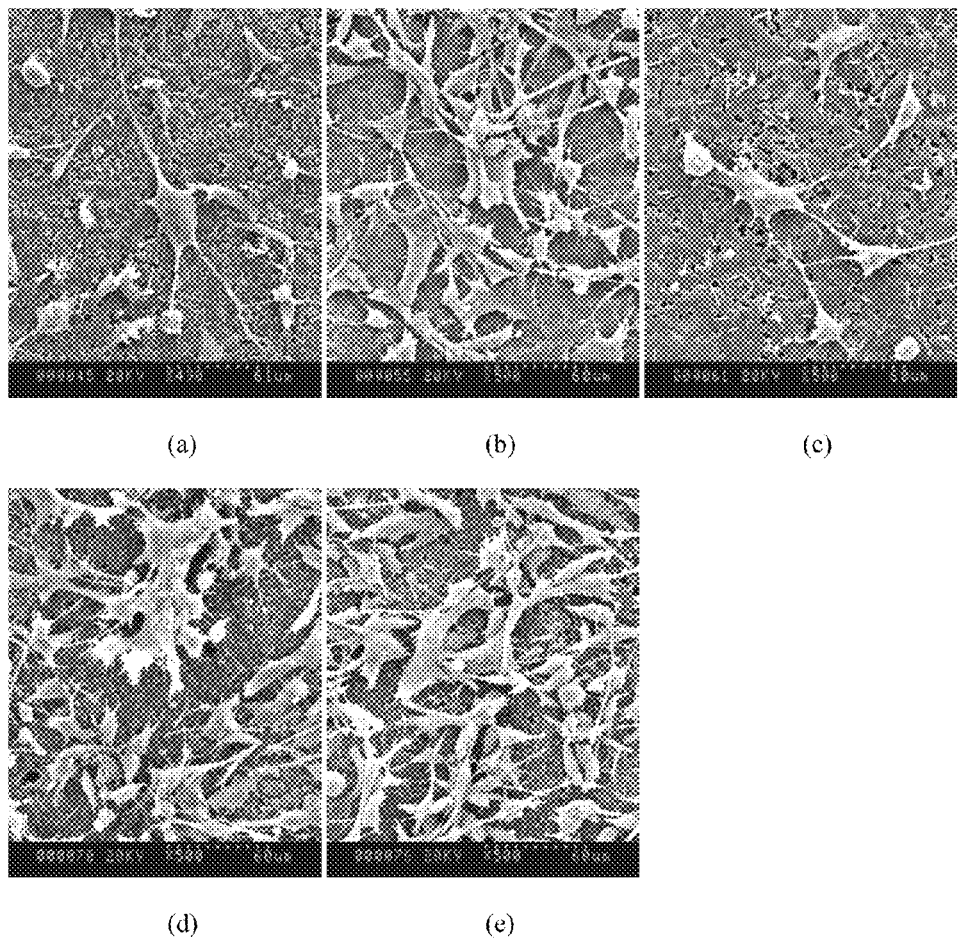
FIG. 4 shows, according to particular exemplary aspects of the present invention, SEM micrographs of cell cultures after 5 days on the disc samples of (a) pure TCP, (b) NaF doped, (c) CaO doped, (d) NaF—$Ag_2O$ doped, (e) quaternary.

FIG. 4 shows micrographs of cell cultures/attachment after 5 days on disc samples with different compositions. OPC-1 cells attached and proliferated on all the surfaces, maximizing surface area in contact with the ceramic. NaF-doped discs showed improved proliferation and cell spreading over that of pure TCP. This may be due to the decrease in porosity in the NaF doped samples which affects the surface roughness.

Figure 5:
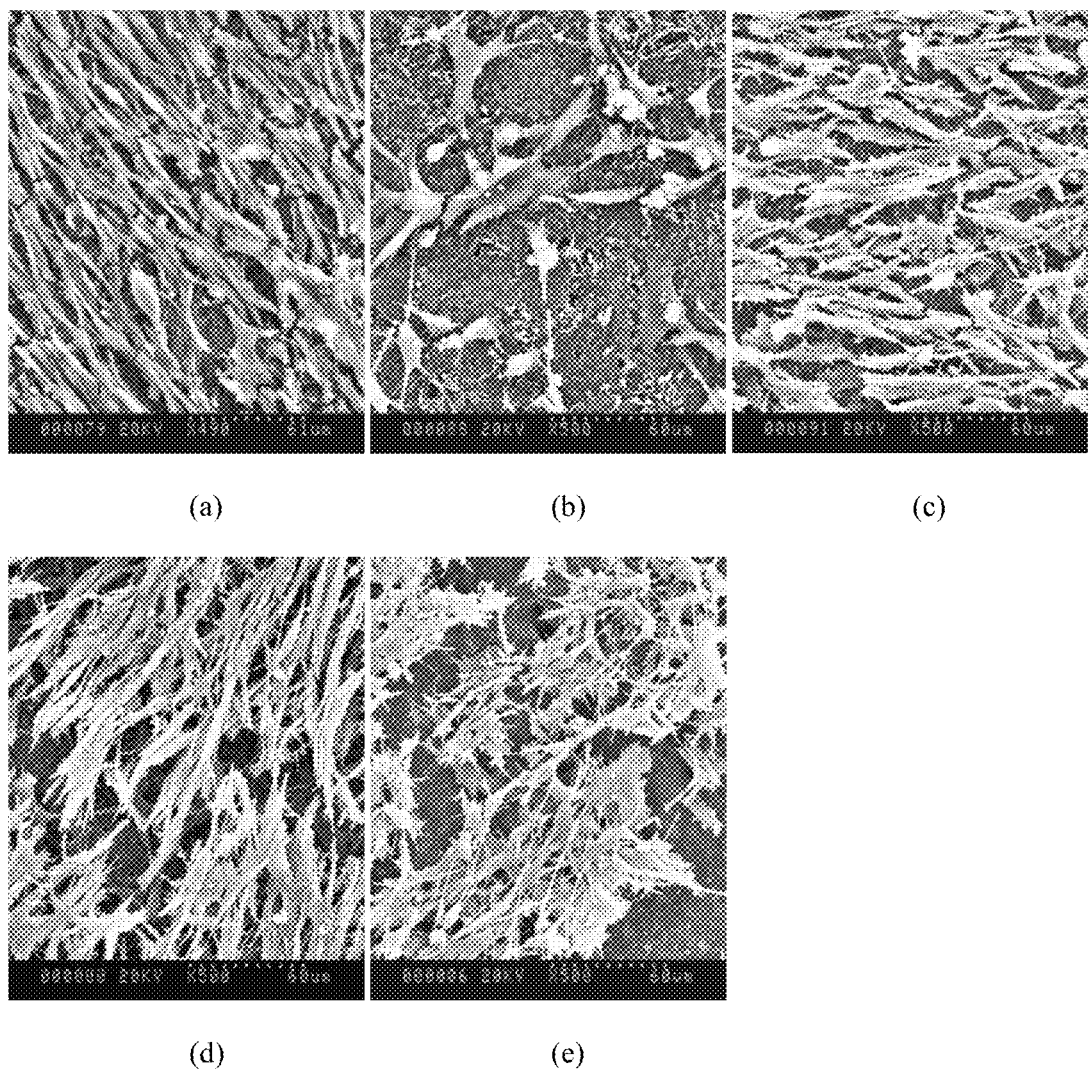
FIG. 5 shows, according to particular exemplary aspects of the present invention, SEM micrographs of cell cultures after 11 days on the disc samples of (a) pure TCP, (b) NaF doped, (c) CaO doped, (d) NaF—Ag$_2$O doped, (e) quaternary.

By day 11, shown in FIG. 5, the surface of all samples, except TCP with NaF, was covered with multiple layers of cells. A banding structure among the cells could also be seen, indicating that differentiation was beginning to occur (26). These results agree with similar research findings that trace elements are important to incorporate in TCP ceramics for applications such as tissue engineering (10).

Figure 6:
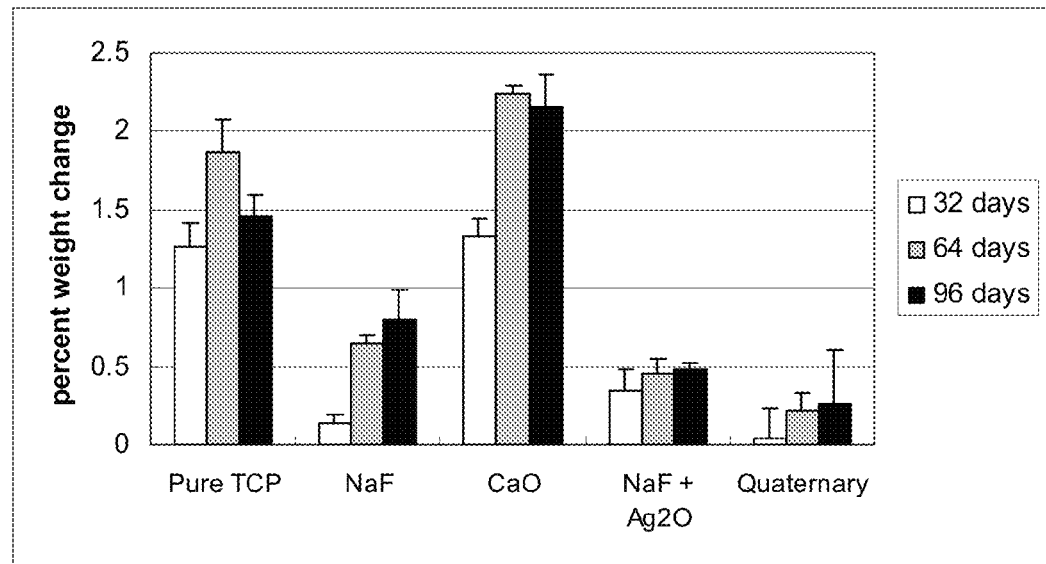
FIG. 6 shows, according to particular exemplary aspects of the present invention, weight increase of cylinder samples after 32, 64, and 96 days SBF treatment. (a) pure TCP, (b) NaF doped, (c) CaO doped, (d) NaF—Ag$_2$O doped, (e) quaternary.

Mineralization and strength degradation in SBF: FIG. 6 shows the percent weight change of the compression samples for 32, 64, and 96 days in SBF. All samples gained weight. This suggests that apatite formation was prevailing over resorption. Moreover, samples with higher porosity gained more weight due to apatite formation. Also, NaF containing samples continued to gain weight up to 96 days, while other compositions lost weight after 64 days.

Compression strength of each composition was measured for as processed samples and after 32, 64, and 96 days in SBF. Like weight change, compression strength can be affected by the two competing factors; dissolution and apatite formation. Dissolution, including formation of pores and grain boundary degradation, would be detrimental to compression strength, causing the cylinders to fracture at lower stresses. Precipitation, however, helps to fill pores and voids in the sample, which can then provide support for the structure and increase failure stresses.

Figure 7:
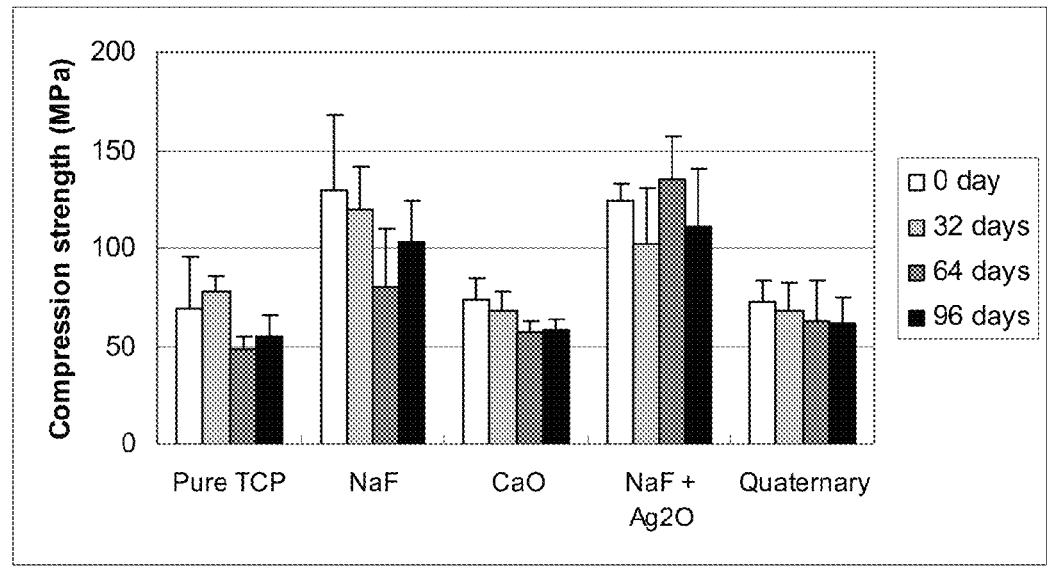
FIG. 7 shows, according to particular exemplary aspects of the present invention, compression strength of pure TCP and doped samples after 0, 32, 64, and 96 days SBF treatment.

FIG. 7 shows the compression strength for all compositions. No significant degradation was observed up to 96 days. TCP with NaF, TCP with CaO, and TCP with the quaternary composition showed a steady decrease in strength over time, while compression strength of pure TCP first increased and then decreased. A clear trend was observed between density and compression strength from FIG. 1 and FIG. 7. As sintered density increased due to dopants, as processed compression strength also increased.

Figure 8:
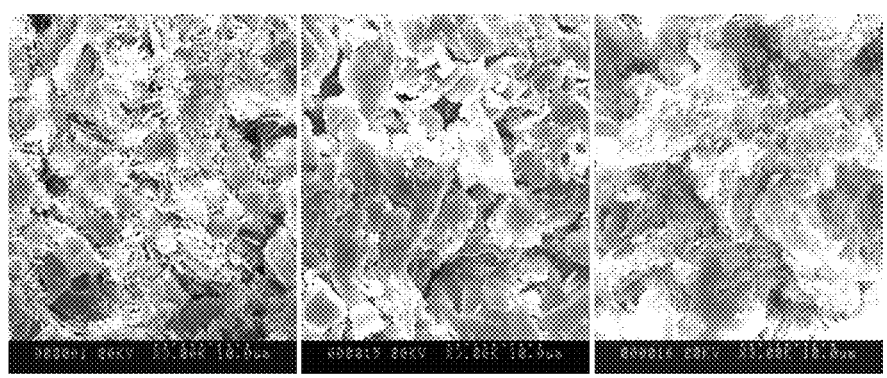
FIG. 8 shows, according to particular exemplary aspects of the present invention, SEM micrographs of fracture surface of compression cylinders after 96 days of SBF treatment. (a) pure TCP, (b) NaF doped, (c) CaO doped, (d) NaF—Ag$_2$O doped, (e) quaternary.
Figure 8:
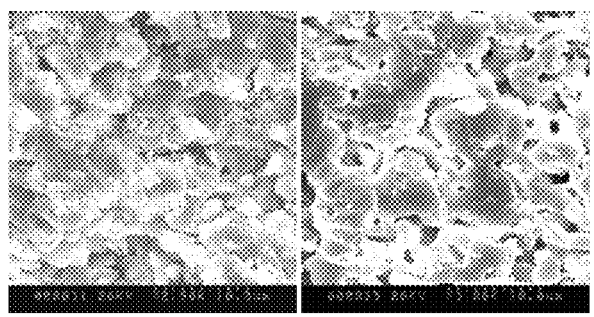
Figure 9:
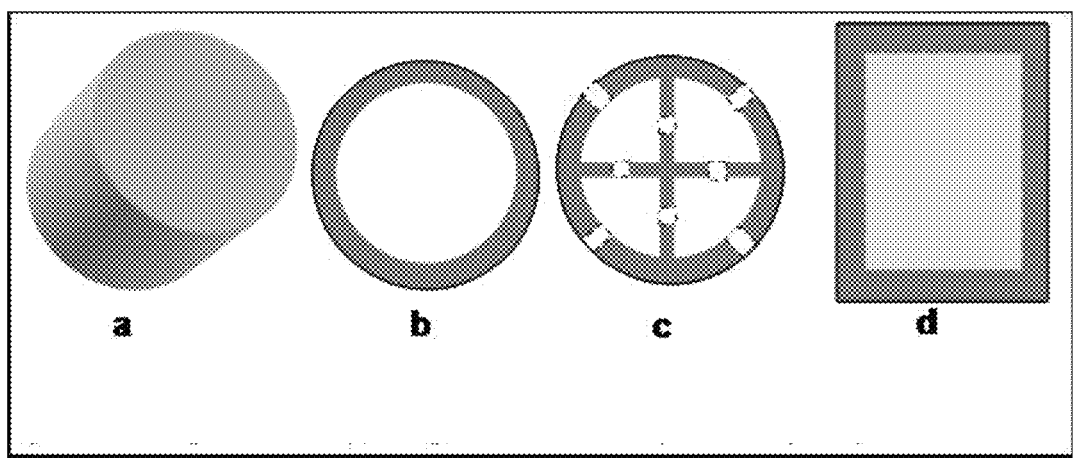
FIG. 9 shows, according to particular exemplary aspects of the present invention, a conceptual design of hollow implants: (a) hollow cylinder from outside; (b and c) possible cross-sectional views of internal porosity, closed hollow porosity or connected porosity for guided tissue regeneration; and (d) a longitudinal view of the cylinder with porosity (b).

FIG. 8 shows SEM micrographs of the fracture surface for each composition after 96 days in SBF. All samples showed varying amounts of apatite precipitation. This suggests that pores in the sample were inter-connected, thus SBF was able to penetrate into the sample, causing bone-like apatite mineralization. Among them, samples of TCP and TCP with CaO can be seen to have the most significant amounts of mineralization; these were samples that gained the most weight. All compositions with NaF showed very little mineralization, due to low porosity inhibiting the penetration of SBF into the sample. These micrographs confirm that weight increase in the samples was due to the formation of apatite.

References Relating to Example 1

1) K. Fujimura, K. Bessho, Y. Okubo, N. Segami, T. Iizuka, "A bioactive bone cement containing Bis-GMA resin and A-W glass-ceramic as an augmentation graft material on mandibular bone," Clin Oral Implants Res, 14 (2003) 659-67.
2) A. Moreira-Gonzalez, C. Lobocki, K. Brarakat, L. Andrus, M. Bradford, M. Gilsdorf, et al. "Evaluation of 45S5 bioactive glass combined as a bone substitute in the reconstruction of critical size calvarial defects in rabbits," J Craniofac Surg 16 (2005) 63-70.
3) M. Marcacci, E. Kon, S. Zaffagnini, R. Giardino, M Rocca, A. Corsi, et al. "Reconstruction of extensive long-bone defects in sheep using porous hydroxyapatite sponges," Calcif Tissue Int 64 (1999) 83-90.
4) H. Wang, "Ca/P ratio on the degradation of hydroxyapatite in vitro", J. of Biomedical Materials Research part A, 67A (2) 599-608.
5) A. Yasko, "Comparison of biological and synthetic carriers for recombinant human BMP induced bone formation," Trans. Orth. Res. Soc. 17(1992) 71.
6) B. Ratner, A. Hoffman, F. Schoen, J. Lemons, "Biomaterials Science—An Introduction to Materials in Medicine, second edition," 2004, Academic Press, San Diego, Calif. pp. 82-83.
7) X. Guo, K. Lee, L. Law, H. Chow, R. Rosier, C. Cheng, "Recombinant human bone morphogenetic protein-4 (rh-BMP-4) enhanced posterior spinal fusion without decortication," J. of Orthopedic research 20 (2002) 740-746.
8) I. Zerbo, S. Zijderveld, A. De Boer, A. Bronckers, G. De Lange, C. Bruggenkate, E. Burger, "Histomorphometry of human sinus floor augmentation using a porous (3-tricalcium phosphate: a prospective study," Clinical oral Implant Research 15 (2004).
9) Y. Zhang, J. Santos, "Crystallization and microstructure analysis of calcium phosphate-based glass ceramics for biomedical applications", J. of Non-Crystalline Solids, 272 (2000) 14-21.
10) S. Kalita, S. Bose, H. Hosick, A. Bandyopadhyay, "CaO-P2O5-Na2O-based sintering additives for hydroxyapatite (IIap) ceramics", Biomaterials, 25 (2004) 2331-2339.
11) K. de Groot, "Bioceramics of Calcium Phosphate", CRC Press, Boca Raton, Fla., 1983.
12) K. TenHuisen, P. Brown, "Hydrolysis of α-tricalcium phosphate in NaF solutions", Biomaterials 20 (1999) 427-434.
13) Y. Doi, Y. Shimizy, Y. Moriwaki, M. Aga, H. Iwanaga, T. Shibutani, k. Yamamoto, Y. Iwayama, "Development of a new calcium phosphate cement that contains sodium calcium phosphate", Biomaterials 22 (2001) 847-845.
14) J. Vogel, Bioceramics, 10 (1997) 57.
15) Knabe C, G. Berger, R. Gildenhaar, J. Meyer, C. Howlett, B. Markovic, H. Zreiqat, "Effect of rapidly resorbable calcium phosphates and a calcium phosphate bone cement on the expression of bone-related genes and proteins in vitro", J Biomed Mater Res. 69A:145-154 (2004).
16) R. LeGeros, "Calcium phosphates in oral biology and medicine", Monogr Oral Sci 15 (1991) 1-201.
17) L. Chow, "Tooth-bound fluoride and dental caries", J. of Dent Res 69 (1990) 595-600.
18) Kinnari A. Bhadang, K. Gross, "Influence of fluorapatite on the properties of thermally sprayed hydroxyapatite coatings", Biomaterials 25 (2004) 4935-4945.
19) R. Cass, J. Croft, P. Perkins, W. Nye, C. Waterhouse, R. Terry, "New bone formation in osteoporosis following treatment with sodium fluoride", Arch Intern Med 118 (1966) 111-116.
20) M. Inoue, H. Nagatsuka, H. Tsujigiwa, M. Inoue, R Z. LeGeros, T. Yamamoto, N. Nagai, "In vivo effect of fluoride-substituted apatite on rat bone," Dent Mater J." 2005 September; 24(3):398.
21) L. Gineste, M. Gineste, X. Ranz, A. Ellefterion, A. Guilhem, N. Rouguet, P. Farayssinet, "Degradation of hydroxyapatite, fluorapatite and fluorhydroxyapatite coatings of dental implants in dogs", J. of Biomed Mater Res 48 (1999) 224-34.
22) L. Rodriguez-Lorenzo, J. Hart, K. Gross, "Influence of fluorine in the synthesis of apatites, synthesis of solid solutions of hydroxyl-fluorapatite", Biomaterials 24 (2003) 3777-3785.
23) S. Winn, G. Randolph, H. Uludag, S. Wong, G. Hair, G. Hollinger, "Establishing an immortalized human osteoprecursor cell line: OPC1," J. Bone Miner Res. 14 (1999) 1-13.
24) Y. Estrin, G. Gottstein, and L. Shivindlerman, "Thermodynamic effect on the kinetics of vacancy-generating processes", Acta mater, 47 (1999) 3541-3549.
25) E. Eanes, "Thermochemical studies on amorphous calcium phosphate," Calcif Tissue Res. 5 (1970) 133-145.
26) N. Moritz, M. Jokinen, T. Peltola, S. Areva, A. Yli-Urpo, "Local induction of calcium phosphate formation on $TiO_2$ coatings on titanium via surface treatment with a $CO_2$ laser," J of biomed mater res A, 65 (2003) 9-16.

Example 2

Biodegradable CaPs with MgO, ZnO and $SiO_2$ Dopants

In this Example, commercial high purity beta-tricalcium phosphate ceramic compacts were made with the addition of MgO, ZnO and $SiO_2$ dopants in various combinations using ball milling with $ZrO_2$ milling media.

Methods.

Samples were pressed in a uniaxial press and then 'pressureless'-sintered in a muffle furnace in furnace air. These samples were then tested for physical, mechanical, and biological properties.

Results

Densification.

The compacts doped with MgO 1 wt %, 1 wt % $SiO_2$ and 5 wt % $SiO_2$ separately did not alter densification, however, 0.25 wt % ZnO decreased sintered density of TCP. By contrast, all binary and ternary dopant compositions showed an increase in densification compared to pure TCP.

Weight Change.

Weight change measurements after treatment in simulated body fluid (SBF) indicated that all single component systems and TCP-$SiO_2$—ZnO produced an increase in weight which was an indication of Ca-apatite growth. This data was also supported by microstructural analysis. However, for all binary and ternary compositions, weight change was negligible and sometimes negative, an indication that there was little or no apatite formation.

Degradation and Compressive Strength.

Microstructural analysis revealed signs of surface dissolution after 12 weeks in SBF for all samples. TCP was found to degrade after 8 weeks in SBF solution.

TCP-1 wt % $SiO_2$ compacts showed a continuous increase in compressive strength for 12 weeks in SBF, while TCP-5 wt % $SiO_2$ and TCP-MgO—ZnO compositions both illustrated a continuous decrease in compressive strengths over 12 weeks in SBF. It was also found that degradation began after 2 weeks for these compositions. For all other compositions, compressive strengths after 12 weeks remained similar or unchanged relative to their respective 'as-sintered' values.

Fractographic analysis revealed Ca-apatite formation inside the sample for pure TCP and single dopant compositions suggesting an interconnected open porosity throughout the sample. However, for binary and ternary dopants, higher densification reduced the open pore network.

In vitro cell materials interactions studies with OPC1 cells confirmed that that all compositions were biocompatible and non-toxic. Specific experiments on adhesion, proliferation and differentiation showed that the dopants play a significant role towards improving bone cell-materials interactions.

Example 3

In Vitro Cell-Materials Characterization

This Example shows the ability of the inventive materials to support OPC-1 cell growth and maturation.

Methods.

The ability of the inventive materials to support OPC-1 cell growth and maturation is tested by culturing primary cells directly on test samples and counting the number of viable cells existent at hallmark times for cell attachment, proliferation, and maturation. In addition to the CaP materials, a like number of commercially pure titanium (CP-Ti) and polymethyl methacrylate (PMMA) disks could be used. Both of these materials have historical use in orthopedics and dentistry, and are routinely used as implant biomaterials, can serve as internal controls.

Results.

Figure 10:
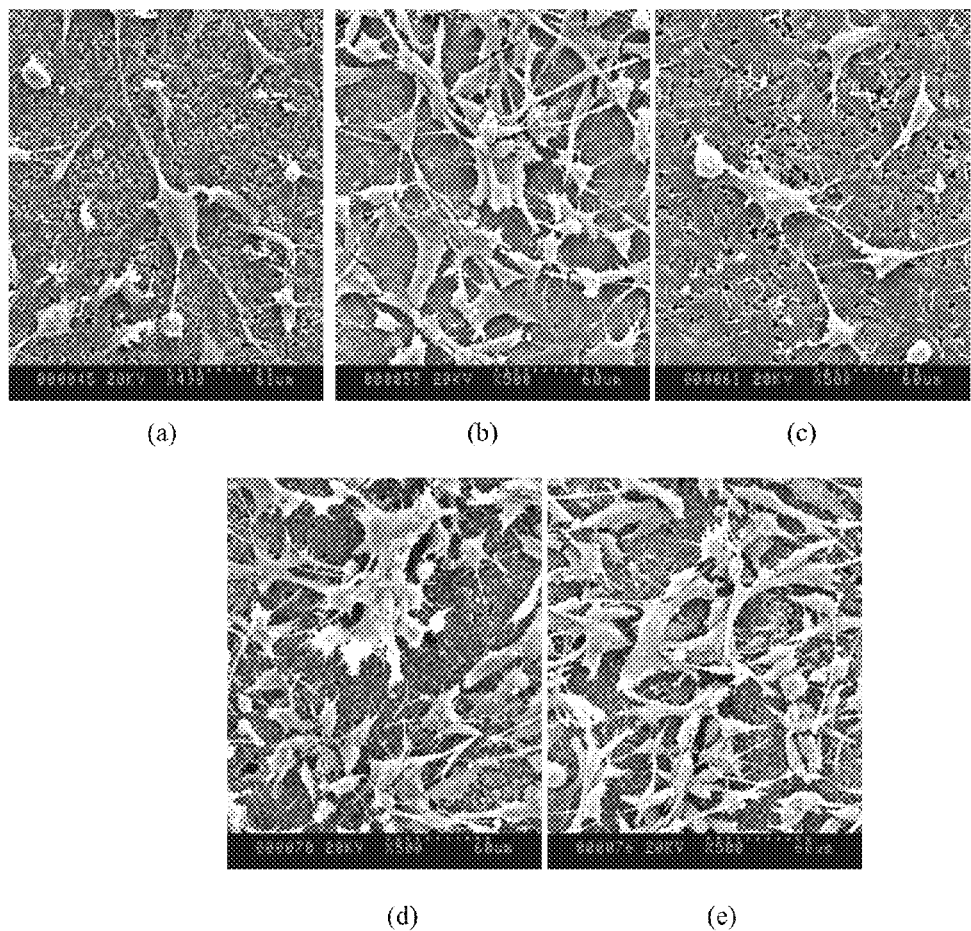
FIG. 10 shows, according to particular exemplary aspects of the present invention, SEM micrographs of cell cultures after 5 days on the disc samples of (a) pure TCP, (b) NaF doped, (c) CaO doped, (d) NaF—Ag$_2$O doped, (e) quaternary.
Figure 11:
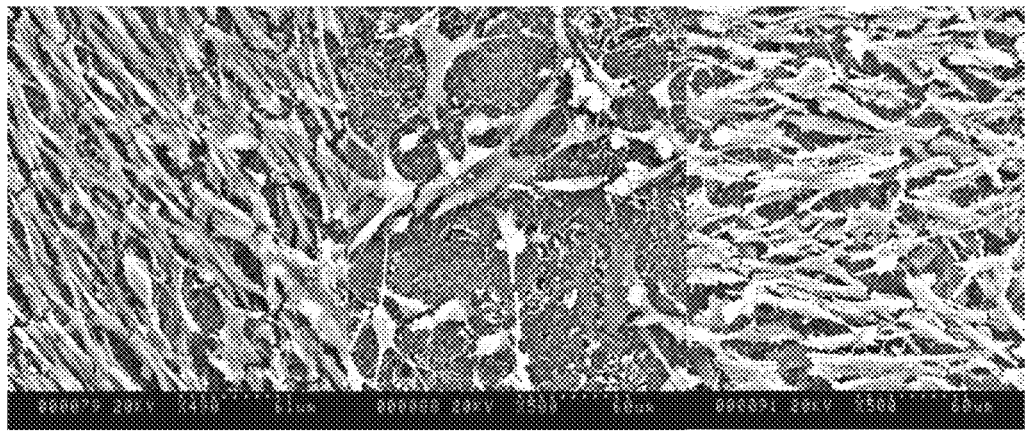
FIG. 11 shows, according to particular exemplary aspects of the present invention, SEM micrographs of cell cultures after 11 days on the disc samples of (a) pure TCP, (b) NaF doped, (c) CaO doped, (d) NaF—Ag$_2$O doped, (e) quaternary.
Figure 11:
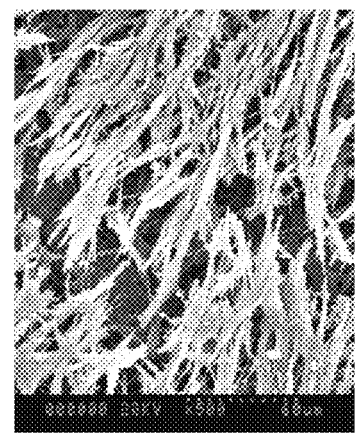
Figure 11:
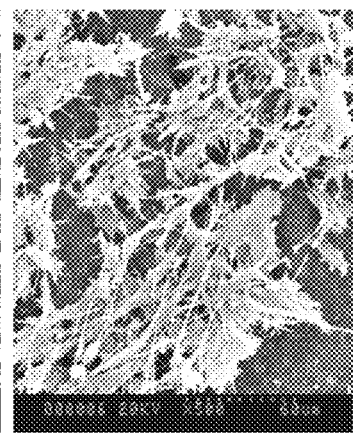

FIG. 10 shows micrographs of cell cultures/attachment after 5 days on disc samples having different compositions. OPC-1 cells attached and proliferated on all the surfaces, maximizing surface area in contact with the ceramic. NaF-doped discs (FIG. 10b) showed improved proliferation and cell spreading over that of pure TCP. This may be due to the decrease in porosity in the NaF doped samples which affects the surface roughness. By day 11, as shown in FIG. 11, the surface of all samples, except TCP with NaF (FIG. 11b), was covered with multiple layers of cells.

An alignment or 'banding structure' among the cells could also be seen, indicating that differentiation was beginning to occur (Moritz, 2003). These results are consistent with other findings that trace elements are important for applications such as tissue engineering (Kalita, 2004 (2)).

Example 4

Influence of Porosity on Porous CaPs

In this Example, the optimal pore size for bone regeneration was determined.

Methods.

Processing of controlled porosity ceramic structures was performed using the indirect fused deposition process, as previously described (Bose, 200303 (3)). Processing of controlled porosity ceramic preforms consists of three different types of development and optimization work, including: i (a) mold design; (b) development of ceramic slurry composition; and (c) binder burn out and sintering cycle development for green ceramic structures.

Molds are designed and fabricated by FDM 1650 using ICW-06 filament material. Molds are then infiltrated with CaP based ceramic slurry. Structures are subjected to a binder removal and sintering cycle to form the final porous ceramics.

Results.

Porous structures with pore size of 300 microns with 30 and 40 volume % has been shown optimal in previous work, and the optimal pore size for bone regeneration was in the range from 100 to 300 microns (Hulbert, 1970). Moreover, this pore size and volume porosity matches quite well with natural bone (Joschek, 2000).

Example 5

(Hydroxyapatite (HAP) with Metal Dopants as Sintering Additives

In this Example, yydroxyapatite (HAp) with metal ion dopants as sintering additives were studied.

Methods.

Preliminary studies started with selection of a few oxide-based sintering additives, selected on the basis of already reported results, including: C117-500 calcium oxide UN 1910 from Fisher Scientific; titanium dioxide from Bios Laboratory Inc.; sodium carbonate (S263-500) from Fisher Scientific; phosphorous pentoxide powder from J.T. Baker Inc; silica, aluminum oxide (CR 6D) and magnesium Oxide (ADM 98 H) from AluChem Inc. These oxides were added either individually or as a part of multi-components sintering aids, to synthetic hydroxyapatite powder (BABI-HAP-SP) obtained from Berkeley Advanced Biomaterials, Inc., followed by ball milling for homogeneous mixing.

Three-component sintering additives were prepared and used to achieve liquid phase sintering for better densification. Compositions for these additives were selected based on their respective ternary oxide phase diagrams and their melting temperatures. Exemplary compositions of sintering additives selected and tested are shown in TABLE 2 Sintering was done at 1250° C., and 1300° C. in a muffle furnace for 3 hours.

TABLE 2

Compositions of selected sintering additives

| Name | Composition |
| --- | --- |
| MgO | 100% MgO |
| CaO | 100% CaO |
| $TiO_2$ | 100% $TiO_2$ |
| X | 30% CaO, 30% $P_2O_5$ and 40% $Na_2O$ ($Na_2CO_3$) |
| XI | 36% $Na_2O$ ($Na_2CO_3$), 40.7% $P_2O_5$ and 23.3% MgO |
| XIX | 55% CaO, 30% $P_2O_5$ and 15% $Na_2O$ ($Na_2CO_3$) |

Results.

The results showed that there is substantil potential for improving densification and hardness of sintered hydroxy-apatite with addition of small amount of sintering additives (typically 2.5 wt %). Sintered densities of some of the HAp-2.5% dopants sintered at 1300° C. for 3 hrs were as high as 93% theoretical density via pressureless sintering.

An increase in the amount of dopants from 2.5% to 10 wt % did not show any improvement on densification with exception for pure $TiO_2$. Microhardness measurements on dense sintered discs show an increase in hardness as high as 200% by some of the sintering additives.

Example 6

Metal Ions as Dopants Using β-Tricalcium Phosphate (TCP)

This Example shows studies conducted with metal ions as dopants using β-tricalcium phosphate (TCP). MgO and ZnO were used as dopants with TCP.

Methods.

See Examples 1 and 2, herein above.

Results.

The results show that levels as high as 96% densification could be reached with MgO additives via pressure-less sintering. Additionally, ZnO as a dopant was used with both HAp and TCP ceramics.

Figure 12:
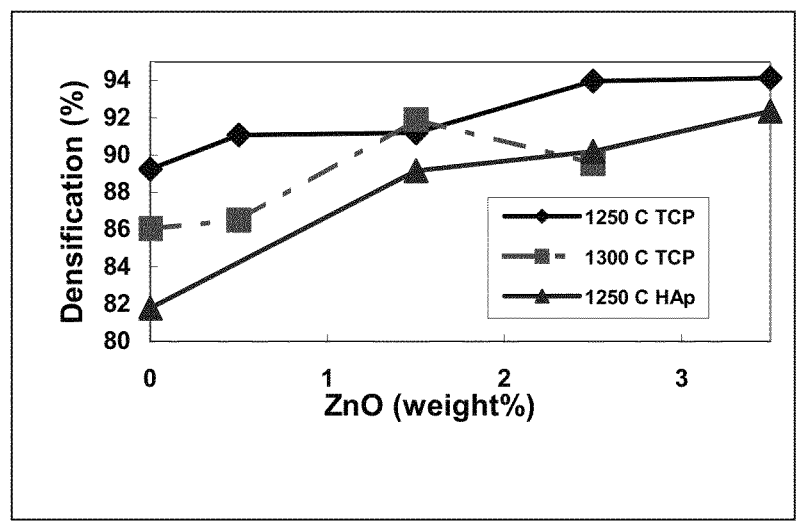
FIG. 12 shows, according to particular exemplary aspects of the present invention, densification behavior as a function of ZnO content in doped HAp and TCP powders.

FIG. 12 shows densification behavior as a function of ZnO content in doped HAp and TCP powders.

Figure 13:
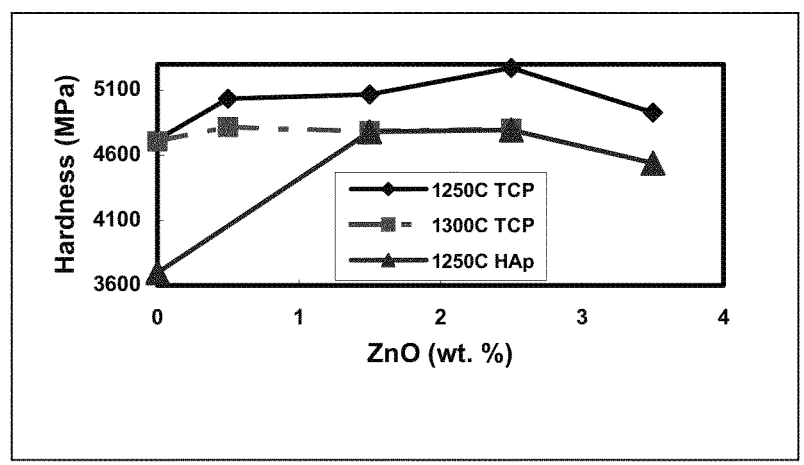
FIG. 13 shows, according to particular exemplary aspects of the present invention, the microhardness measurement data for HAp and TCP ceramics doped with ZnO.

FIG. 13 shows the microhardness measurement data for HAp and TCP ceramics doped with ZnO. It can be seen that addition of ZnO increases the densification of both HAp and TCP ceramics when sintered at 1250° C.

At 1300° C., there is no common trend in densification, which is believed to be due to degradation of calcium phosphates in to other phases. Significant increase in densification of HAp from 82% to 92% theoretical density is a remarkable achievement, considering this is pressureless sintering of uniaxially dry-pressed samples. For the case of TCP, the bulk density reached >94% theoretical.

Microhardness data for both TCP and HAp shows an increase with increasing amount of ZnO up to 2.5 weight %. The increase in HAp is more significant (>33% from original value) than in TCP, which is similar to the densification data.

Grain size measurement showed larger grain size for compositions >2.5 weight % ZnO, which is believed to be the reason for lower hardness though the density numbers are high.

Example 7

Synthesis of Calcium Phosphate Nano-Powders

This Example shows the synthesis of calcium phosphate nano-powders using different template materials including dendrimer, sucrose and various surfactants. We focused our synthesis effort primarily on hydroxiapatite i.e., ($Ca_{10}(PO_4)_6(OH)_2$ (HAp, Ca:P is 1.67:1), and tricalcium phosphate i.e., $Ca_3(PO_4)_2$ (TCP, Ca:P is 1.5:1) compositions. We have synthesized nanopowders of pure hydroxyapatite (HAp) and β-tri-calcium phosphate (β-TCP) compositions and phases. These powders were made using surfactant and sucrose as template materials [Bose '03 (1), Bose '03 (2)]. We have also synthesized alumina doped calcium phosphate nanopowders with 2.5% and 5.0 wt. % alumina [Bose '03 (1)]. Sucrose was used as a template material that introduced porosity and high surface area in the final nanopowders. Using this method we were able to produce powders with surface areas between 50 to 60 $m^2/gm$ and average particle size between 30 to 50 nm.

Example 8

Porous TCP Scaffolds

The Example shows studies on porous scaffolds with tri-calcium phosphate (TCP) powders.

Methods.

Commercially available TCP powder was purchased from Monsanto, Calif. Processing of controlled porosity ceramic preforms consisted of three different types of development and optimization work, including: (a) mold design; (b) development of ceramic slurry composition; and (c) binder burn out and sintering cycle development for green ceramic structures. Molds were designed and fabricated by FDM 1650 using ICW-06 filament material. Initially, 1" tall and 1" diameter cylindrical molds were designed and fabricated with a (45/−45) raster filling and varying the raster gap from 0.010 to 0.050". The top 0.3" of the mold had only a perimeter but no raster filling, called lip, to hold excess ceramic slurry during infiltration. The bottom four layers of the mold had no raster gap to avoid leaking of slurry during infiltration. The road width was varied from 0.015 to 0.025". The combination of raster gaps and road width control the volume fraction of ceramics and corresponding pore sizes (see, e.g., Hattiangadi, 2000).

Once molds were made, they were infiltrated with solids-loaded ceramic slurry. Development of highly loaded slurry is very important to reduce cracking related problems during the post processing. 1-Butanol was used as an antifoaming agent for both powders. D-3021 (Rohm and Haas, Pa.) was used as dispersant. Binder B-1001 (Rohm and Haas, Pa.) was used as binder. Ceramic powder, antifoaming agent and dispersant were added to water and then ball milled for 16 hours in a polyethylene bottle. The required amount of binder was added to the mixture just before the infiltration. 3.5 wt % of D-3021 was found optimum for TCP powders. Slurry compositions were optimized using a Brookfield viscometer. The slurry was infiltrated into the porous polymeric molds and the green structures were dried for two days. The structures were then subjected to a binder burn out and sintering cycle. During the binder burn out heating cycle the mold polymer leaves the part, creating the pores. A final sintering temperature of 1250° C. and a hold time of 3 hours were used for all the samples. Shrinkage was measured to understand the sintering behavior of these ceramics. For the porous TCP samples, shrinkage varied between 17 and 19%. For TCP, the density varied between 2.90-2.95 $gms/cm^3$ (~90% theoretical density) [Bose '03 (3)].

Results.

Figure 14:
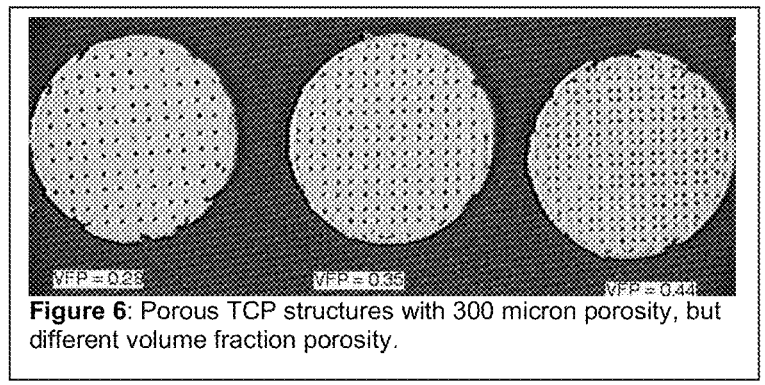
FIG. 14 shows, according to particular exemplary aspects of the present invention, shows porous TCP samples with the pore size kept constant at 300 micron, but with the pore-pore spacing varied to change the volume fraction porosity from 29% to 44%

FIG. 14 shows porous TCP samples with the pore size kept constant at 300 micron, but with the pore-pore spacing varied to change the volume fraction porosity from 29% to 44% (see, e.g., Bose 2003 (3)). Strength degradation is a serious concern in porous ceramics. As the total volume fraction porosity increases, the failure strength decreases. Cylindrical porous samples of 12 mm diameter and 20 mm long (L/D=1.6) were used to collect preliminary data on compression strengths of porous TCP structures. Uniaxial compression tests were performed using an Instron 1331 servo hydraulic machine under stroke control mode at a stroke rate 0.5 mm/minute. At least 20 samples of each porosity level were tested.

Figure 15:
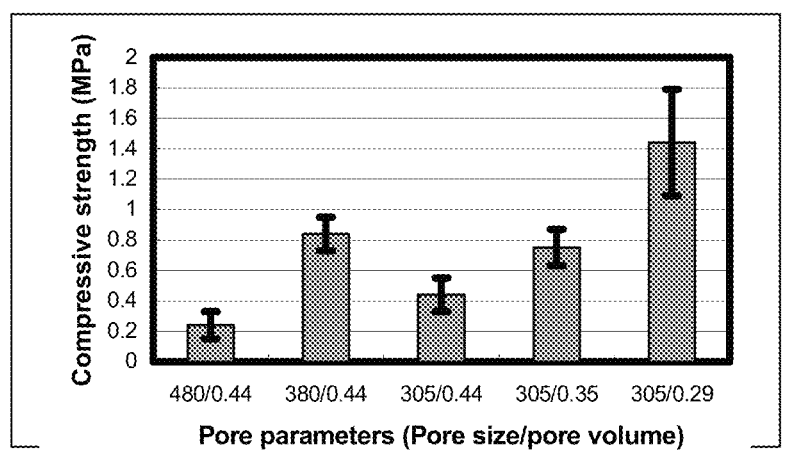
FIG. 15 shows, according to particular exemplary aspects of the present invention, variation of compression strength as a function of pore size/pore volume effects on TCP samples.

FIG. 15 shows variation of compression strength as a function of pore size/pore volume effects on TCP samples. Pore size has almost no effect on compression strength; however, increasing pore volume significantly lowers the strength. Highest compression strength was observed at 1.4

MPa for 29 volume % porosity samples with 305 microns pores (see, e.g., Bose, 2003 (3)). It is clear that for any real applications, there is a strong need for strength improvements in these ceramics, which is one of the main advantages provided by the presently disclosed subject matter.

Example 9

(In Vitro Studies of CaPs with Human Osteoblast (HOB) Cells

This Example shows results of in vitro tests using the OPC 1 cell line.

Methods.

In vitro tests were carried out in petri dishes using a selected cell line under controlled laboratory conditions. The cell line used in this study is OPC 1, a modified human osteoblast (HOB) cell-line. OPC1 is a conditionally immortalized osteoprecursor cell line (OPC 1) derived from human fetal bone tissue (Winn, 1999). In vitro analyses using OPC 1 cell line on ceramic scaffolds involve culturing, splitting and seeding of cells in an aseptic environment. OPC 1 cells were cultured in a standard medium made of Mccoy's 5A (with 1-Glutamine, without Phenol Red and Sodium Bicarbonate) (Sigma Chemical Co, Saint Louis, Mo.), supplemented with 10% fetal bovine serum, 2.2 gram/liter sodium bicarbonate, 0.1 gram/liter penicillin and 0.1 gram/liter streptomycin. OPC1 cells were seeded on top of ceramic matrices placed on a petri dish and are cultured in an incubator at 37° C. in a humidified 5% $CO_2$ atmosphere.

Results.

Figure 16:
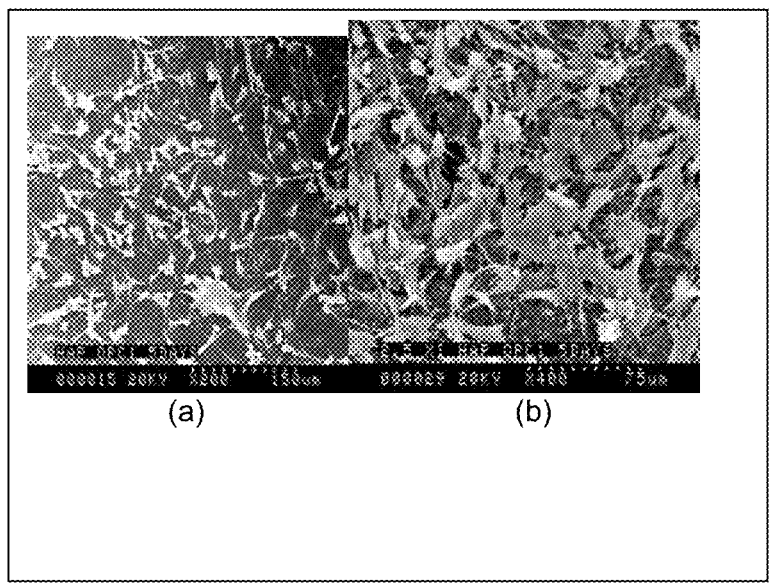
FIG. 16 shows, according to particular exemplary aspects of the present invention, OPC1 cells on Hap ceramics: (a) pure Hap and (b) Hap with dopants. It is clear that both cell adhesion and cell spreading were significantly modulated by the use of small quantities of dopants.

Microscopic observations were done on various time points to assess cell attachment, anchoring and differentiation on a particular ceramic composition. The results cofirmed that the matrices were non-toxic, and in particular instances enhanced cell spreading was observed due to the presence of metal-ions as shown in FIG. 16.

FIG. 8 shows OPC1 cells on Hap ceramics: (a) pure Hap and (b) Hap with dopants. It is clear that both cell adhesion and cell spreading were significantly modulated by the use of small quantities of dopants.

Cited References for Example 1-9

Anstis, G. R., Chantikul, P., Lawn, B. R. and Marshall, D. B., *J. Am. Ceram. Soc.,* 1981, 64, 533.
Bandyopadhyay, A., Liz O, Peterson C, and J. Moore, Influence of Zn and Fe on densification and in vitro cell growth behavior on HAp and TCP ceramics, unpublished work, 2004.
Bellows C G, Aubin J E, Heersche J N, Antosz M E. Mineralized bone nodules formed in vitro from enzymatically released rat calvaria cell populations. Calcif Tissue Int. 38(3):143-54, 1986.
Bellows, C. G., Aubin, J. E., and Heersche J. N. M. Physiological concentrations of glucocorticoids stimulate formation of bone nodules from isolated rat calvaria cells in vitro. Endocrinology 121:1985-1992; 1987.
Berger G, Gildenhaar R and Ploska U. Rapid resorbable, glassy crystalline materials on the basis of calcium alkali orthophosphates. *Biomaterials.* 16:1241-8 (1995).
Bertoni E, Bigi A, Cojazzi G, Gandolfi M, Panzavolta S and Rover N. Nanocrystals of Magnesium and fluoride substituted hydroxyapatite. *J Inorg Biochem.* 72:29 (1998).
(1) S. Bose and S. K. Saha, "Synthesis of hydroxyapatite nanopowder using sucrose templated sol-gel method" *Journal of the American Ceramic Society,* 86 [6], pp. 1055-57 (2003).
(2) S. Bose and S. K. Saha, "Synthesis and characterization of hydroxyapatite nanopowders by emulsion technique", *Chem. Mater.,* 15 (23), 4464-4469 (2003).
(3) Bose S., Darsell J., Kintner M., Hosick, H. and Bandyopadhyay A., "Pore Size and Pore Volume Effects on Calcium Phosphate Based Ceramics," *Materials Science and Engineering C,* 23, pp. 479-86 (2003).
Burg K J L, Porter S, Kellam J F. Biomaterial developments for bone engineering. Biomaterials 2000; 21:2347-59.
Buser D, Dula K, Hirt H P and Berthold H. Localized ridge augmentation using guided bone regeneration. *Guided bone regeneration in implant dentistry.* Edited by Buser D, Dahlin C and Schenk R K. Chicago: Quintessenz; 189-233 (1994).
Carlisle E M. Silicon: a possible factor in bone calcification. *Science.* 167:279 (1970).
Caverzasio J., G. Palmer and J. P. Bonjour, Fluoride: mode of action. *Bone* 22, pp. 585-589 (1998).
Christoffersen M R, Thyregod H C and Christoffersen J. Effects of aluminum(III), chromium(III) and iron(III) on the rate of dissolution of calcium hydroxyapatite crystals in the absence and presence of the chelating agent desferrioxamine. *Calcif Tissue Int.* 41:27-30 (1987).
Deal C L. Osteoporosis: prevention, diagnosis, and management. [Review] Am J Med; 102(1A) (Suppl):35S-9S (1997).
Demos L. L., H. Kazda, F. M. Cicuttini, M. I. Sinclair and C. K. Fairley, Water fluoridation, osteoporosis, fractures—recent developments. *Aust Dental J* 46 2, pp. 80-87 (2001).
Ducheyne P., Q. Qiu, "Bioactive ceramics: the elect of surface reactivity on bone formation and bone cell function," Biomaterials 20 (1999) 2287-2303.
Hamilton E I, Minski M J and Cleary J J. The concentration and distribution of some stable elements in healthy human tissues from the United Kingdom: An environmental study. *Sci Total Environ.* 1:341-374 (1972/73).
Hashizume M and Yamaguchi M. Stimulatory effect of β-alanyl-1-histidinato zinc on cell proliferation is dependent on protein synthesis in osteoblastic MC3T3-E1 cells. *Mol Cell Biochem.* 122:59-64 (1993).
Hattiangadi A. and Bandyopadhyay A., "Strength Degradation of Porous Ceramics Under Uniaxial Compressive Loading," *Journal of the American Ceramic Society,* 83 [11], pp. 2730-36 (2000).
Hayakawa S, Tsuru K, Ohtsuki C and Osaka A. Mechanism of apatite formation on a sodium glass in a simulated body fluid. *J Am Ceram Soc.* 8:2155 (1999).
Ilench L and Wilson J., "An Introduction to Bioceramics," World Scientific, London, U.K. (1993).
Heughebaert M, LeGeros R Z, Gineste M, Guillielm A and Bonel G, "Physicao cahmical hearacterization of deposits associated with hydroxyapatite ceramics implaned in non-osseous sites" J. Biomed Mater. Res. Appl. Biomat. 1988, 22, A23, 257-268.
Hulbert S F, Young F A, Matthews R S, et al. Potential ceramic materials as permanently implantable skeletal prosthesis. J Biomed Mater Res 1970; 4: 443.
Ito A, Ojima K, Naito H, Ichinose N and Tateishi T. Preparation, solubility, and cytocompatibility of zinc-releasing calcium phosphate ceramics. *J Biomed Mater Res.* 50:178-183 (2000).
Joschek S, Nies B, Krotz R and Göpferich A. Chemical and physicochemical characterization of porous hydroxyapatite ceramics made of natural bone. *Biomatrials.* 21:1645-1658 (2000).

(1) Kalita S. J., S. Bose, D. Rokusek, H. L. Hosick and A. Bandyopadhyay, "Effects of MgO—CaO—$P_2O_5$—$Na_2O$ based additives on mechanical and biological properties of hydroxyapatite," in press, *Journal of Biomedical Materials Research*, June 2004.

(2) Kalita S. J., S. Bose, H. L. Hosick and A. Bandyopadhyay, "CaO—$P_2O_5$—$Na_2O$ based sintering additives for hydroxyapatite (HAp) ceramics," *Biomaterials*, 25, pp. 2331-2339 (2004).

Kawamura H, Ito A, Miyakawa S, Layrolle P, Ojima K, Ichinose N and Tateishi T. Stimulatory effect of zinc-releasing calcium phosphate implant on bone formation in rabbit femora. *J Biomed Mater Res.* 50:184-190 (2000).

Kamakura S, Sasano Y, Shimizu T, Hatori K, Suzuki O, Kagayama M and Motegi K. Implanted octacalcium phosphate is more resorbable than β-tricalcium phosphate and hydroxyapatite. *J Biomed Mater Res.* 59:29-34 (2002).

Kim S R, Lee J H, Kim Y T, Riu D H, Jung S J, Lee Y J, Chung S C and Kim Y H. Synthesis of Si, Mg substituted hydroxyapatites and their sintering behaviors. *Biomaterials.* 24:1389-1398 (2003).

Kishi S and Yamaguchi M. Inhibitory effect of zinc compounds on osteoclast-like cell formation in mouse marrow culture. *Biochem Pharmacol.* 48:1225-1230 (1994).

Knabe C, Gildenhaar R, Berger G, Ostapowicz W, Fitzner R, Radlanski R J and Gross U. Morphological evaluation of osteoblasts cultured on different calcium phosphate ceramics. *Biomaterials.* 18:1339-47 (1997).

Knabe C, Berger G, Gildenhaar R, Howlett C R, Markovic B and Zreiqat H. The functional expression of human bone-derived cells grown on rapidly resorbable calcium phosphate ceramics. *Biomaterials.* 25:335-344 (2004).

Knabc C, Berger G, Gildenhaar R, Meyer J, Howlett C R, Markovic B and Zreiqat H. Effect of rapidly resorbable calcium phosphates and a calcium phosphate bone cement on the expression of bone-related genes and proteins in vitro. *J Biomed Mater Res.* 69A:145-154 (2004).

Knowles J C, Talal S, Santos J D., Sintering effects in a glass reinforced hydroxyapatite. Biomaterials 1996; 17(14): 1437.

Kokubo T, Cho S B, Nakanishi K, Ohtsuki C, Kitsugi T, Yamamuro T and Nakamura. Dependence of bone like hydroxyapatite formation on structure of silica gel. *Bioceramics.* 7:49 (1994).

Lansdown, A. B. G., Silver 2: toxicity in mammals and how its products aid wound repair 11, 173 (2002).

LeGeros R Z, Daculsi G, Kijkowska R and Kerebel B. *The effect of magnesium on the formation of apatites and whitlockites. Edited by Itokawa Y and Durlach J. London: John Libbey;* 11 (1989).

LeGeros R, Daculsi G. CRC Oreess handbook of bioactive ceramics. In: Yamanuro T, Hench L, Wilson J, editors. Boca raton: CRC Press, 1990.

Lanza R, Langer R, Chick, W. Principles of Tissue Engineering, Academic Press, Inc, 1997.

Larrabee R A 3rd, Fuski M P and Bajpai P K. A ferric calcium phosphorous oxide (FECAP) ceramic for rebuilding bone. *Biomed Sci Instrum.* 29:59-64 (1993).

Lucas J., Fluorine in the natural environment. *J Fluor Chem* 41, pp. 1-8 (1988).

Manjubala I and Sampath Kumar T S. Effect of $TiO_2$—$Ag_2O$ additives on the formation of calcium phosphate based functionally graded bioceramics. *Biomaterials.* 21:1995-2002 (2000).

Mayer I, Schlam R and Featherstone F D B. Magnesium-containing carbonate apatites. *J Inorg Biochem.* 66:1 (1997).

Moonga B S and Dempster D W. Zinc is a potent inhibitor of osteoclastic bone resorption in vitro. *J Bone Miner Res.* 10:453-457 (1995).

N. Moritz, M. Jokinen, T. Peltola, S. Areva, A. Yli-Urpo, "Local induction of calcium phosphate formation on $TiO_2$ coatings on titanium via surface treatment with a $CO_2$ laser," J of biomed mater res A, 65 (2003) 9-16.

Nancollas G H, Tomazic B and Tomson M. The precipitation of calcium phosphates in the presence of magnesium. *Croat Chem Acta.* 48: 431 (1976).

Narasaraju T. S. B. and D. E. Phebe, Some physico-chemical aspects of hydroxylapatite. *J Mater Sci* 31, pp. 1-21 (1996).

Okazaki M., H. Tohda, T. Yanagisawa, M. Taira and J. Takahashi, Differences in solubility of two types of heterogeneous fluoridated hydroxyapatites. *Biomaterials* 19, pp. 611-616 (1998).

Oki A, Parveen B, Hossain S, Adeniji S and Donahue H. Preparation and in vitro bioactivity of zinc containing sol-gel-derived bioglass materials. *J Biomed Mater Res.* 69A:216-221 (2004).

Otsuka M, Ohshita Y, Marunaka S, Matsuda Y, Ito A, Ichinose N, Otsuka K and Iliguchi W. Effect of controlled zinc release on bone mineral density from injectable Zn-containing β-tricalcium phosphate suspension in zinc-deficient diseased rats. *J Biomed Mater Res.* 69A:552-560 (2004).

Page B., Page M, and Noel C. 1993, A new fluorometric assay for cytotoxicity measurements in vitro. Int. J Oncology 3:473-476.

Park, Joon Bu. *Biomaterials Science and Engineering*, New York, N.Y., Plenum Press, 1984.

Percival M. Bone health & Osteoporosis. *Appl Nutr Sci Rep.* 5:1 (1999).

Ramires P. A., Romito A, Cosentino F, Milella E., "The influence of titania/hydroxyapatite composite coatings on in vitro osteoblasts behaviour," Biomaterials, 22(12): 1467-74 (2001).

Ravaglioli A. and Krajewski A., "Bioceramics", Chapman and Hall, p 174 (1992).

Stricker N J, Larrabee R A 3rd and Bajpai P K. Biocompatibility of ferric calcium phosphorous oxide ceramics. *Biomed Sci Instrum.* 28:123-8 (1992)

Stickler, D. J., Biomaterials to prevent nosocomial infections: is silver the gold standard? Current Opinion in Infectious Diseases, 13 (4): 389-393 (2000).

Suchanek W. and Yoshimura M., Processing and properties of HAp based biomaterials for use as hard tissue replacement implants, *J. Mater. Res.,* 13, pp. 94-109 (1998).

Tadjoedin E S, de Lange G L, Lyaruu D M, Kuiper L and Burger E H. High concentrations of bioactive glass material (BioGran) vs. autogenous bone for sinus floor elevation. *Clin Oral Implants Res.* 13:428-436 (2002).

Tyler J. E., Comparitive dissolution studies on human enamel and fluorapatite. *Caries Res* 4 1, pp. 23-30 (1970).

Underwood E J. *Trace elements in human and animal nutrition, 4$^{th}$ edition.* London: Academic Press; 196 (1977).

Vandenburgh H H, Hatfaludy S, Karlisch P, Shansky J., Mechanically induced alterations in cultured skeletal muscle growth, *J Biomech.* 1991; 24 Suppl 1:91-9.

Winn, S. R., Randolph, G., Uludag, H., Wonng, S. C., Hair, G. A. and Hollinger, J. O., 1999. Establishing an immortalized human osteoprecursor cell line: OPC-1. J. Bone Mineral Res. 14: 1721-1733.

Yamada, H. Strength of Biological Materials, Baltimore Md., Williams & Wilkins. 1970, Yaszemski M J, Payne R G, Hayes W C, Langer R and Mikos A C. Evolution of bone transplantation: molecular, cellular and tissue strategies to engineer human bone. *Biomaterials.* 17:175-185 (1996).

Zerbo I R, Bronckers A L, de Lange G L, van Beek G J and Burger E H. Histology of human alveolar bone regeneration with a porous tricalcium phosphate. A report of two cases. *Clin Oral Implants Res.* 12:379-384 (2001).

Example 10

Influence of MgO, ZnO and SiOs in Calcium Phosphate Based Resorbable Ceramics

Example Summary.

This Example investigates and disclosed the influence of dopants on the physical, mechanical and biological properties of tri calcium phosphate (TCP) resorbable ceramics with special emphasis towards in vitro strength degradation and cell-materials interactions as a function of time. For this purpose, 3-TCP was doped with magnesia (MgO), zinc oxide (ZnO) and silica ($SiO_2$). Those dopants were added as individual dopants, and their binary and ternary compositions. It was found that these dopants significantly influenced densification behavior and as sintered microstructures of TCP. In vitro mineralization studies in simulated body fluids (SBF) for 12 weeks showed apatite growth on the highly porous compositions either on the surface or inside. From SEM analysis it was evident that surface degradation occurred on all compositions in simulated body fluid (SBF). Compression strengths for samples up to 12 weeks in SBF showed that it is possible to tailor strength loss behavior through compositional modifications. The highest compression strength was found for binary MgO—ZnO doped TCP. Overall, samples showed either a similar strength level during the 12 weeks test period, or a continuous decrease or a continuous increase in strength depending on dopant chemistry or amount. In vitro human osteoblast cell culture was used to determine influence of dopants on cell-materials interactions. All samples were non-toxic and biocompatible. Dopant chemistry also influenced adhesion, proliferation and differentiation of OPC1 cells on these matrices.

Example Overview.

Figure 17:
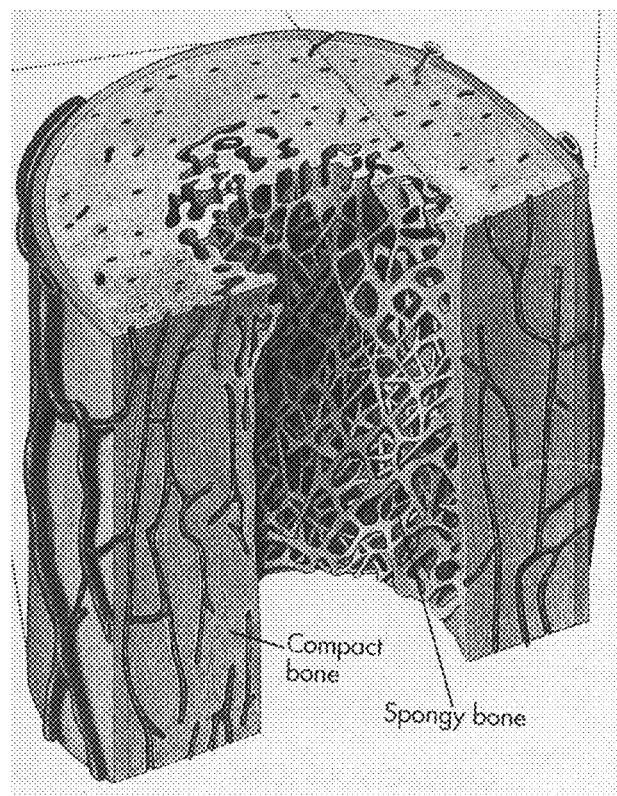
FIG. 17 shows a schematic diagram of human bone.

Human bone consists of a calcium phosphate-based inorganic phase, collagen polymer phase and water. In addition, ions like $Na^+$, $Mg2^+$, $K^+$ and $F^-$ are also present in traces. Bones are classified as "compact bone" or cortical bone that has low porosity, and "spongy bone" or cancellous bone with high porosity. The cortical bone consists of cylindrical channels i.e., osteons that are held together by a framework of hard tissue, mainly hydroxyapatite (HAp) crystals. Cylindrical fibers of collagen, the major organic component of bone, fill the pores of these bones, which are typically between 190-230 μm in size. The inorganic matrix of the cancellous bone consists of a porous structure with an interconnected porosity of ~65 volume %.[2-3] FIG. 17 shows a schematic diagram of human bone.

Figure 18:
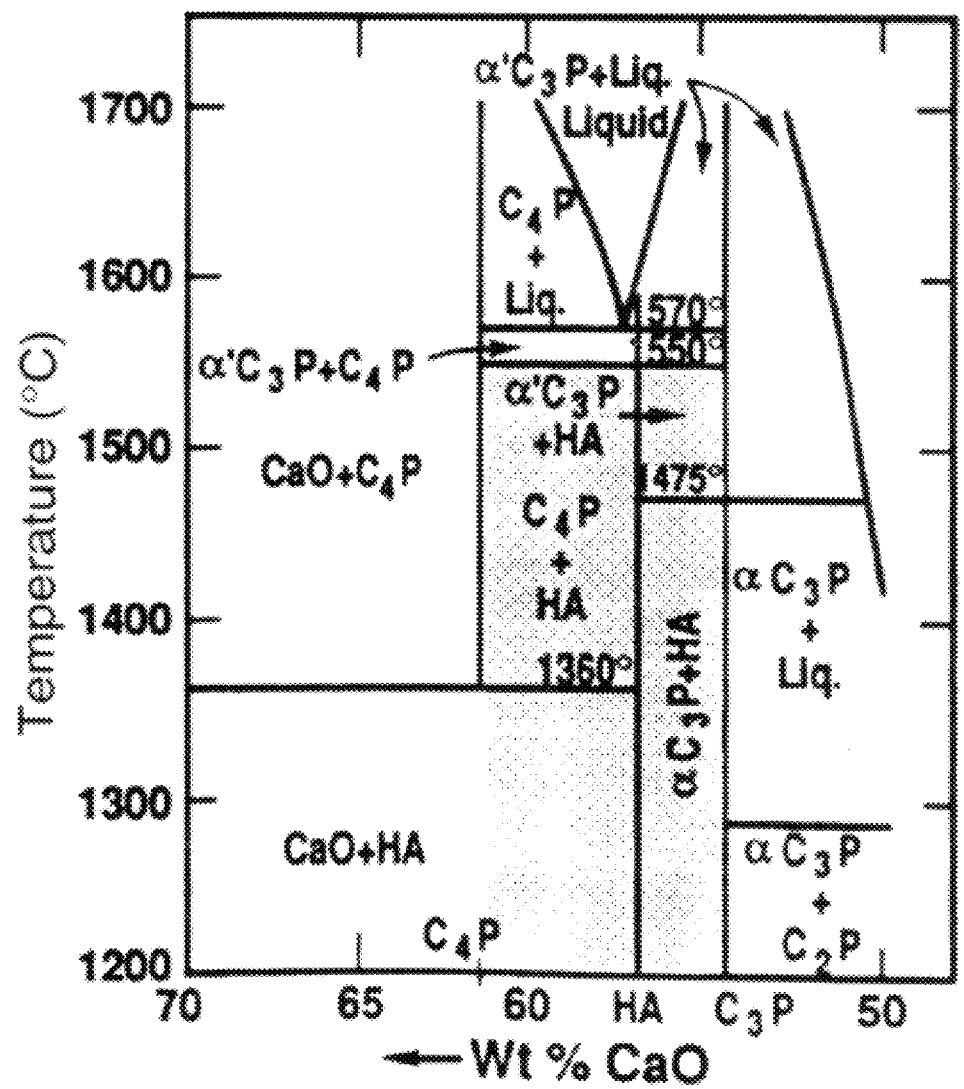
FIG. 18 shows, according to particular exemplary aspects of the present invention, tha calcium phosphates also exist in different phases depending on temperature, impurities and the presence of water.

Calcium-to-phosphorus ratio in naturally occurring bone mineral is close to 1.67 to 1. CaPs can be bio-active i.e., implants are osteoconductive, and implant materials have a very slow degradation rate in vivo; or bio-resorbable i.e., implant not only osteoconductive, but also degrades in vivo. Of particular interest are those with calcium-to-phosphorus ratios between 1.5:1 (Tricalcium phosphate, TCP, ($Ca_3(PO_4)_2$)) and 1.67:1 (Hydroxyapatite, $Ca_m(PO_4)_6(OH)_2$, Hap). Calcium phosphates also exist in different phases depending on temperature, impurities and the presence of water and shown in FIG. 18 and TABLE 3.[9] In FIG. 18, the binary equilibrium phase diagram between CaO and P2O5 gives an indication of the compounds formed between the two oxides. Among them, two phases that are stable at body temperature and in contact with body fluid are dicalcium phosphate ($CaHPO_4.2H_2O$) at pH<4.2, and HAp at pH>4.2. Since human blood stays in a very narrow pH range ~7.3, clearly, HAp is the stable phase 18 in that pH. TABLE 3 also shows solubility of different calcium phosphate phases and it can be seen that increasing Ca to phosphorous ratio reduces the solubility product or reduces the rate of degradation of these materials in vivo.

TABLE 3

Main Ca—P compounds use as surgical materials[9]

| Chemical name | Usual Symbol | Chemical Formulation | Mineral name | Atomic Ratio Ca/P | Space Group | Solubility Product |
|---|---|---|---|---|---|---|
| Monocalcium phosphate | MCP | $Ca(H_2PO_4)_2 \cdot H_2O$ | — | 0.50 | — | $1.0 \times 10^{-3}$ |
| Dicalcium phosphate dihydrate | DCPD | $CaHPO_4 \cdot 2H_2O$ | Brushite | 1.00 | 2/m | $1.87 \times 10^{-7}$ |
| Dicalcium phosphate | DCP | $CaHPO_4$ | Monetite | 1.00 | P1 | $1.26 \times 10^{-7}$ |
| Octocalcium phosphate | OCP | $Ca_8H_2(PO_4)_6 \cdot 5H_2O$ | — | 1.33 | — | $5.01 \times 10^{-15}$ |
| Tricalcium phosphate | TCP | $Ca_3(PO_4)_2$ | — | 1.50 | R3c | $2.83 \times 10^{-30}$ |
| Hydroxyapatite | HAP | $Ca_{10}(PO_4)_6(OH)_2$ | Hydroxyapatite | 1.67 | $P6_3/m$ | $2.35 \times 10^{-59}$ |
| Tetra-calcium phosphate | TTCP | $Ca_4O(PO_4)_2$ | — | 2.00 | $P2_1$ | — |

Properties of calcium phosphate (CaP) ceramics also vary significantly as a function of porosity, composition and phase. TABLE 4 summarizes properties of various CaP phases with different levels of porosity.[2] Unfortunately, synthetic CaPs do not show similar mechanical and biological properties as in bone.

TABLE 4

Mechanical properties and strength of calcium phosphate ceramics[2]

| Material | Porosity (%) | Density (mg/m$^3$) | Young's Modulus (GPa) | Microhardness (GPa) | Compressive strength (MPa) | Tensile Strength (MPa) | Flexural Strength (MPa) |
|---|---|---|---|---|---|---|---|
| HA | 0.1-3 | 3.05-3.15 | 7-13 | 4.2-4.5 | 350-450 | 38-48 | 100-120 |
|  | 10 | 2.7 | — | 4.2 | — | — | — |
|  | 30 | — | — | — | 120-170 | — | — |
|  | 40 | — | — | — | 60-120 | — | 15-35 |
|  | 2.8-19.4 | 2.55 | 44-88 | — | 310-510 | — | 60-115 |
|  | 2.5-26.5 | 3.07 | 55-110 | — | ≤800 | — | 50-115 |
| TTCP | Dense | 3.1 | — | — | 120-200 | — | — |
| TCP | Dense | 3.14 | — | — | 120 | — | — |
|  | 36 | — | — | — | 7-21 | 5 | — |
| Other Ca—Ps | Dense | 2.8-3.1 | — | — | 70-170 | — | — |

The present Example is focused primarily on tricalcium phosphate based resorbable ceramics. The chemical formula for tricalcium phosphate (TCP) is $Ca_3(PO_4)_2$. TCP has four polymorphs, α, β, γ, and super-α. The γ polymorph is a high-pressure phase, and the super-α phase is observed at temperatures above 1500° C.[13] Hence, the most frequently observed polymorphs of TCP bioceramics are the alpha and beta phases. α-TCP crystal is in the monoclinic space group $P2_1/α$ with lattice parameters a=1.2887 nm, b=2.7280 nm, c=1.5219 nm, and β=126.20 degrees. β-TCP has the rhombohedral space group R3c with unit cell a=1.0439 nm, c=3.7375 nm (hexagonal setting) with 21 formula units per hexagonal unit cell. β-TCP is stable up to 1125° C., but above this temperature and up to 1430° C., α-TCP becomes the stable phase.[14] For β-TCP, biodegradation has been reported to be incomplete even after 9.5 months after grafting in the human mandible. Histological examination of these biopsies revealed that 34% of the biopsy consisted of mineralized bone tissue and 29% of remaining β-TCP.[15]

According to particular aspects of the present invention, resorbable characteristics of CaPs can be tailored by adding trace elements that are already present in physiological environment. This Example investigates the influence of these trace elements on biodegradation behavior of calcium phosphates.

Influence of MgO, ZnO and SiOs in Calcium Phosphate Based Resorbable Ceramics:

A group of trace elements was initially selected for investigate; namely, $Zn^{2+}$, $Mg^{2+}$, $Si^{2+}$, $Na^+$, $Ag^+$, $Ti^{4+}$ and $F^-$, and among these metal ions, the cell-materials interactions and influence of $Zn^{2+}$, $Mg^{2+}$ and $Si^{2+}$ are reported in this Example. In this Example, at a constant Ca:P ratio of 1.5:1, the $Zn^{2+}$, $Mg^{2+}$ and $Si^{2+}$ contents were varied and physical, mechanical and biological properties of those compositions were studied. The following section summarizes the significance of some of these ions on bone formation and biodegradation. TABLE 5 lists specific compositions of different dopants that were used in this study.

TABLE 5

Compositions, average grain size and sintered densities of different combination of dopants used

| Compositions (wt %) | Average Grain Size (μm) | Sintered density (g/cc) | % Sintered density (Normalized) |
|---|---|---|---|
| TCP | 4.59 +/− 0.4 | 2.25 +/− 0.07 | 73.2 |
| TCP-1 SiO$_2$ | 3.85 +/− 0.3 | 2.32 +/− 0.09 | 75.6 |
| TCP-1% MgO | 6.40 +/− 0.5 | 2.28 +/− 0.09 | 74.2 |
| TCP-0.25% ZnO | 4.07 +/− 0.4 | 2.13 +/− 0.11 | 69.5 |
| TCP-1% SiO$_2$—0.25% ZnO | 4.22 +/− 0.4 | 2.47 +/− 0.05 | 80.35 |
| TCP-1% SiO$_2$—1% MgO | 4.99 +/− 0.3 | 2.51 +/− 0.05 | 81.7 |
| TCP-0.25% ZnO—1% MgO | 4.30 +/− 0.4 | 2.49 +/− 0.04 | 81.1 |
| TCP-1% SiO$_2$—1% MgO—0.25% ZnO | 3.89 +/− 0.3 | 2.55 +/− 0.04 | 83.1 |
| TCP-5 wt % SiO$_2$ | 5.43 +/− 0.5 | 2.35 +/− 0.07 | 76.4 |

Figure 19:
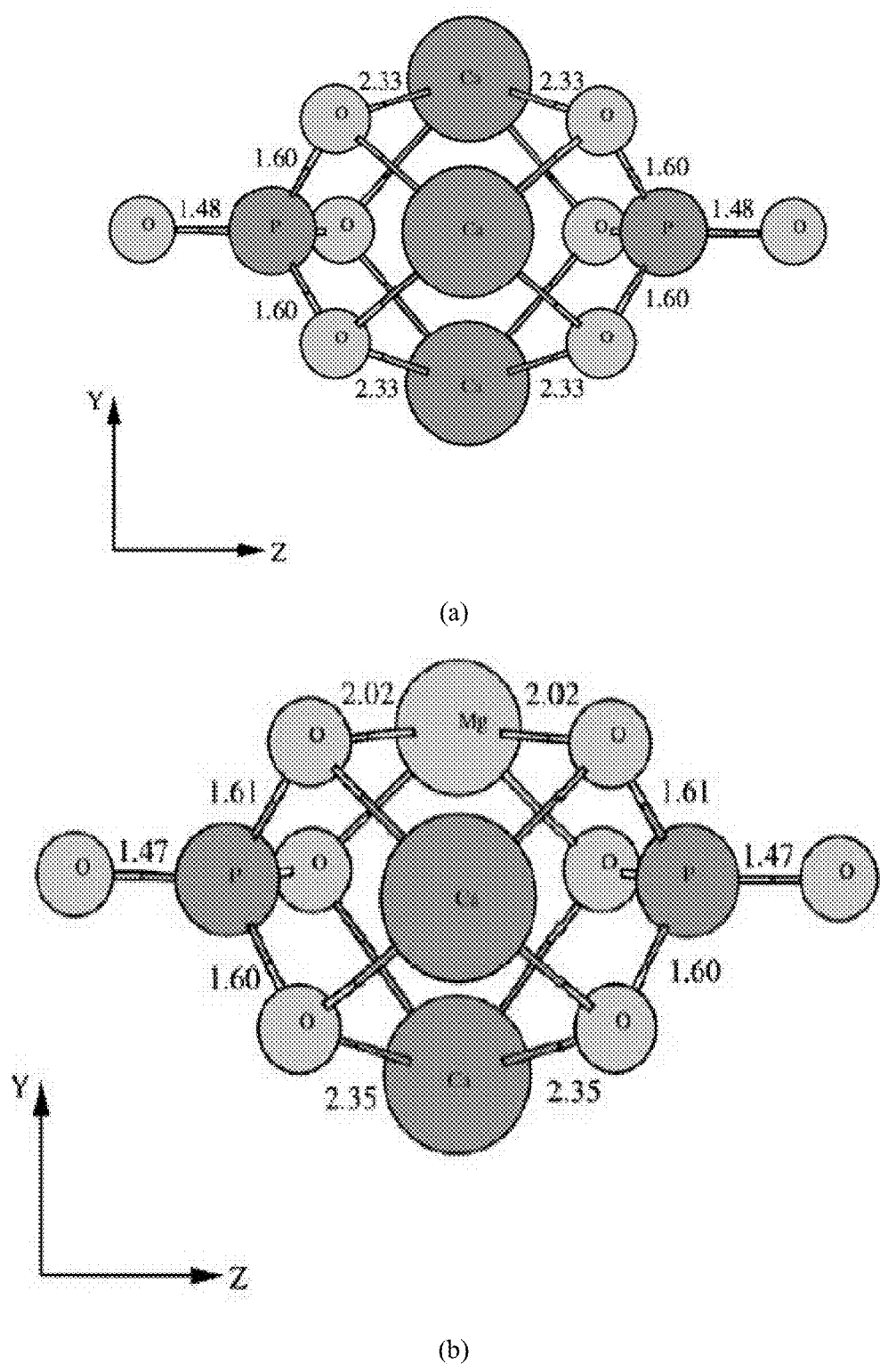
FIG. 19 shows, according to particular exemplary aspects of the present invention, equilibrium inter-atomic distances (Å) and bond angles (degree) of (a) fully relaxed Ca$_3$(PO$_4$)$_2$ (TCP) fragment (b) fully relaxed MgCa$_{3-1}$(PO$_4$)$_2$ fragment.

Magnesium:

TABLE 6 shows the atomic radii of atoms in TCP and the dopants used. Magnesium (Mg) is undoubtedly one of the most important bivalent ions associated with biological apatites.[23-24] In calcified tissue, the amount of Mg is higher with the apatitic phase at the beginning of the calcification process and decreases with increasing calcification.[25] There is growing evidence that Mg depletion adversely affects all stages of skeletal metabolism, causing cessation of bone growth, decreased osteoblastic and osteoclastic activities and bone fragility.[26] Mg is substituted into tri-calcium phosphate in the formula $Mg_xCa_{3-x}(PO_4)_2$ (x=1, 2, and 3).[27] Because of the smaller ionic radius, Mg atoms reside closer to the axis of the cluster than the Ca atoms. When a Mg atom is substituted into the TCP structure the Mg—O bond becomes stronger whereas, the Ca—O bonds are weakened by the increase in bond length compared to the Mg—O interaction, which may be the reason for Mg stabilizing the structure of TCP.[27] FIG. 19 shows equilibrium inter-atomic distances (Δ) and bond angles (degree) of (a) fully relaxed $Ca_3(PO_4)_2$ (TCP) fragment (b) fully relaxed $MgCa_{3-1}(PO_4)_2$ fragment.

TABLE 6

Atomic radii of atoms in TCP and the dopants used

| Element | Atomic radius (pm) 10$^{-12}$ |
|---|---|
| Calcium (Ca) | 197 |
| Phosphorous (P) | 98 |
| Oxygen (O) | 73 |

TABLE 6-continued

Atomic radii of atoms in TCP and the dopants used

| Element | Atomic radius (pm) $10^{-12}$ |
|---|---|
| Magnesium (Mg) | 160 |
| Zinc (Zn) | 134 |
| Silicon (Si) | 117.6 |

Zinc:

Zn is an essential trace element with stimulatory effects on bone formation in vitro and in vivo. Zinc contents ranges from 0.012 to 0.025 wt % in human bone, which is relatively higher than Zn content in adult soft tissues and plasma.[28-29] In vitro studies showed that Zn has direct specific proliferative effect on osteoblastic cells[30] and a potent and selective inhibitory effect on osteoclastic bone resorption.[31-32] In vivo studies on Zn doped calcium phosphates on rabbit femora showed over 50% more newly formed hone over undoped calcium phosphate composition. Recent studies also linked clinical relationship between osteoporosis and Zn deficiency in elderly subjects.[33] Our preliminary research showed that Zn addition increases sinter densification and hardness of HAp and TCP ceramics.[34] In TCP, Zn replaces the Ca atom causing some distortion in the crystal structure and is believed to be the reason for improved bioactivity in TCP.[35] Similar to Mg addition, Zn addition also changes the equilibrium inter-atomic distances (Å) and bond angles.[27]

Silicon:

Si is an important trace element in bone formation and calcification. Localized Si is found in active bone growth areas in young mice and rats using electron microprobe studies.[36] It was also found that Si plays an important role during the apatite phase nucleation in forming surface apatite layers for silica containing glasses.[37] It was reported that up to 2 wt % of Si does not cause any calcium silicate phase formation and is considered optimum. In vitro studies also suggested that addition of up to 9 wt % of $SiO_2$ enhances osteoblastic differentiation and has higher potency for enhance osteogenesis.[38-39]

Methods:

Sample Preparation:

High purity oxide based sintering additives included silicon dioxide (99%+ purity), magnesium oxide (96%+ purity) and zinc oxide (99.9%+ purity) were purchased from 18 Fisher Scientific. Synthetic beta-tricalcium phosphate (BABI-TCP-N100) nano powder was obtained from Berkley Advanced Biomaterials Inc. (CA) with an average particle size of 100 nm. Powders were weighed and mixed in 250 mL polypropylene Nalgene bottles, with 150 g of 5 mm diameter zirconia milling media. Batches were made based on 30 g of β-TCP. After dopant addition, ball milling was done for 6 h at 70 rpm to minimize the formation of agglomerates and increase the homogeneity of the powders. After milling, powders were measured for each composition and pressed using a uniaxial press. There were two types of samples made: disk compacts for biological analysis and compression compacts for mechanical analysis. The amount of powder weighed to make disk compacts was 0.5 g and the same for compression compacts was 1.15 g. The disk mold press produced 12 mm in diameter by 3 mm thick green compacts while the compression mold press made 6.3 mm diameter by 20 mm long green compacts. Disk samples were uniaxially pressed at 25 MPa of pressure whereas the compression compacts were pressed at 15 MPa. At least, five samples were made from individual compositions for each type of analysis. After pressing, all green compacts were placed in a muffle furnace for densification at 1250° C. for 2 h. Bulk densities for green and sintered samples were measured for all compositions.

Phase Analysis:

X-ray diffraction was used to test any phase changes to the starting powders after the introduction of dopants. Powdered samples were prepared from sintered compositions in a mortar and a pestle. Phase analysis was done with a Philips PW 3040/00 X'pert MPD system at room temperature using $Co-K_\alpha$ radiation with a Ni-filter. All runs were carried out over a 2θ range from 20° to 70° at a step size of 0.02° (2θ) and a count time 0.5 sec per step. No significant phase change was noticed in all of these sintered compositions.

Microstructural Analysis:

Scanning electron microscopy was used to analyze microstructure of pure and doped sintered β-TCP structures. All compositions were observed under SEM to study the effect of dopants on the microstructure of β-TCP. Microstructural degradation was also observed as a function of time in SBF. Both top surface and fracture surface SEM were taken for all samples.

Mineralization and Controlled Strength Loss Behavior:

Bioactivity of pure and doped TCP samples was evaluated by immersion in simulated body fluid (SBF), which has a similar composition as of human blood plasma. The solution was prepared by dissolving NaCl, KCl, $NaHCO_3$, $MgCl_2.6H_2O$, $CaCl_2.2H_2O$, $Na_2SO_4.10H_2O$ and $K_2HPO_4$ into distilled water and buffered at pH 7.35 with tris-hydroxymethyl aminomethane (TRIS) and 1 (N) HCl at 37° C.[40] Samples were immersed in the glass vial containing 10 ml of SBF solutions and were kept under static conditions inside a biological thermostat at 37° C. for 2, 4, 6, 8, and 12 weeks. SBF solution was changed twice per week with freshly made solutions. All experiments were performed in triplicate, by running three independent glass vials simultaneously. After exposure, samples were washed with distilled water and dried at 200° C. for 72 h. After drying all samples were weighted and compared with their dry weight prior to immersion.

Mechanical properties of as-sintered structures with various dopants were tested under compressive loading and compared with undoped sample. Compressive strengths of these samples were evaluated using a screw driven Instron with a constant crosshead speed of 0.33 mm/min. Pieces of the broken samples were collected for fractography under SEM. Compression strengths from as processed and SBF treated samples showed the strength degradation behavior of these resorbable ceramic compositions.

Cell Culture:

All samples were sterilized by autoclaving at 121° C. for 20 min. In this study the cells used were an immortalized, cloned osteoblastic precursor cell line 1 (OPC1), which was derived from human fetal bone tissue.[41] OPC1 cells were seeded onto the samples and then placed in 24-well plates. Cell density was $2.0 \times 10^4$ cells/well. 1 ml of McCoy's 5A medium (enriched with 5% fetal bovine serum, 5% bovine calf serum and supplemented with 4 µg/ml of fungizone) was added to each well. Cultures were maintained at 37° C. under an atmosphere of 5% CO). Medium was changed every 2-3 days for the duration of the experiment.

MTT Assay:

The MTT assay (Sigma, St. Louis, Mo.) was performed to assess cell proliferation. The MTT solution of 5 mg/ml was prepared by dissolving MTT in PBS, and filter sterilized. The MTT was diluted (50 µl into 450 µl) in serum free, phenol red-free Dulbeco's Minimum Essential medium (DME). 500 μl diluted MTT solution was then added to each sample in 24-well plates.

After 2 h incubation, 500 μl of solubilization solution made up of 10% Triton X-100, 0.1N HCl and isopropanol were added to dissolve the formazan crystals. 100 μl of the resulting supernatant was transferred into a 96-well plate, and read by a plate reader at 570 nm. Data are presented as mean±standard deviation. Statistical analysis was performed using Student's t-test, and P<0.05 was considered statistically significant.

Morphology of OPC1 Cells on Samples:

All samples for SEM observation were fixed with 2% paraformaldehyde/2% glutaraldehyde in 0.1M cacodylate buffer overnight at 4° C. Post-fixation was performed with 2% osmium tetroxide ($OsO_4$) for 2 h at room temperature. The fixed samples were then dehydrated in an ethanol series (30%, 50%, 70%, 95% and 100% three times), followed by a hexamethyldisilane (IIMDS) drying procedure. After gold coating, the samples were observed by SEM.

Immunocytochemistry and Confocal Microscopy:

Samples bearing cells were fixed in 4% paraformaldehyde in 0.1M phosphate buffer. Those samples were stored at 4° C., for future use. After rinsing in Triton X-100 for 10 min, samples were blocked with TBST/BSA (tris-buffered saline with 1% bovine serum albumin, 250 mM NaCl, pH 8.3) for 1 h. Primary antibody against alkaline phosphate (ALP) or vinculin (Sigma, St. Louis, Mo.) was added at a 1:100 dilution and incubated at room temperature for 2 h. The secondary antibody, goat anti-mouse (GAM) Oregon green (Molecular Probes, Eugene, Oreg.), was added at a 1:100 dilution and incubated for 1 h. Samples were then mounted on coverslips with Vectashield® Mounting Medium (Vector Labs, Burlingame, Calif.) with propidium iodide (PI) and observed using a confocal scanning laser microscopy (Bio-Rad 1024 RMC).

Figure 20:
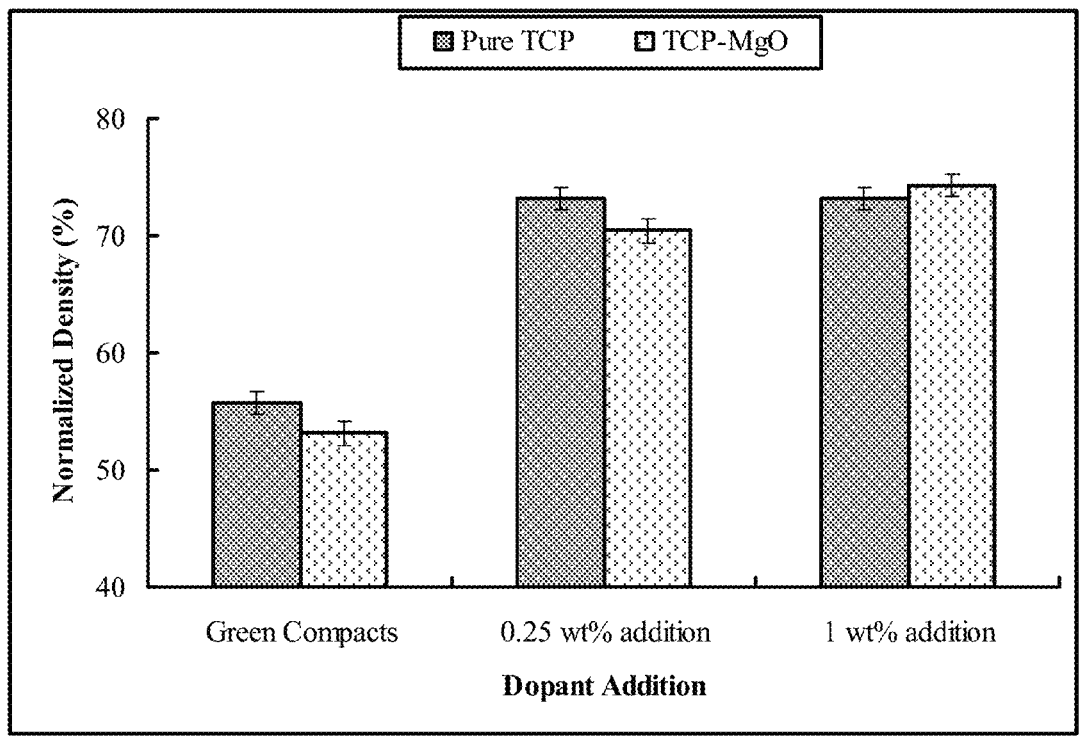
FIG. 20 shows, according to particular exemplary aspects of the present invention, influence of MgO addition on densification of TCP based on 0.25 wt % and 1 wt % and compared to undoped TCP.
Figure 21:
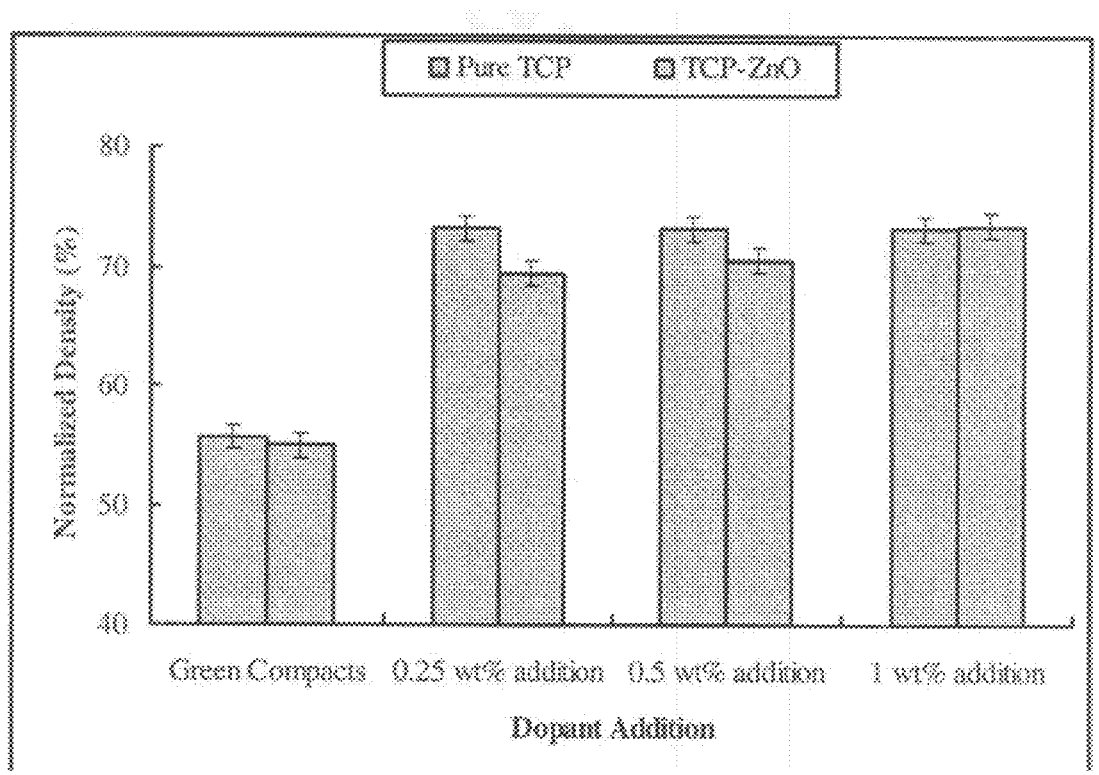
FIG. 21 shows, according to particular exemplary aspects of the present invention, influence of ZnO addition on densification of TCP based on 0.25, 0.5 and 1 wt % and compared to undoped TCP.
Figure 22:
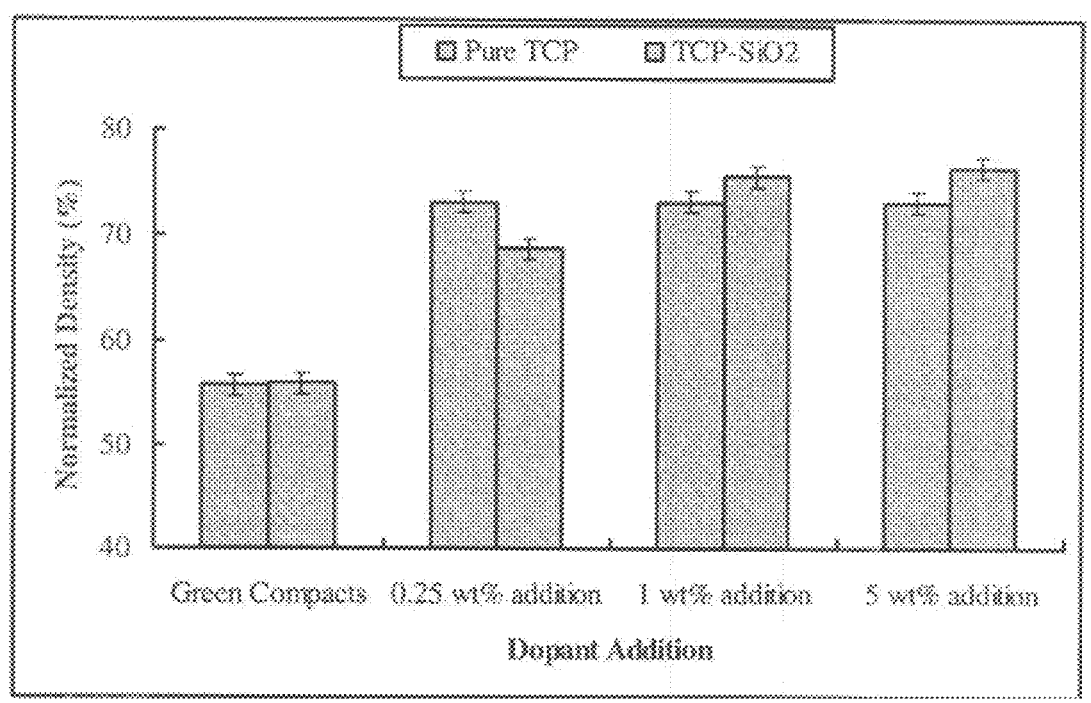
FIG. 22 shows, according to particular exemplary aspects of the present invention, influence of SiO$_2$ addition on densification of TCP.

Results:

Density:

Density measurement was used to identify the amount of dopants to be used for each composition of TCP with MgO, ZnO and $SiO_2$. Green and sintered densities were measured and were normalized with respect to the theoretical density of β-TCP (3.07 g/cc). FIG. 20 shows influence of MgO addition on densification of TCP based on 0.25 wt % and 1 wt % and compared to undoped TCP. Clearly, 1 wt % addition lead to higher density compared to 0.25 wt % of MgO in TCP, and 1 wt % was used for all further studies. Similarly, FIG. 21 shows influence of ZnO addition on densification of TCP based on 0.25, 0.5 and 1 wt % and compared to undoped TCP. Though the highest density was observed for 1 wt % addition, some concerns were raised regarding cytotoxicity of Zn doped compositions higher than 0.33 wt %,[42] therefore, for all our further experiments, only 0.25 wt % composition was considered. FIG. 22 shows influence of $SiO_2$ addition on densification of TCP. It can be seen that densification increased at 1 wt % and continued up to 5 wt %. Based on this data, for single component, we have studied both 1 and 5 wt % $SiO_2$ effect on TCP, however, for binary and ternary dopant systems, we have used only 1 wt % SiO2. TABLE 5 (herein above) shows different compositions that were studied. TABLE 5 also shows sintered densities for the disc samples of all of those compositions. Apart from density, influence those dopants on microstructure, compressive strength, mineralization in SBF, weight change in SBF and strength degradation in SBF up to 12 weeks were studied. Human osteoblast (HOB) cell-materials interactions as well as adhesion and differentiation protein expressions were studied with a select group of samples.

Figure 23:
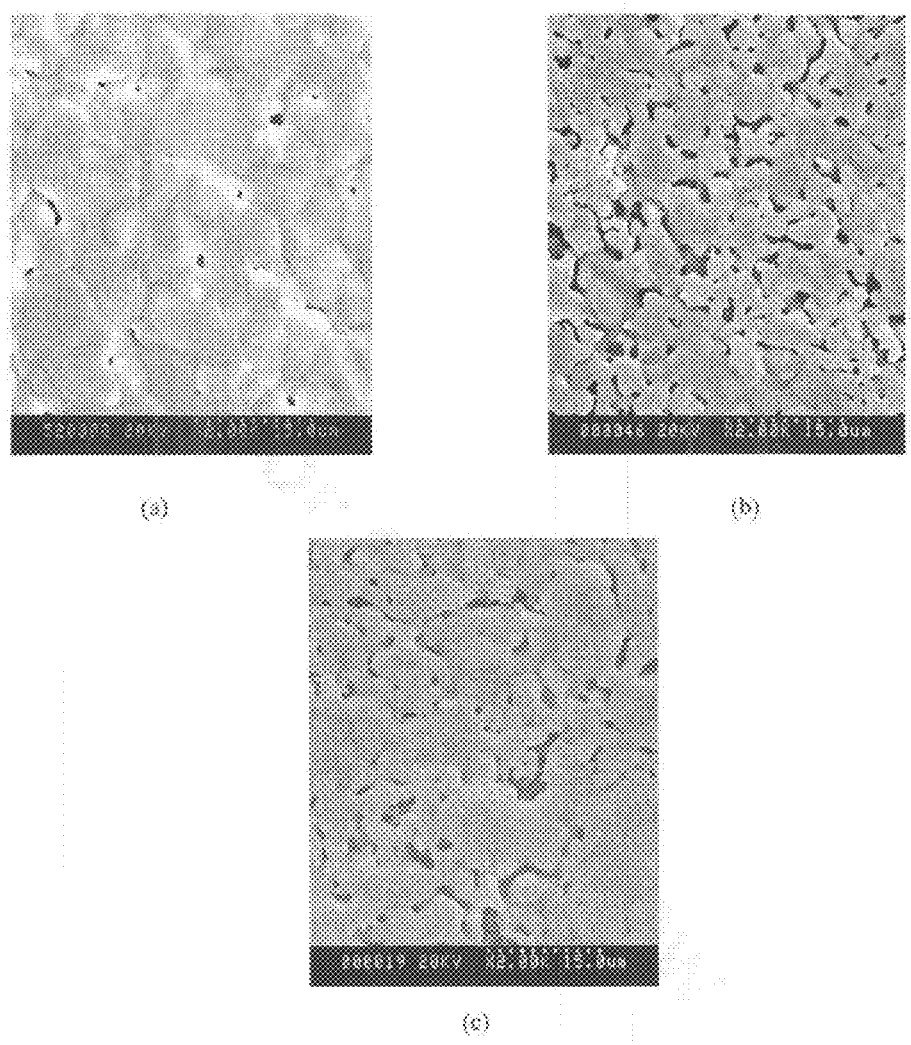
FIG. 23 shows, according to particular exemplary aspects of the present invention, as received and SBF degraded microstructures of pure TCP ceramics.
Figure 24:
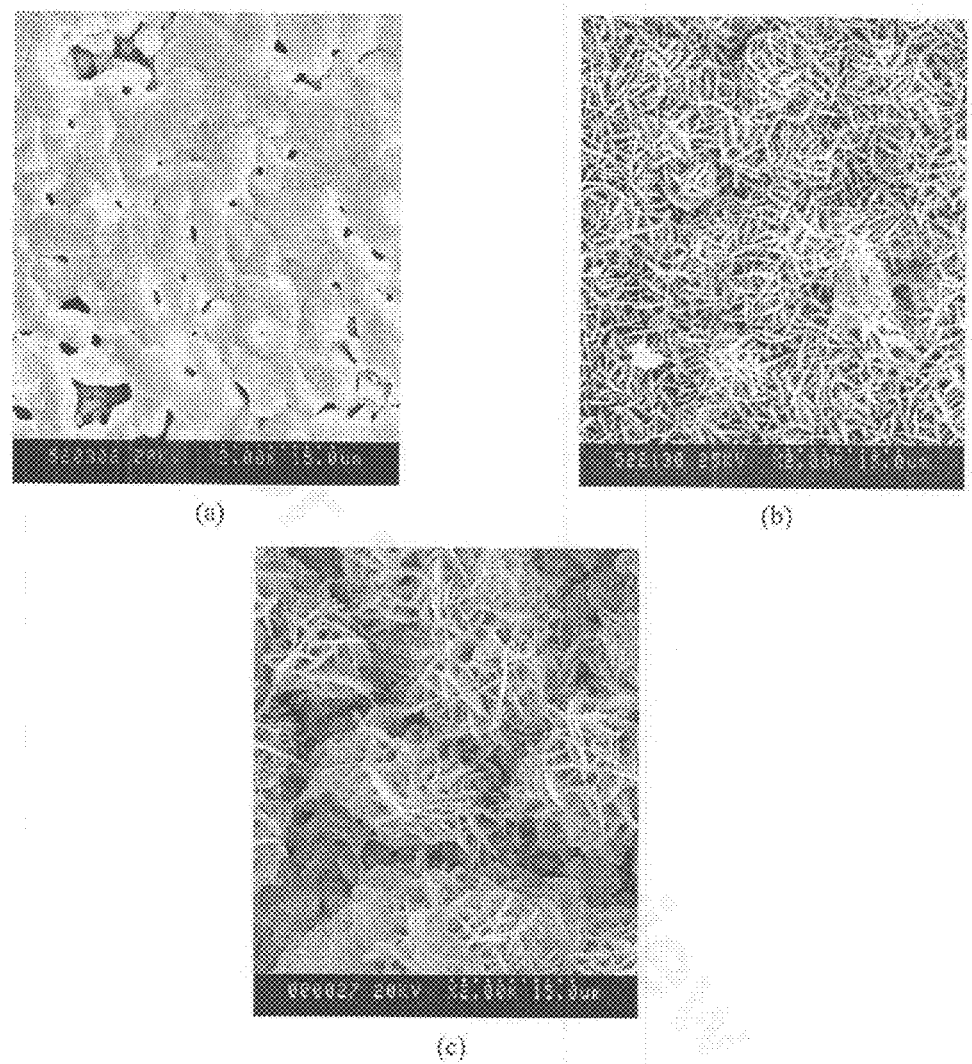
FIG. 24 shows, according to particular exemplary aspects of the present invention, microstructures of TCP-1 wt % SiO$_2$.
Figure 25:
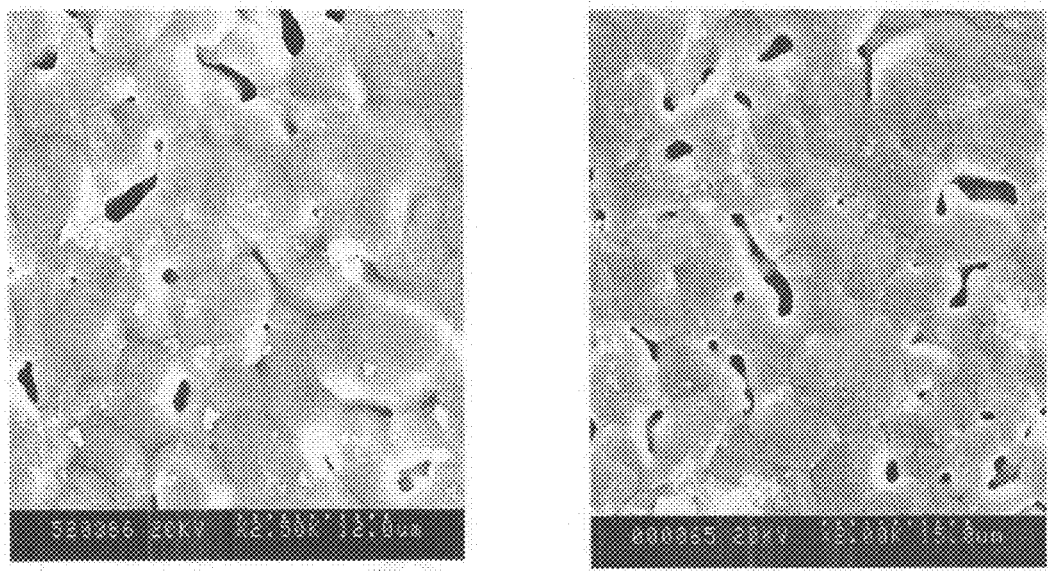
FIG. 25 shows, according to particular exemplary aspects of the present invention, microstructures of TCP-5 wt % SiO2 only up to 6 weeks in SBF. No apatite formation is visible on the surface and grain structure remains somewhat distinct throughout the 6 week period.
Figure 26:
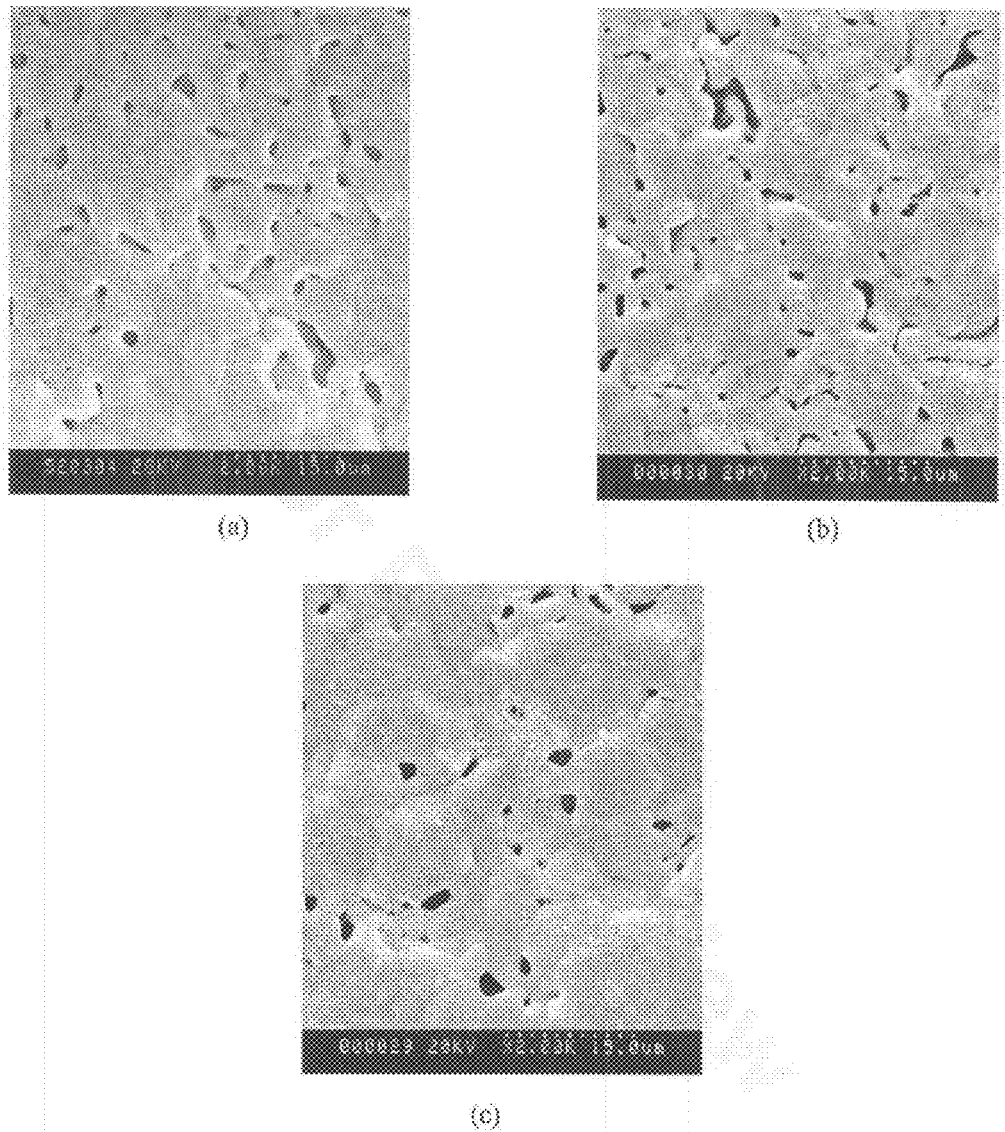
FIG. 26 shows, according to particular exemplary aspects of the present invention, surface microstructures of TCP-ZnO composition that is changed very little throughout the experiment. Very little surface apatite layer formation is also noticed, though some apatite can be seen inside the sample from fracture surface analysis.
Figure 27:
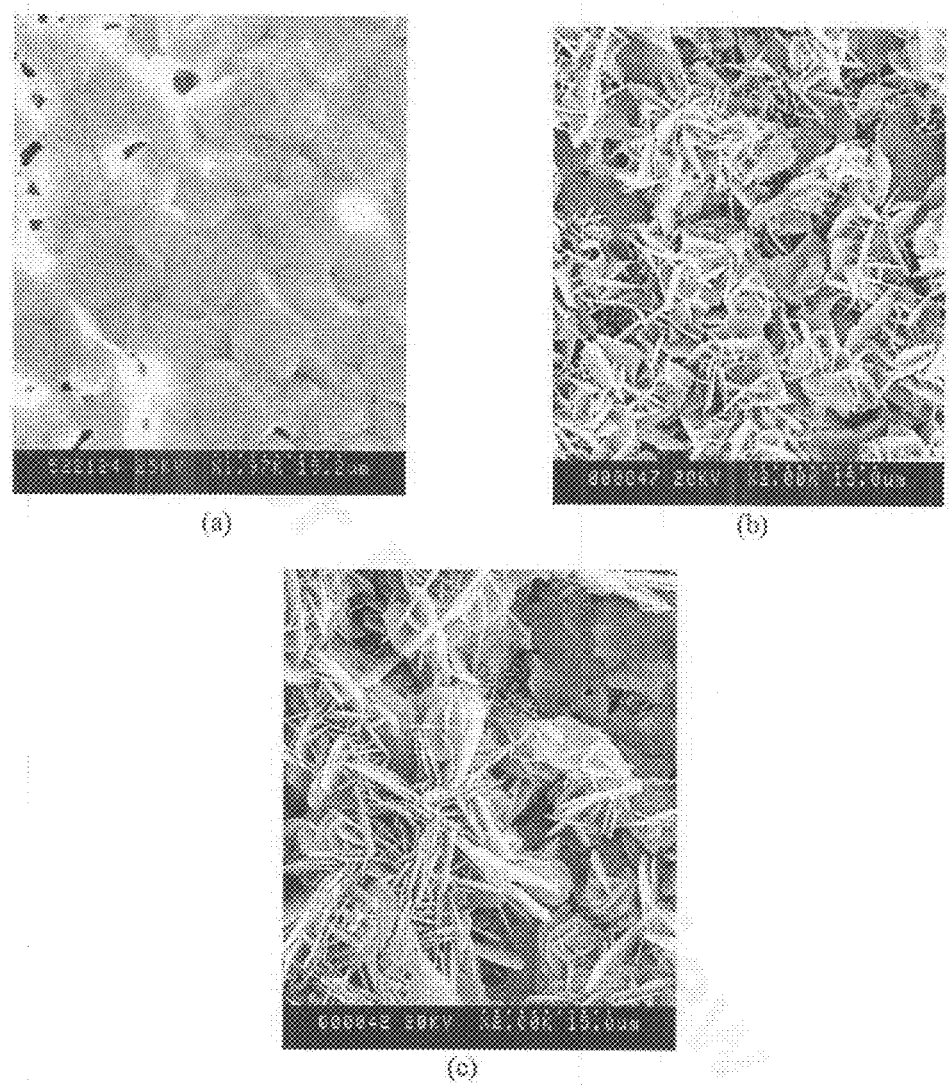
FIG. 27 shows, according to particular exemplary aspects of the present invention, TCP-MgO composition, which also showed the highest starting grain size. A unique crystal-like apatite formation on the surface microstructure is observed up to 8 weeks, which are similar to the octacalcium phosphate (OCP) crystals found by the electrochemical method.
Figure 28:
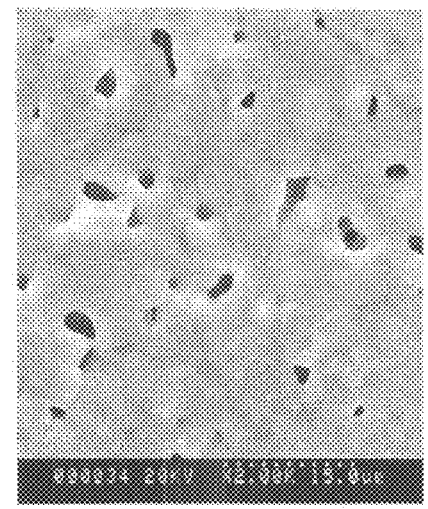
FIG. 28 shows, according to particular exemplary aspects of the present invention, microstructures of binary and ternary dopants after 12 weeks. Overall, no apatite formation can be seen at the top surface for all of these compositions.
Figure 28:
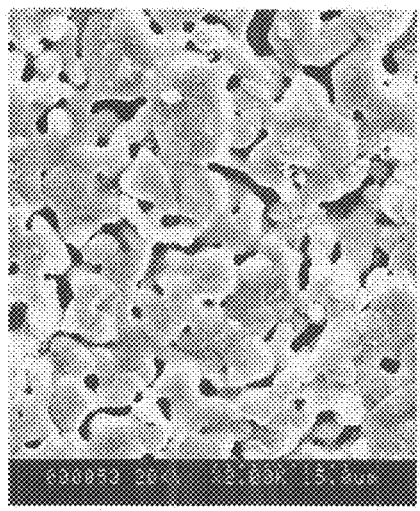
Figure 28:
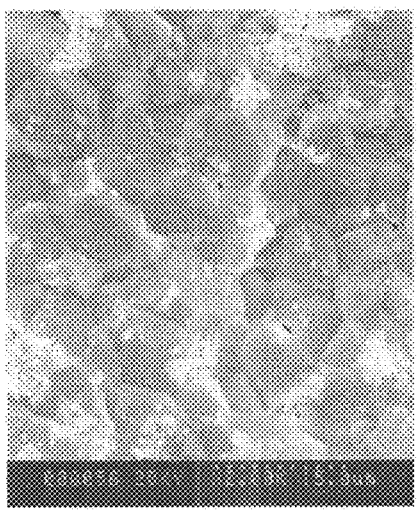
Figure 28:
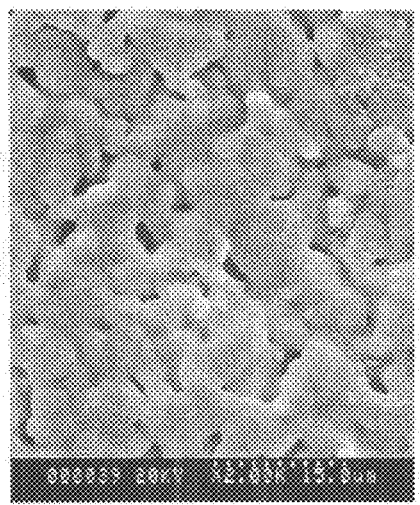

Microstructure:

All as sintered compositions were studied using SEM to understand the influence of dopants effect on microstructure. Microstructural degradation was also studied for samples after immersion in SBF for 2, 4, 8 and 12 weeks. All the starting grain sizes are given in TABLE 5. FIG. 23 shows as received and SBF degraded microstructures of pure TCP ceramics. Pure TCP microstructure is used as control to compare dopants effects. A well established pattern of degradation is observed over 12 weeks. There is significant increase in porosity from the initial stage to the final stage; which is an indication of dissolution. Though apatite formation is not evident on the top surface, interconnected pores are filled with these apatites, which are believed to be due to saturation effect from the local release of calcium and phosphorous ions in a semi-closed environment than the free surface. FIG. 24 shows microstructures of TCP-1 wt % $SiO_2$. Significant growth of flake-like apatite layer on the surface of the compacts can be seen from 2 weeks. With time, these flaky apatites grew in size and degraded the TCP grain structure. FIG. 25 shows microstructures of TCP-5 wt % SiO2 only up to 6 weeks in SBF. No apatite formation is visible on the surface and grain structure remains somewhat distinct throughout the 6 week period. Minimal surface porosity is observed with this composition. FIG. 26 shows surface microstructures of TCP-ZnO composition that is changed very little throughout the experiment. Very little surface apatite layer formation is also noticed, though some apatite can be seen inside the sample from fracture surface analysis. FIG. 27 shows TCP-MgO composition, which also showed the highest starting grain size. A unique crystal-like apatite formation on the surface microstructure is observed up to 8 weeks, which are similar to the octacalcium phosphate (OCP) crystals found by the electrochemical method.[43-44] These apatites are also seen in the pores. FIG. 28 shows microstructures of binary and ternary dopants after 12 weeks. Overall, no apatite formation can be seen at the top surface for all of these compositions. Also, MgO—ZnO doped binary composition is shown minimum degradation even after 12 weeks in SBF. Degradation in other compositions is evident through increase in surface porosity and loss of distinct grain structure.

Figure 29:
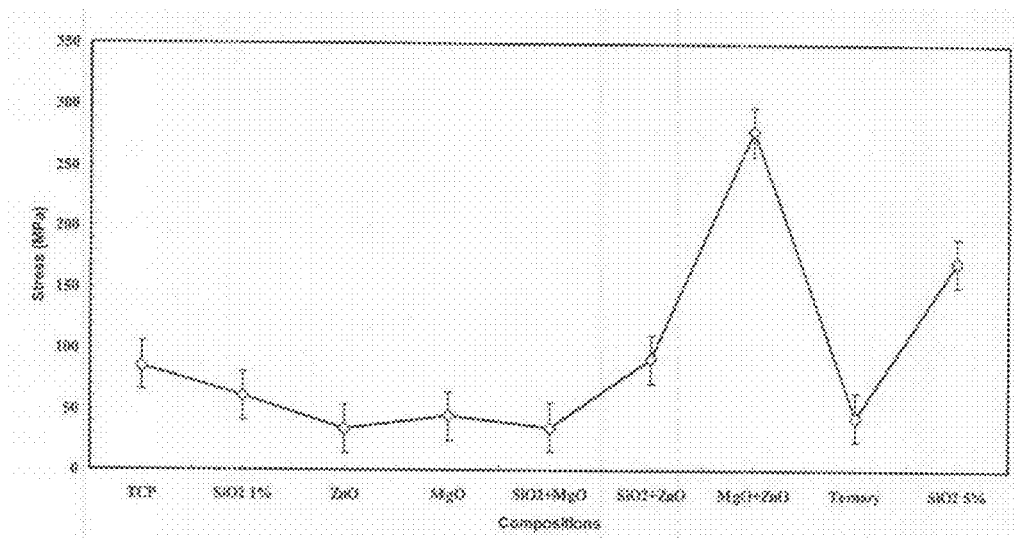
FIG. 29 shows, according to particular exemplary aspects of the present invention, compression strengths of as sintered samples. Most dopant additions actually dropped compressive strengths of sintered TCP even if a small increase in density can be seen for those compositions.

Mechanical Properties:

Mechanical properties of various dopant combinations incorporated into TCP structures were evaluated via uniaxial compression testing using a screw driven machine. Five samples of each composition were tested. In an average, sintered densities of compression samples were 5% below the disc sample density due to low green density of the pressed samples. FIG. 29 shows compression strengths of as sintered samples. Most dopant additions actually dropped compressive strengths of sintered TCP even if a small increase in density can be seen for those compositions. The lowest strength was found for ZnO doped samples while the highest strength was for MgO—ZnO doped samples. Over 200% increase in compressive strength was found due to the addition of 0.25 wt % ZnO and 1 wt % MgO. Similarly, over 100% increase in compressive strength was found for 5 wt % $SiO_2$ doped sample. The third set of samples that showed an increase in compressive strength was SiO2-ZnO, with a modest 30% increase. The results clearly show that the individual dopant effects on compressive strength may be significantly different compared to their combined effects. For example, just ZnO or MgO additions dropped the compressive strength of TCP, however, their combined addition increased the same over 200%. Phase analysis of all of these compositions didn't reveal formation of any significant separate phases. Therefore, the primary reason for strength variations can be related to grain boundary strengthening and change in densification.

Figure 30:
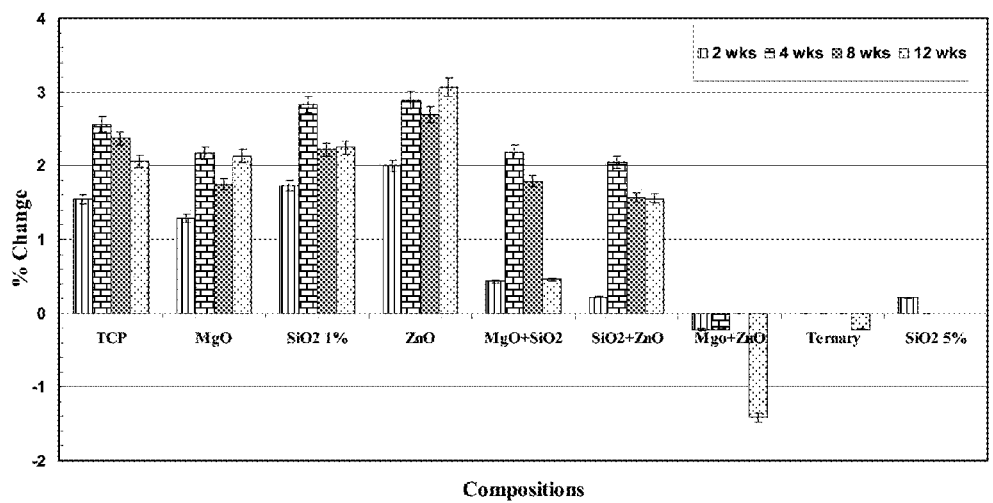
FIG. 30 shows, according to particular exemplary aspects of the present invention, weight change as a function of composition up to 12 weeks. Except MgO—ZnO and the ternary compositions, all other cases a modest weight increase between 1-3% of their as starting sintered weight can be seen.
Figure 31:
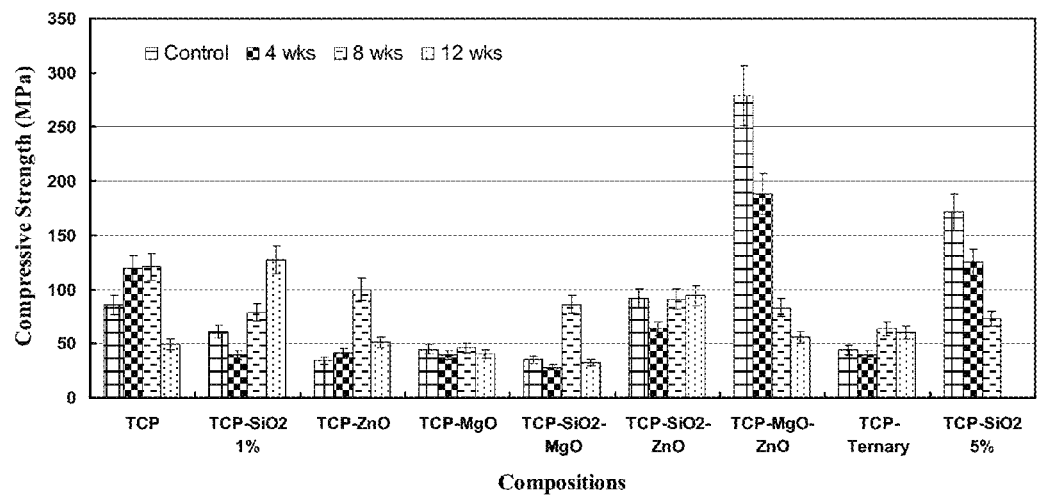
FIG. 31 shows, according to particular exemplary aspects of the present invention, strength degradation behavior up to 12 weeks in SBF.
Figure 32:
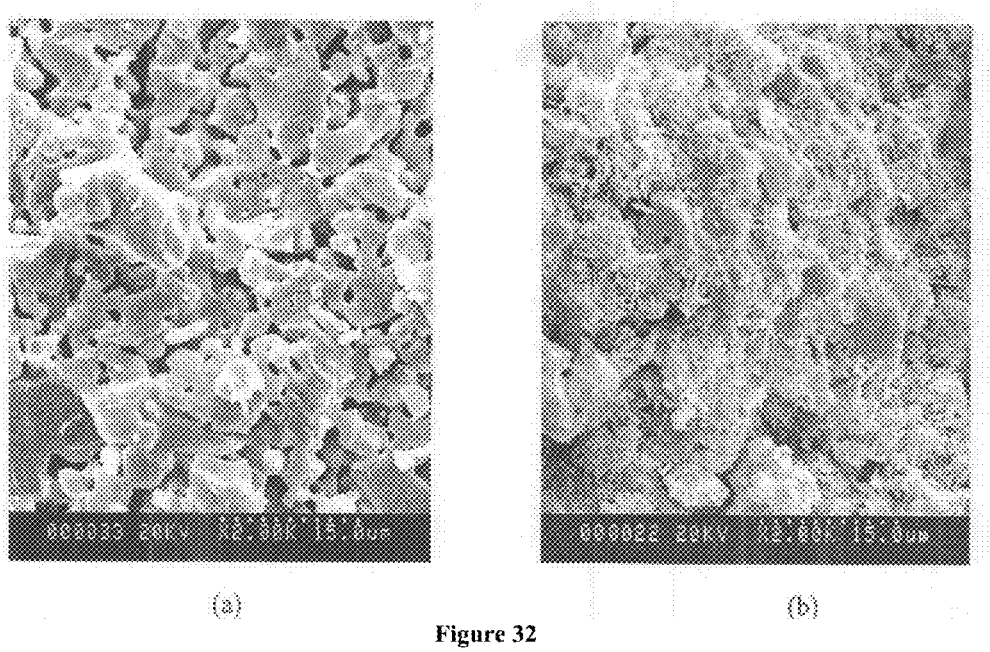
FIGS. 32, 33, 34 and 35 show, according to particular exemplary aspects of the present invention, show fracture surfaces of compression samples after 12 weeks in SBF. All compositions with single dopant and pure TCP show deposition inside the sample that suggests a continuous network of porosity in the sintered samples.
Figure 33:
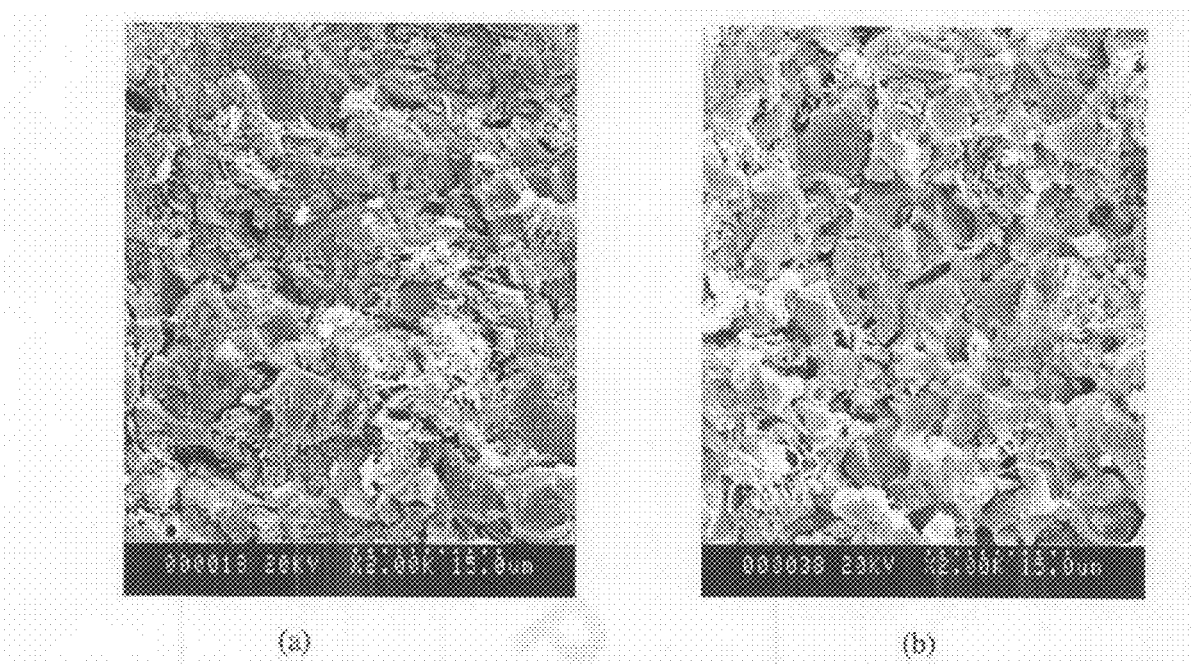
Figure 34:
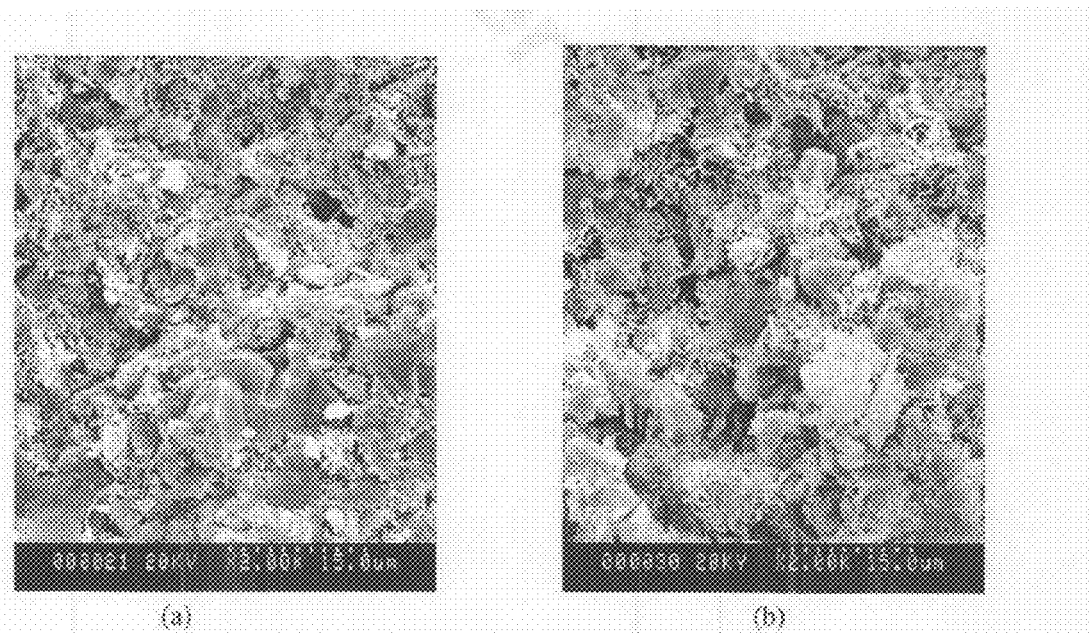
Figure 35:
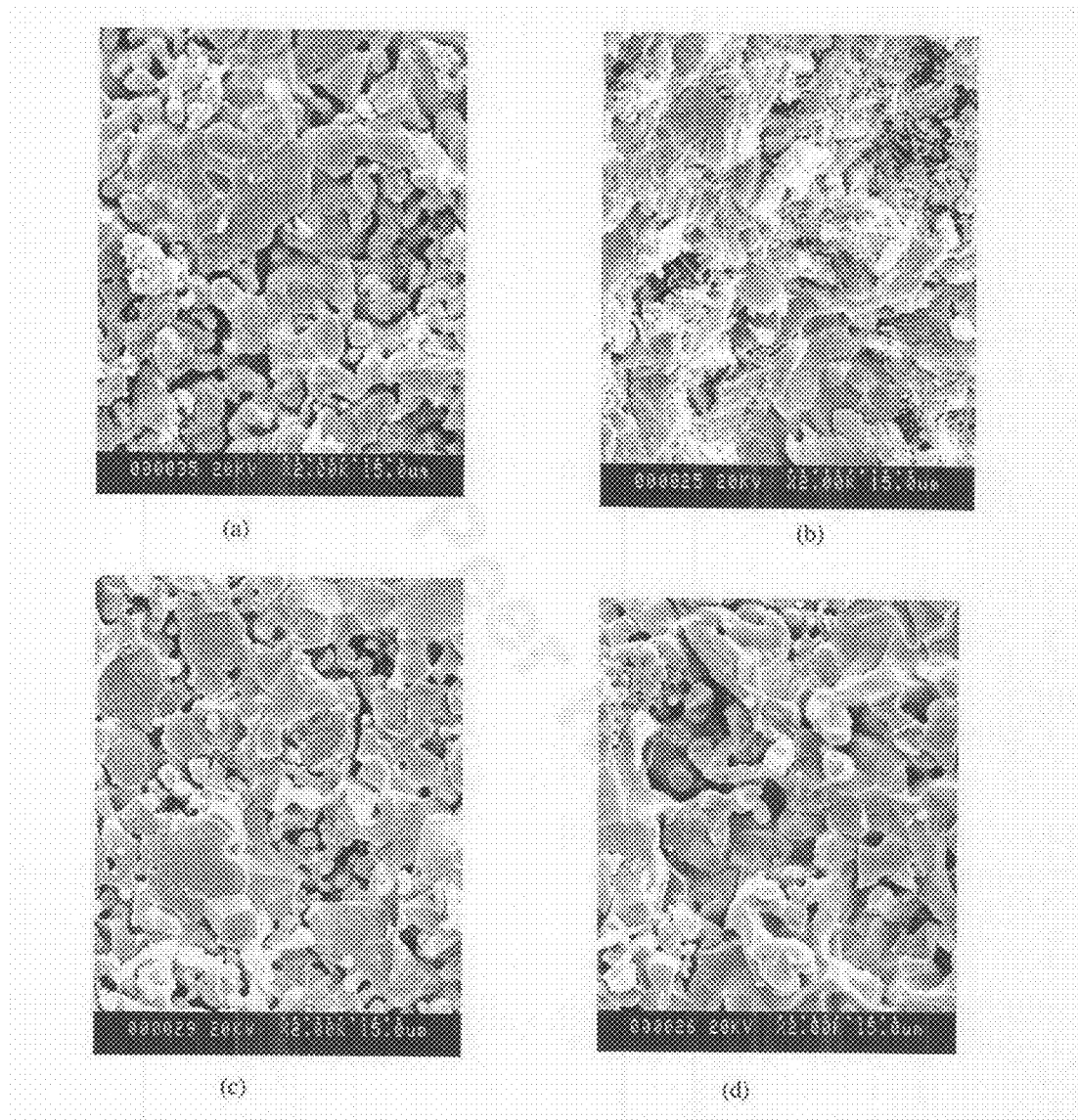

To further understand the rate of strength degradation and influence of dopants on that, 15 samples were kept in SBF up to 12 weeks. After $4^{th}$, $8^{th}$ and $12^{th}$ week, five samples were taken out each time, dried and tested for their compressive strengths. Dried samples were also measured for their weight to evaluate the weight change during the same period. Two different mechanisms can affect the change in compression strength and weight of TCP: (i) the degradation or dissolution effect which is the loss of strength due to the increase in porosity and weakened grain boundaries, and (ii) apatite and/or octacalcium phosphate (OCP) formation which fills the pores and increases the density and strength of the material. The final weight and strength will depend on which one of these mechanisms is the dominant one. FIG. 30 shows weight change as a function of composition up to 12 weeks. Except MgO—ZnO and the ternary compositions, all other cases a modest weight increase between 1-3% of their as starting sintered weight can be seen. Weight of 5 wt % SiO2 remained almost constant up to 8 weeks. Weight change was also influenced by starting density where lower density samples gained more weight due to the presence of initial interconnected porosity in them in which fluids could go in and form apatite and/or OCP. FIG. 31 shows strength degradation behavior up to 12 weeks in SBF.

For pure TCP, compressive strength increased from 83 MPa to 120 MPa during the $4^{th}$ week and maintained the same up to the $8^{th}$ week. However, during the $12^{th}$ week, strength dropped to 45 MPa. This result indicates that strength degradation in TCP is most significant after $8^{th}$ week and prior to that deposition mechanism controls the overall strength of the material. Overall, doped samples showed three general trends: (1) compressive strength of as sintered and samples after 12 weeks are fairly similar or remain constant, (2) compressive strength increased and (3) compressive strength decreased continuously as a function of time in SBF. For ZnO, MgO, $SiO_2$—ZnO, $SiO_2$—MgO and ternary compositions, strength remain almost constant over 12 weeks, however, there may be some variations during the 4th and the 8th week period. For 1 wt % $SiO_2$, strength increased continuously from 65 MPa for as sintered to 125 MPa after 12 weeks. Significant deposition can also be seen in this sample. Both ZnO—MgO and 5 wt % $SiO_2$, strength decreased continuously with time. For ZnO—MgO, from >275 MPa for as sintered, strength dropped to 65 MPa after 12 weeks in SBF. This was the biggest strength drop among all the compositions. For 5 wt % SiO2, strength drop was from 160 MPa to 80 MPa after 8 weeks. Overall, these results indicate that both dopant chemistry and amount can influence as sintered strength as well as in vitro strength degradation behavior significantly. FIGS. 32, 33, 34 and 35 show fracture surfaces of compression samples after 12 weeks in SBF. All compositions with single dopant and pure TCP show deposition inside the sample that suggests a continuous network of porosity in the sintered samples. This is related to the density of the samples and from TABLE 5, it is clear that pure TCP and single dopant samples had the lowest density of all the samples. Among the binary and ternary dopant samples, only $SiO_2$—ZnO sample showed some deposition, but others had no evidence of any deposition in the fracture surface. Clearly degradation and deposition in these samples took place primarily at the surface.

Figure 36:
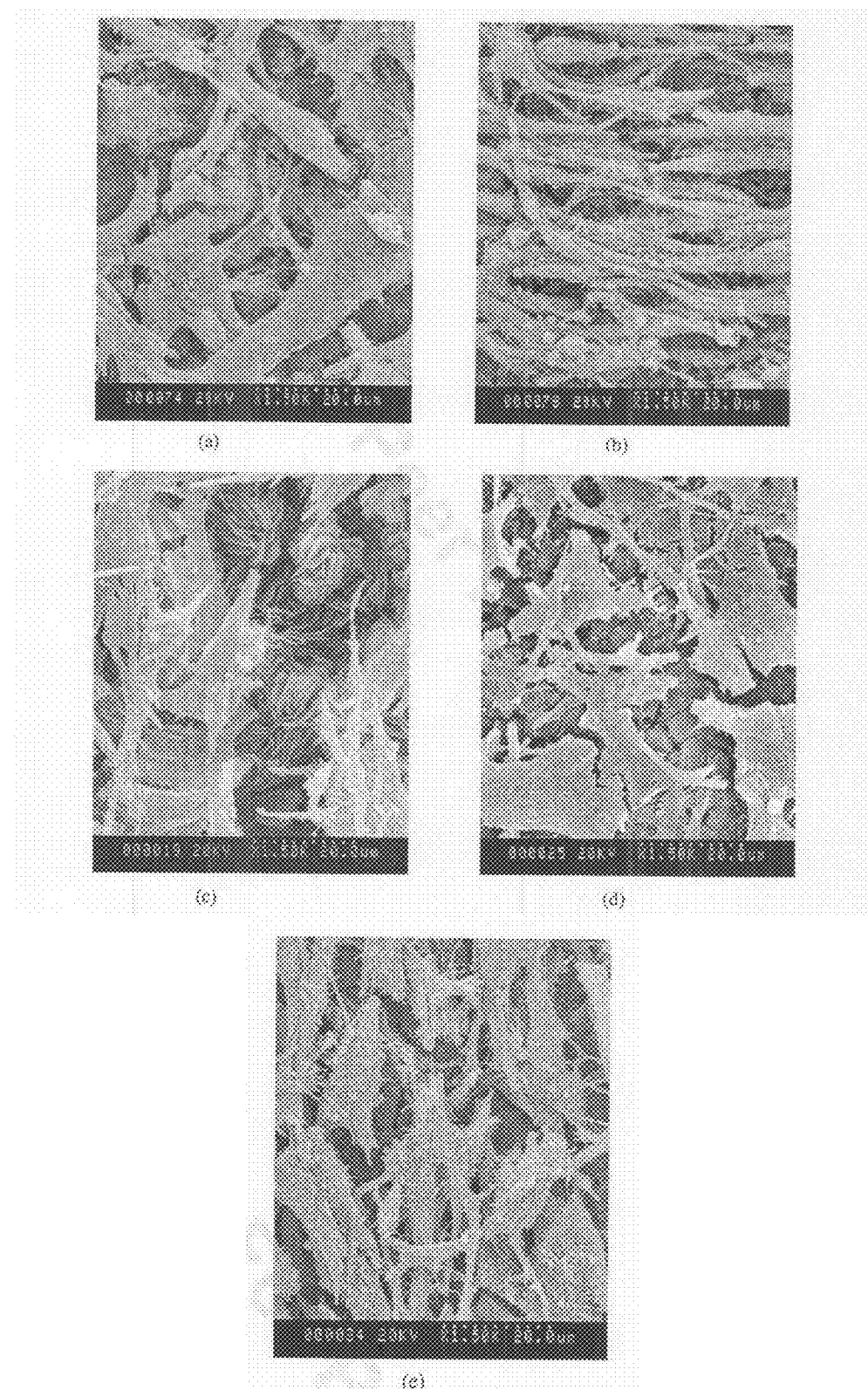
FIG. 36 shows, according to particular exemplary aspects of the present invention, OPC1 cells on pure TCP and single dopant samples. Cell proliferation was clearly evident in all cases, however, ZnO doped samples showed extensive flaky deposition layer while MgO doped sample showed cell banding and layering. The cells displayed numerous lamellipodia and filopodia extensions, which are noted contacting cells to the substrate and to neighboring cells.
Figure 37:
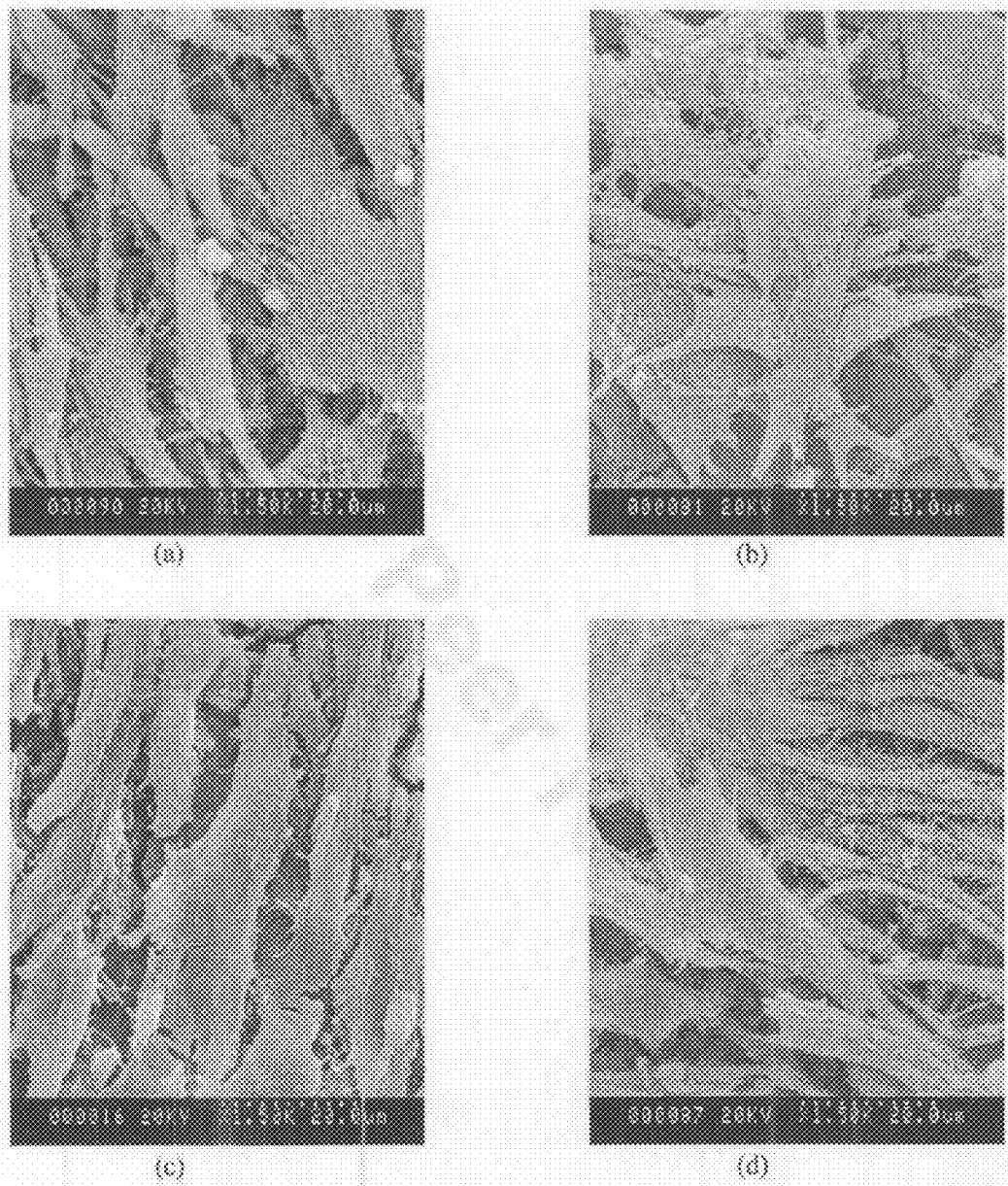
FIG. 37 shows, according to particular exemplary aspects of the present invention, OPC1 cells on binary and ternary compositions. All sample surfaces are fully confluent with OPC1 cells. Some layering of cells is also visible after 11 days.
Figure 38:
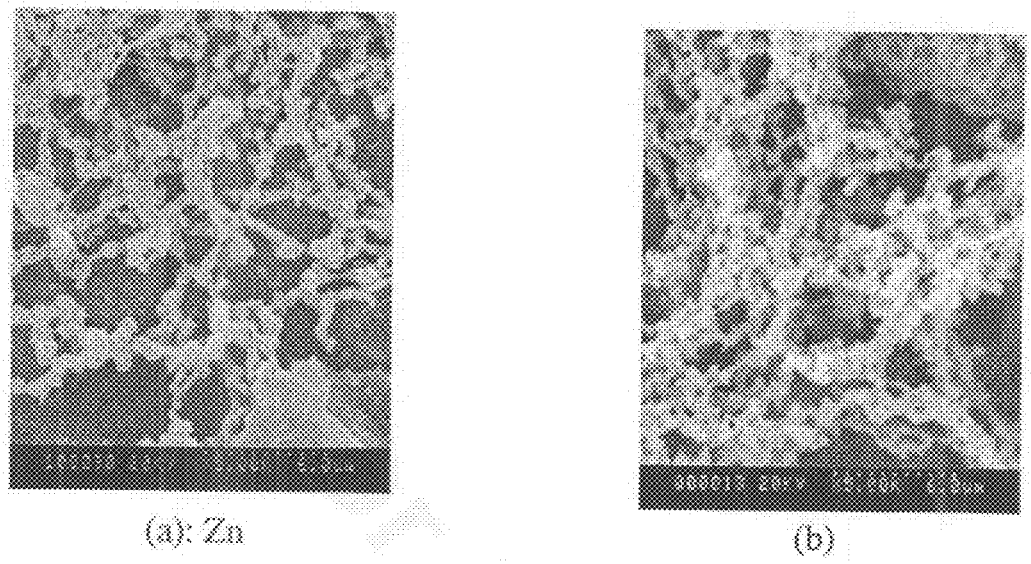
FIG. 38 shows, according to particular exemplary aspects of the present invention, a three dimensional fibrillar network of ECM formation in both of these surfaces. Numerous apatite-like granules were also precipitated on the collagen ECM, revealing the ECM starting to mineralize.
Figure 39:
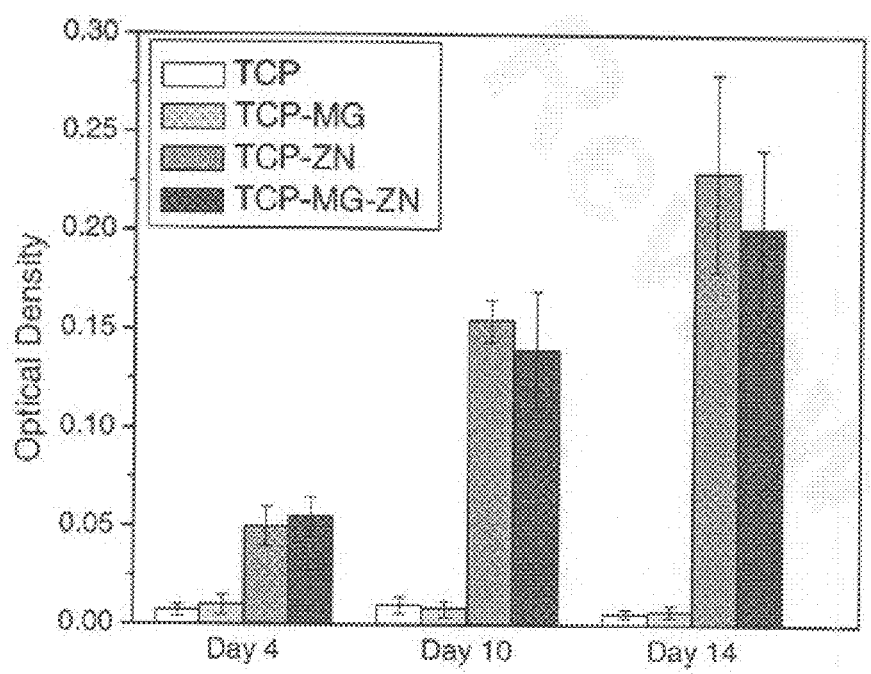
FIG. 39 shows, according to particular exemplary aspects of the present invention, results from MTT assay regarding cell proliferation of pure TCP, and with ZnO and ZnO—MgO dopants. The optical density is a representative of number of living cells on the substrate. It can be seen that both doped samples had significantly higher number of living cells compared to pure TCP, a good sign for cell proliferation.

Biological Properties:

Cell culture experiments were done using osteoblast precursor cell line 1 (OPC1) to determine toxicity due to the addition of dopants into TCP. It is important that dopants do not compromise the biocompatibility of TCP. If OPC1 cells are not affected by the dopants then they would tend to spread out and occupy as much surface area as possible, thus, having a more flattened structure. However, if there is some toxicity, cells will rather adhere to themselves than the material's surface, therefore, OPC1 cells will reduce the contact surface with the material and will look like a ball. Cell culture experiments were done at two intervals, 5 days and 11 days. These intervals were chosen because it was found that after day 5, cells on a bioactive surface should begin the proliferation process in which they spread to cover as much surface area as possible and after day 11 some differentiation should be in progress where the OPC1 cells nearest to the material begin to release calcium and phosphorous which are the major constituents of bone material onto the surface.([45]) Overall, after 11 days all samples showed good bioactivity and cell spreading. Some directional growth of cells was observed, an indication for differentiation. FIG. 36 shows OPC1 cells on pure TCP and single dopant samples. Cell proliferation was clearly evident in all cases, however, ZnO doped samples showed extensive flaky deposition layer while MgO doped sample showed cell banding and layering. The cells displayed numerous lamellipodia and filopodia extensions, which are noted contacting cells to the substrate and to neighboring cells. This suggests good cell-materials interactions and cell to cell communication. Extracellular matrix (ECM)([46]) formation was found on the surface of cells and between the neighboring cells, which were confirmed using EDS to be composed of Ca and P. FIG. 37 shows OPC1 cells on binary and ternary compositions. All sample surfaces are fully confluent with OPC1 cells. Some layering of cells is also visible after 11 days. To further understand the formation of ECM, ZnO and MgO—ZnO doped samples were selected and OPC1 cells were cultured for 56 days. FIG. 38 shows a three dimensional fibrillar network of ECM formation in both of these surfaces. Numerous apatite-like granules were also precipitated on the collagen ECM, revealing the ECM starting to mineralize. FIG. 39 shows results from MTT assay regarding cell proliferation of pure TCP, and with ZnO and ZnO—MgO dopants. The optical density is a representative of number of living cells on the substrate. It can be seen that both doped samples had significantly higher number of living cells compared to pure TCP, a good sign for cell proliferation.

Figure 40:
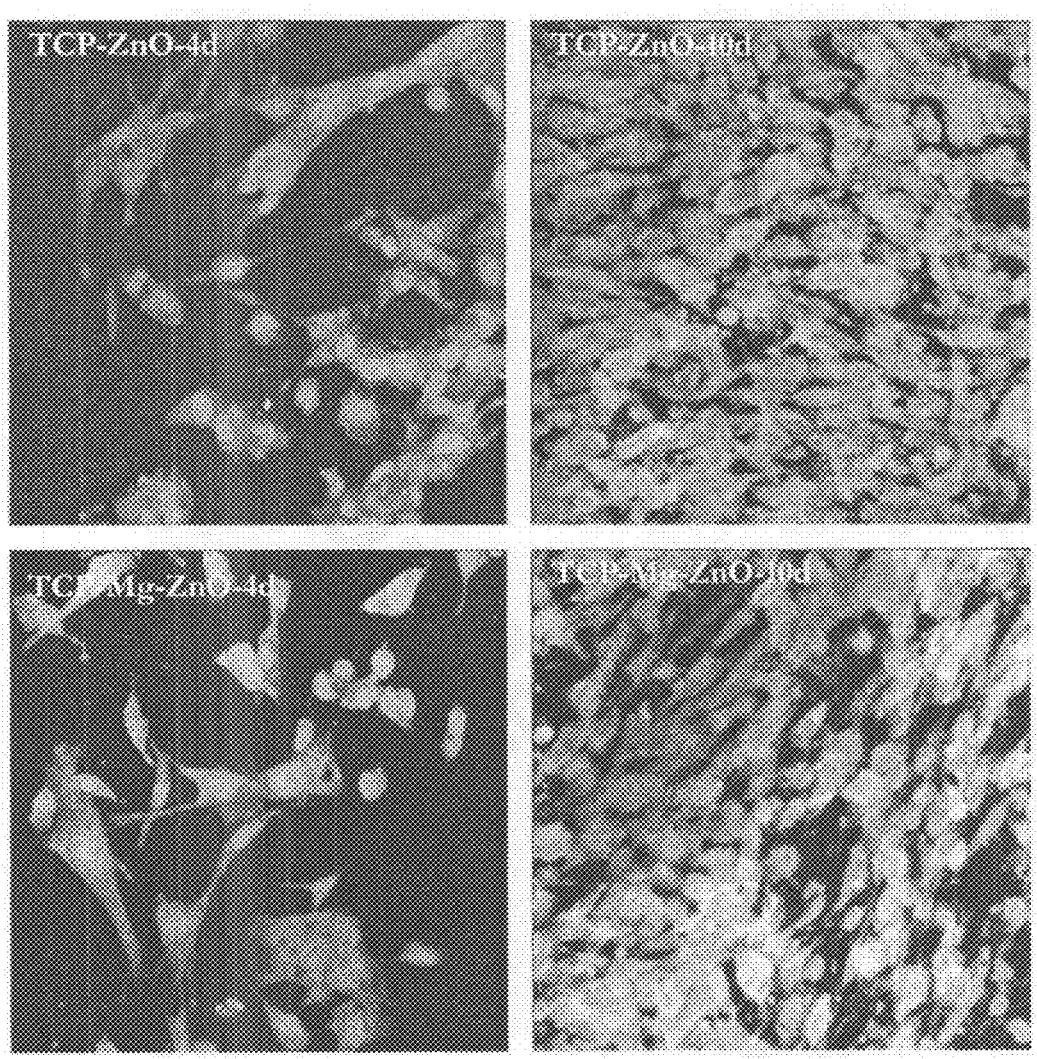
FIG. 40 shows, according to particular exemplary aspects of the present invention, the confocal micrographs of vinculin expression in OPC1 cells at culture on TCP-ZnO and TCP-MgO—ZnO. Vinculin within the cells can be identified by the expression of green fluorescence, and nuclei counterstained with PI expressed red fluorescence.
Figure 41:
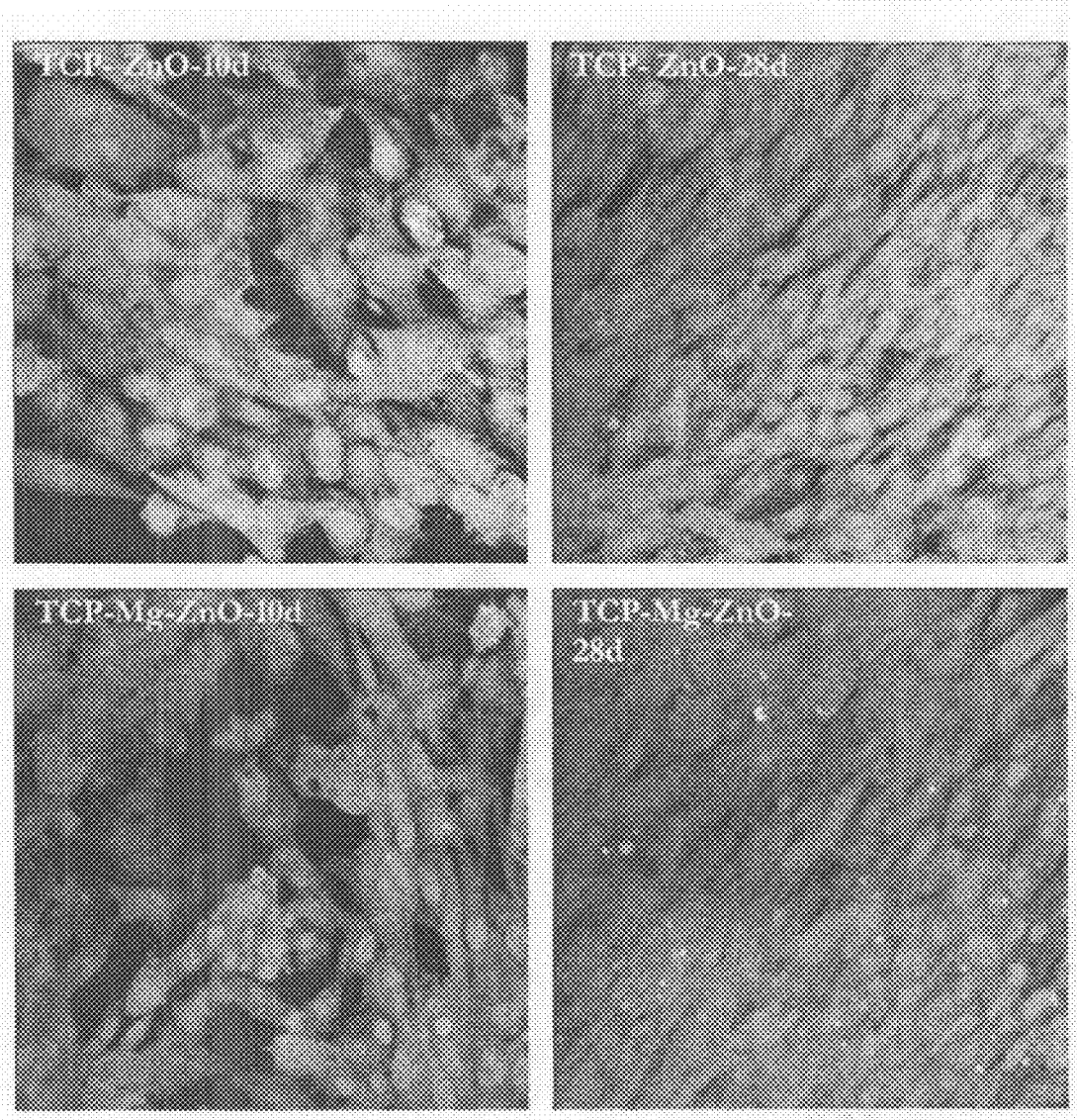
FIG. 41 shows, according to particular exemplary aspects of the present invention, the confocal micrographs of ALP expression in OPC1 cells cultured on TCP-ZnO and TCP-MgO—ZnO. ALP within the cells was identified by the expression of green fluorescence, and nuclei counterstained with PI in the mounting medium expressed red fluorescence. At day 10 and day 28, OPC1 cells cultured on TCP-ZnO and TCP-MgO—ZnO displayed positive immunostaining for ALP. OPC1 cells showed obvious ALP production after 10 days of culture. With the increase of culture time, ALP activity also increased significantly.

To further understand cell-materials interaction, protein expression was characterized for only ZnO and Zno-MgO doped compositions only. Different protein markers can be characterized for different stages of cell-materials interactions. Since these samples already showed good cell proliferation, we focused our effort on proteins related to cell adhesion and cell differentiation. For cell adhesion, vinculin expression was studied and for cell differentiation, expression of alkaline phosphate (ALP) was studied. The confocal micrographs of vinculin expression in OPC1 cells at culture on TCP-ZnO and TCP-MgO—ZnO are shown in FIG. 40. Vinculin within the cells can be identified by the expression of green fluorescence, and nuclei counterstained with PI expressed red fluorescence. OPC1 cells cultured on TCP-ZnO and TCP-MgO—ZnO displayed positive immunostaining for vinculin. OPC1 cells showed obvious vinculin production after 4 days of culture. With the increase of culture time, vinculin activity increased significantly. FIG. 41 shows the confocal micrographs of ALP expression in OPC1 cells cultured on TCP-ZnO and TCP-MgO—ZnO. ALP within the cells was identified by the expression of green fluorescence, and nuclei counterstained with PI in the mounting medium expressed red fluorescence. At day 10 and day 28, OPC1 cells cultured on TCP-ZnO and TCP-MgO—ZnO displayed positive immunostaining for ALP. OPC1 cells showed obvious ALP production after 10 days of culture. With the increase of culture time, ALP activity also increased significantly.

The results obtained indicated that doped TCPs are better for cell attachment and growth. As a bio-resorbable material, TCP degrades within human body environment. Fast dissolution of TCP diminishes cell-material interface even though the interface has well established. In addition to dissolution, the change in the surrounding milieu after dissolution is also an important reason for the relatively poor biocompatibility of TCP. The dissolution of TCP increases the calcium and phosphate ionic concentration in surrounding fluid, and results in the re-crystallization of apatite over the surface. The formation of the apatite on the surface decreases the pH of the environment which in turn increases the solubility of TCP. The addition of zinc decreases the dissolution, and enhances the stability of TCP ceramics. It is helpful for cell attachment and growth. In this Example, TCP-ZnO and TCP-MgO—ZnO exhibited excellent biocompatibility with OPC1 cell. This result suggests that these two samples promote better cell attachment and spreading behavior. As an adhesive molecule, vinculin aids in the assemblage of focal contact by crosslinking and recruiting other proteins to form adhesion plaques.[47] The existance of vinculin represents the TCP-MgO—ZnO, indicating that these two samples have surface properties favorable for cell adhesion. Moreover, formation of collagenous ECM indicates that OPC1 cells on these two samples are capable of producing a matrix suitable for mineralization and suggest initiation of a biomineralization pathway. Immunocytochemistry showed that strong ALP expression in the OPC1 cells cultured on ZnO and TCP-MgO—ZnO. ALP is a major marker characteristic of osteoblasts. ALP is regarded as an early marker for osteoblast differentiation, and it is generally accepted that as the specific activity of ALP in a population of bone cells increases there is a corresponding shift to a more differentiated state.([48]) High levels of ALP expression on these two samples can be related to rapid differentiation of OPC1 cells on these surfaces.

Therefore, according to particular aspects, β-tricalcium phosphate ceramic compacts were made with the addition of MgO, ZnO and $SiO_2$ dopants in various combinations. These samples were then tested for physical, mechanical, and biological properties. The compacts doped with MgO, 1 wt % $SiO_2$ and 5 wt % $SiO_2$ separately did not alter densification, however, 0.25 wt % ZnO decreased sintered density of TCP. All binary and ternary dopant compositions showed an increase in densification compared to pure TCP. Weight change measurements after SBF treatment indicated that all single component systems and TCP-$SiO_2$—ZnO produced an increase in weight which was an indication of apatite growth. This data was also supported by microstructural analysis. However, for all binary and ternary compositions, weight change was negligible and sometimes negative, an indication that there was little or no apatite formation. Microstructural analysis revealed signs of surface dissolution after 12 weeks for all samples. TCP was found to degrade after 8 weeks in SBF solution. TCP 1 wt % $SiO_2$ compacts showed a continuous increase in compressive strength for 12 weeks in SBF while TCP-5 wt % $SiO_2$ and TCP-MgO—ZnO compositions both illustrated a continuous decrease in compressive strengths over 12 weeks in SBF. It was also found that degradation began after 2 weeks for these compositions. For all other compositions, compressive strengths after 12 weeks remained similar to their as sintered value. Fractographic analysis revealed apatite formation inside the sample for pure TCP and single dopant compositions suggesting an interconnected open porosity throughout the sample. However, for binary and ternary dopants, higher densification reduced the open pore network. In vitro cell materials interaction work with OPC1 cells proved that all compositions were biocompatible and non-toxic. Specific experiments on adhesion, proliferation and differentiation showed that dopants play a significant role towards improving cell-materials interactions.

References Relating to Example 10

[1] www.biomet.com

[2] D. Shi, *Biomaterials and Tissue Engineering*, pp. 2-200, Springer Berlin Heidelberg, New York, 2004.

[3] V. Mow and R. Huskies, *Basic Orthopaedic Biomechanics and Mechano-Biology*, Third Edition, pp. 124-517, Lippencott Williams & Wilkins, Philadelphia, 2005.

[4] P. Ducheyne and Q. Qiu, "Bioactive ceramics: the effect of surface reactivity on bone formation and bone cell function", *Biomaterials* 20 [23-24] 2287-303 (1999).

[5] H. H. Vandenburgh, S. Hatfaludy, P. Karlisch and J. Shansky, "Mechanically induced alterations in cultured skeletal muscle growth", *J Biomech.*, 24 [Suppl 1] 91-9 (1991).

[6] K. J. L. Burg, S. Porter and J. F. Kellam, "Biomaterial developments for bone tissue engineering". *Biomaterials*, 21 [23] 2347-59 (2000).

[7] R. Lanza, R. Langer and W. Chick, *Principles of Tissue Engineering*, Academic Press, Inc, 1997.

[8] K. de Groot, "Effect of porosity and physicochemical properties on the stability, resorption, and strength of calcium phosphate ceramics". In *Bioceramics: Material characteristics versus in-vivo behavior, Ann. N. Y. Acad. Sci.*, 523, 227 (1998).

[9] A. Ravaglioli and A. Krajewski, *Bioceramics Materials, Properties, Applications*, pp. 16-54, Chapman & Hall, London, 1992.

[10] M. J. Yaszemski, R. G. Payne, W. C. Hayes, R. Langer and A. C. Mikos, "Evolution of bone transplantation: molecular, cellular and tissue strategies to engineer human bone", *Biomaterials*, 17 [2] 175-85 (1996).

[11] D. Buser, K. Dula, H. P. Hirt and H. Berthold, "Localized ridge augmentation using guided bone regeneration"; pp. 189-233 in *Guided bone regeneration in implant dentistry*, Edited by D. Buser, C. Dahlin and R. K. Schenk, Quintessenz, Chicago, 1994.

[12] H. Yamada, *Strength of Biological Materials*, Williams & Wilkins, Baltimore, Md., 1970.

[13] I. R. Gibson, M. Akao, S. M. Best and W. Bonfield, *Bioceramics* 9, 173 (1996).

[14] J. C. Elliot, *Structure and Chemistry of the Apatites and Other Calcium Orthophosphates*, Elsevier Science, Amsterdam, 1994.

[15] I. R. Zerbo, A. L. Bronckers, G. L. de Lange, G. J. van Beek and E. H. Burger, "Histology of human alveolar bone regeneration with a porous tricalcium phosphate—A report of two cases", *Clin. Oral. Implants Res.*, 12 [4] 379-384 (2001).

[16] R. LeGeros and G. Daculsi, in "handbook of bioactive ceramics", Edited by T. Yamanuro, L. Hench and J. Wilson, CRC Press, Boca Raton, 1990.

17 W. Suchanek and M. Yoshimura, "Processing and properties of HAp based biomaterials for use as hard tissue replacement implants", *J. Mater. Res.*, 13 [1] 94-109 (1998).

18 J. B. Park, *Biomaterials Science and Engineering*, Plenum Press, New York, N.Y., 1984.

19 R. Z. LeGeros, G. Daculsi, R. Kijkowska and B. Kerebel, "The effect of magnesium on the formation of apatites and whitlockites"; pp. 11-9 in *Magnesium in Health and Desease*, Edited by Y. Itokawa and J. Durlach, John Libbey; London, 1989.

20 J. C. Knowles, S. Talal and J. D. Santos, "Sintering effects in a glass reinforced hydroxyapatite", *Biomaterials*, 17 [14] 1437 (1996).

21 Z. Seeley, A. Bandyopadhyay and S. Bose, "Influence of TiO2 and Ag2O Addition on Tricalcium Phosphate Ceramics", revised version submitted to *Journal of Biomedical Materials Research: Part A*, April 2006.

22 Z. Seeley, A. Bandyopadhyay and S. Bose, "Resorbable Ceramics in Tissue Engineering: Influence of NaF and CaO addition in TCP," submitted to *Journal of Biochemistry and Biotechnology*—Special Issue on Tissue Engineering (Invited), March 2006.

23 E. Bertoni, A. Bigi, G. Cojazzi, M. Gandolfi, S. Panzavolta and N. Rover, "Nanocrystals of Magnesium and fluoride substituted hydroxyapatite". *J. Inorg. Biochem.*, 72, 29-35 (1998).

24 D. Rokusek, C. Davitt, A. Bandyopadhyay, S. Bose and H. L. Hosick, "Interaction of human osteoblasts with bioinert and bioactive ceramic substrates", J. Biomed. Mater. Res., 75A [3] 588-94 (2005).

25 S. R. Kim, J. H. Lee, Y. T. Kim, D. H. Riu, S. J. Jung, Y. J. Lee, S. C. Chung and Y. H. Kim, "Synthesis of Si, Mg substituted hydroxyapatites and their sintering behaviors", *Biomaterials*. 24 [8] 1389-98 (2003).

26 M. Percival, "Bone health & Osteoporosis", *Appl. Nutr. Sci. Rep.*, 5 [4] 1 (1999).

27 L. Calderin, X. Yin, M. J. Stott and M. Sayer, "Density Functional Study of Structural, Electronic and Vibrational properties of Mg- and Zn-doped Tricalcium Phosphate Biomaterials", *Biomaterials*, 23 [20] 4155-4163 (2002).

28 A. Ito, K. Ojima, H. Naito, N. Ichinose and T. Tateishi, "Preparation, solubility, and cytocompatibility of zinc-releasing calcium phosphate ceramics", *J. Biomed. Mater. Res.*, 50 [2] 178-183 (2000).

29 E. J. Underwood, *Trace elements in human and animal nutrition, 4th edition*, pp. 196, Academic Press, London, 1977.

30 M. Hashizume and M. Yamaguchi, "Stimulatory effect of β-alanyl-1-histidinato zinc on cell proliferation is dependent on protein synthesis in osteoblastic MC3T3-E1 cells", *Mol. Cell Biochem.*, 122, 59-64 (1993).

31 S. Kishi and M. Yamaguchi, "Inhibitory effect of zinc compounds on osteoclast-like cell formation in mouse marrow culture", *Biochem. Pharmacol.*, 48, 1225-1230 (1994).

32 B. S. Moonga and D. W. Dempster, "Zinc is a potent inhibitor of osteoclastic bone resorption in vitro", *J. Bone Miner. Res.*, 10 [3] 453-457 (1995).

33 M. Otsuka, Y. Ohshita, S. Marunaka, Y. Matsuda, A. Ito, N. Ichinose, K. Otsuka and W. Higuchi, "Effect of controlled zinc release on bone mineral density from injectable Zn-containing β-tricalcium phosphate suspension in zinc-deficient diseased rats", *J. Biomed. Mater. Res.*, 69A [3] 552-560 (2004).

34 A. Bandyopadhyay, E. A Withey, J. Moore and S. Bose, "Influence of ZnO doping in calcium phosphate ceramics", in press, *Materials Science and Engineering C*, November 2005.

35 X. Yin, L. Calderin, M. J. Stott, M. Sayer, "Density Functional Study of Structural, Electronic and Vibrational properties of Mg- and Zn-doped Tricalcium Phosphate Biomaterials", *Biomaterials* 23 [20] 4155-4163 (2002).

36 E. M. Carlisle, "Silicon: a possible factor in bone calcification", Science. 167 [3916] 279-80 (1970).

37 S. Hayakawa, K. Tsuru, C. Ohtsuki and A. Osaka, "Mechanism of apatite formation on a sodium glass in a simulated body fluid", *J. Am. Ceram. Soc.*, 82 [8] 2155-60 (1999).

38 Knabe C, Berger G, Gildenhaar R, Meyer J, Howlett C R, Markovic B and Zreiqat H. Effect of rapidly resorbable calcium phosphates and a calcium phosphate bone cement on the expression of bone-related genes and proteins in vitro," *J Biomed Mater Res.* 69A:145-154 (2004).

39 C. Knabe, G. Berger, R. Gildenhaar, C. R. Howlett, B. Markovic and H. Zreiqat, "The functional expression of human bone-derived cells grown on rapidly resorbable calcium phosphate ceramics", *Biomaterials*. 25 [2] 335-44 (2004).

40 T. Kokubo, H. Kushitani, S. Sakka, T. Kitsugi, T. Yamamuro, "Solutions able to reproduce in vivo surface-structure changes in bioactive glass-ceramics A-W", *J. Biomed. Mater. Res.*, 24, 721-34 (1990).

41 S. R. Winn, G. Randolph, H. Uludag, S. C. Wonng, G. A. Hair and J. O. Hollinger, "Establishing an immortalized human osteoprecursor cell line: OPC1". *J. Bone Mineral. Res.*, 14 [10] 1721-33 (1999).

42 H. Kawamura, A. Ito, S. Miyakawa, P. Layrolle, K. Ojima, N. Ichinose and T. Tateishi, "Stimulatory effect of zinc-releasing calcium phosphate implant on bone formation in rabbit femora", *J. Biomed. Mater. Res.*, 50 [2] 184-190 (2000).

43 Q. Y. Zhang, Y. Leng and R. L. Xin. "A Comparative Study of Electrochemical Deposition and Biomimetic Deposition of Calcium Phosphate on porous Titanium", *Biomaterials;* 26 [16] 2857-65 (2005).

44 Y. Leng, X. Lu and J. Chen, "Identifying Calcium Phosphates Formed in Simulated Body Fluid by Electron Diffraction", *Hey. Eng. Mater.*, 254 [25] 339-42 (2004).

45 S. J. Kalita, S. Bose, H. L. Hosick and A. Bandyopadhyay, "CaO—P₂O5-Na₂O based sintering additives for hydroxyapatite (HAp) ceramics", *Biomaterials,* 25 [12] 2331-9 (2004).

46 46K. Qiu, X. J. Zhao, C. X. Wan, C. S. Zhao, Y. W. Chen, "Effect of strontium ions on the growth of ROS17/2.8 cells on porous calcium polyphosphate scaffolds", *Biomaterials;* 27 [8] 1277-86 (2006).

47 E. Zamir and B. Geiger, "Molecular complexity and dynamics of cell-matrix adhesions", *J. Cell Sci.* 114 [20] 3583-90 (2001).

48 J. E. Aubin and F. Liu, "The osteoblast lineage"; pp. 51-67 in *Principles of bone biology* Edited by J. P. Bilezikian, L. G. Raisz and G. A. Rodan, Academic Press, San Diego, 1996.

The invention claimed is:

1. A bioresorbable and biocompatible composition for bioengineering, restoring, or regenerating a target tissue or musculoskeletal tissue, comprising:

a three-dimensional scaffold material comprising a plurality of calcium phosphate containing ceramic particles interconnected to form a porous network between and among the ceramic particles, the individual calcium phosphate-containing ceramic particles having:
a calcium phosphate material having a formula ($Ca_x(PO_4)_y$, where x=1 or more, and y=1 or more), or hydroxylated variants thereof; and
at least one dopant forming a single phase with the calcium phosphate material, the dopant being selected from the group consisting of ZnO, NaF, KF, FeO, $Fe_2O_3$, SrO, CuO, $SiO_2$, $TiO_2$, $Ag_2O$ and $CaCO_3$, the dopant having a concentration sufficient to render the scaffold material resorbable at a target resorption rate under a body, body fluid or simulated body fluid condition, thereby achieving a target mechanical strength and target strength degradation of the scaffold material under the body, body fluid or simulated body fluid conditions.

2. The composition of claim 1, wherein the at least one dopant is present in a single-element or multi-element amount between 0 and about 10 wt %, from about 0.5 to about 5 wt %, from about 1 to about 3 wt %, from about 2 to about 7 wt %, from about 3 to about 7 wt %, or from about 4 to about 7 wt %.

3. The composition of claim 1, wherein biocompatibility comprises biocompatibility with respect to at least one cell or tissue type selected from the group consisting of eukaryotic cells, mammalian cells, bone forming or restructuring cells, osteoplastic or osteoplastic precursor cells, cartilage cells, muscle cells, stem cells, differentiated stem cells, bone marrow stem cells, and nerve cells.

4. The composition of claim 1, wherein the tissue comprises at least one selected from the group consisting of bone, cartilage, muscle and musculoskeletal tissue.

5. The composition of claim 2, wherein the at least one dopant is present in an amount sufficient to maintain the compressive strength of the material at about 30% of original or higher, 40% of original or higher, 50% of original or higher, 60% of original or higher, 70% of original or higher, 80% of original or higher, or 90% of original or higher, in each case, for a period of at least 6, at least 7, least 8, at least 9, at least 10, at least 11 or at least 12 months under body, body fluid or simulated body fluid conditions, to provide for a slow-degrading composition.

6. The composition of claim 2, wherein the at least one dopant is present in an amount sufficient to reduce the compressive strength of the material to about 90%, or less than 90%, 80%, or less than 80%, 70%, or less than 70%, 60%, or less than 60% or 50%, or less than 50% of original, in each case, within a period of about 3 months, about 4 months, about 5 months or about 6 months under body, body fluid or simulated body fluid conditions, to provide for a fast-degrading composition.

7. The composition of claim 2, wherein the at least one dopant is selected from the group consisting of SrO, ZnO, $TiO_2$, and $SiO_2$ dopants, present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %.

8. The composition of claim 1, wherein the ceramic comprises a multi-element dopant comprising at least two dopants selected from the group consisting of $Zn^{2+}$, $Si^{2+}$, $Na^+$, $K^+$, $Sr^{2+}$, $Fe^{3+}/Fe^{2+}$, $Ti^{4+}$, $Co_3^{2-}$, ZnO, NaF, KF, FeO, $Fe_2O_3$, SrO, CuO, $SiO_2$, $TiO_2$, $Ag_2O$ and $CaCO_3$, present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %.

9. The composition of claim 1, wherein the ceramic comprises at least one dopant ions and/or oxides present in a single-element or multi-element amount between 0 and about 10 wt %, from about 0.5 to about 5 wt %, from about 1 to about 3 wt %, from about 2 to about 7 wt %, from about 3 to about 7 wt %, from about 4 to about 7 wt %.

10. The composition of claim 1, wherein the calcium phosphate material comprises at least one single or mixed phase calcium phosphate material.

11. The composition of claim 1, wherein the calcium phosphate comprises at least one single or mixed phase calcium phosphate material having calcium to phosphate ratio (Ca/P) in a range from about 1.4:1 to about 1.7:1, or from about 1.0:1 to about 2.0:1.

12. The composition of claim 11, wherein the calcium to phosphate ratio is about 1.5:1, or about 1.67:1.

13. The composition of claim 1, wherein the calcium phosphate containing ceramic comprises at least one of tricalcium phosphate (TCP; $Ca_3(PO_4)_2$) and Hydroxyapatite (Hap; $Ca_{10}(PO_4)_6(OH)_2$).

14. The composition of claim 1, wherein the porous network has pore sizes in the range of about 10 nm to about 5 mm, or from about 10 nm to about 500 μm, or from about 1 nm to about 1 μm.

15. The composition of claim 1, wherein the scaffold material comprises dense to solid structures, or porous structures having internal cavities with sizes varying from nano-scale to larger sizes, or micro porous structures, wherein a core of the scaffold material is comprised of a geometric pattern of material with voided areas or low density structures with a quasi-solid exterior.

16. The composition of claim 1, further comprising at least one chemical, drug, growth factor or biological agent deposited, incorporated into, or stored within and/or on a surface of the scaffold material or within one or more pores thereof to operatively provide for release, controlled release or burst release of the agent to facilitate bioengineering, restoring or regenerating bone or other tissue.

17. The composition of claim 16, wherein the at least one agent comprises at least one selected from the group consisting of antibiotics, antimicrobial agents, growth factors, osteoinductive growth factors, drugs, polypeptides and proteins.

18. The composition of claim 17, wherein the at least one agent can be selectively activated and/or released at set times by the application of at least one chemical, electrical, magnetic or photochemical triggering event.

19. A bioresorbable and biocompatible composition for bioengineering, restoring, or regenerating a target tissue or musculoskeletal tissue, comprising:
a three-dimensional scaffold material comprising a plurality of calcium phosphate containing ceramic participles interconnected to form a porous network between and among the ceramic particles, the individual calcium phosphate containing ceramic particles having a calcium phosphate material with a formula ($Ca_x(PO_4)_y$, where x=1 or more, and y=1 or more), or hydroxylated variants thereof and at least one dopant forming a single phase with the calcium phosphate material, the dopant being selected from the group consisting of NaF, CaO, $SiO_2$, $TiO_2$, and $Ag_2O$, the dopant having a concentration sufficient to render the scaffold material resorbable at a target resorption rate under a body, body fluid or simulated body fluid condition, thereby achieving a target mechanical strength and target strength degradation of the scaffold material under the body, body fluid or simulated body fluid conditions.

20. The composition of claim 19, wherein the at least one dopant is present in a single-element or multi-element amount between 0 and about 10 wt %, from about 0.5 to about 5 wt %, from about 1 to about 3 wt %, from about 2 to about 7 wt %, from about 3 to about 7 wt %, or from about 4 to about 7 wt %.

21. The composition of claim 19, wherein the at least one dopant includes a multi-element dopant having NaF, CaO, $Ag_2O$, and $TiO_2$ at a concentration between 0 and about 10 wt %, between about 0.5 to about 5 wt %, between about 1 to about 3 wt %, between about 2 to about 7 wt %, between about 3 to about 7 wt %, or between about 4 to about 7 wt %.

22. The composition of claim 19, wherein the at least one dopant includes at least one of NaF, CaO, $Ag_2O$, or $TiO_2$ at a concentration between 0 and about 10 wt %, between about 0.5 to about 5 wt %, between about1 to about 3 wt %, between about 2 to about 7 wt %, between about 3 to about 7 wt %, or between about 4 to about 7 wt %.

23. The composition of claim 19, wherein the calcium phosphate comprises at least one single or mixed phase calcium phosphate material having calcium to phosphate ratio (Ca/P) in a range from about 1.4:1 to about 1.7:1, or from about 1.0:1 to about 2.0:1.

\* \* \* \* \*